United States Patent
Norcross et al.

(10) Patent No.: US 12,091,397 B2
(45) Date of Patent: Sep. 17, 2024

(54) DIHYDROQUINOLINONES FOR MEDICAL TREATMENT

(71) Applicant: C4 Therapeutics, Inc., Watertown, MA (US)

(72) Inventors: Roger Norcross, Basel (CH); Adrian Britschgi, Basel (CH); Fabian Dey, Basel (CH); Annick Goergler, Basal (CH); Eric Andre Kusznir, Basel (CH); Moreno Attilio Wichert, Basel (CH)

(73) Assignee: C4 Therapeutics, Inc.

( * ) Notice: Subject to any disclaimer, the term of this patent is extended or adjusted under 35 U.S.C. 154(b) by 0 days.

(21) Appl. No.: 17/878,753

(22) Filed: Aug. 1, 2022

(65) Prior Publication Data

US 2023/0192643 A1 Jun. 22, 2023

Related U.S. Application Data

(63) Continuation of application No. 16/809,345, filed on Mar. 4, 2020, now Pat. No. 11,401,256, which is a continuation of application No. PCT/EP2018/073555, filed on Sep. 3, 2018.

(30) Foreign Application Priority Data

Sep. 4, 2017 (EP) ..................................... 17189229

(51) Int. Cl.
| | |
|---|---|
| *C07D 401/04* | (2006.01) |
| *A61K 31/4375* | (2006.01) |
| *A61K 31/4704* | (2006.01) |
| *A61K 47/55* | (2017.01) |
| *A61P 35/00* | (2006.01) |
| *C07D 401/14* | (2006.01) |
| *C07D 413/14* | (2006.01) |
| *C07D 471/04* | (2006.01) |
| *C07D 487/04* | (2006.01) |
| *C07D 495/14* | (2006.01) |
| *C07D 519/00* | (2006.01) |

(52) U.S. Cl.
CPC ........ *C07D 401/04* (2013.01); *A61K 31/4375* (2013.01); *A61K 31/4704* (2013.01); *A61K 47/55* (2017.08); *A61P 35/00* (2018.01); *C07D 401/14* (2013.01); *C07D 413/14* (2013.01); *C07D 471/04* (2013.01); *C07D 487/04* (2013.01); *C07D 495/14* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 4,728,653 A | 3/1988 | Campbell et al. | |
| 4,792,561 A | 12/1988 | Walker et al. | |
| 4,898,872 A | 2/1990 | Campbell et al. | |
| 5,635,517 A | 6/1997 | Muller et al. | |
| 6,306,663 B1 | 10/2001 | Kenten et al. | |
| 7,041,298 B2 | 5/2006 | Deshaies et al. | |
| 7,208,157 B2 | 4/2007 | Deshaies et al. | |
| 7,235,562 B2 | 6/2007 | Kath et al. | |
| 9,125,915 B2 | 9/2015 | Miyoshi et al. | |
| 9,249,161 B2 | 2/2016 | Albrecht et al. | |
| 10,646,575 B2 | 5/2020 | Phillips et al. | |
| 10,660,968 B2 | 5/2020 | Phillips et al. | |
| 10,849,982 B2 | 12/2020 | Phillips et al. | |
| 10,905,768 B1 | 2/2021 | Phillips et al. | |
| 11,185,592 B2 | 11/2021 | Phillips et al. | |
| 11,254,672 B2 | 2/2022 | Norcross et al. | |
| 11,401,256 B2 | 8/2022 | Norcross et al. | |
| 11,407,732 B1 | 8/2022 | Henderson et al. | |
| 11,459,335 B2 | 10/2022 | Phillips et al. | |
| 2003/0008832 A1 | 1/2003 | Pamukcu et al. | |
| 2010/0331326 A1 | 12/2010 | Bock et al. | |
| 2013/0109672 A1* | 5/2013 | Boxer | A61P 35/02 514/212.07 |
| 2013/0190340 A1 | 7/2013 | Hedstrom et al. | |
| 2014/0302523 A1 | 10/2014 | Crews et al. | |
| 2014/0356322 A1 | 12/2014 | Crews et al. | |
| 2015/0119435 A1 | 4/2015 | Crews et al. | |
| 2015/0274738 A1 | 10/2015 | Gray et al. | |
| 2015/0291562 A1 | 10/2015 | Crew et al. | |
| 2016/0016966 A1 | 1/2016 | Amans et al. | |
| 2016/0022642 A1 | 1/2016 | Crews et al. | |
| 2016/0045607 A1 | 2/2016 | Crew et al. | |

(Continued)

FOREIGN PATENT DOCUMENTS

| | | |
|---|---|---|
| BR | PI1100318 A2 | 5/2013 |
| CN | 103421061 A | 12/2013 |

(Continued)

OTHER PUBLICATIONS

U.S. Appl. No. 17/164,446, Phillips et al., filed Feb. 1, 2021.

(Continued)

*Primary Examiner* — Medhanit W Bahta
(74) *Attorney, Agent, or Firm* — Knowles Intellectual Property Strategies, LLC

(57) ABSTRACT

The present invention provides dihydroquinolinone compounds which bind to the ubiquitously expressed E3 ligase protein cereblon (CRBN) and alter the substrate specificity of the CRBN E3 ubiquitin ligase complex, resulting in breakdown of intrinsic downstream proteins. The disclosed compounds are useful for the treatment of cancer.

13 Claims, 2 Drawing Sheets

(56) References Cited

U.S. PATENT DOCUMENTS

| | | |
|---|---|---|
| 2016/0046661 A1 | 2/2016 | Gray et al. |
| 2016/0058872 A1 | 3/2016 | Crew et al. |
| 2016/0176916 A1 | 6/2016 | Bradner et al. |
| 2016/0214972 A1 | 7/2016 | Jin et al. |
| 2016/0272639 A1 | 9/2016 | Crew et al. |
| 2016/0289216 A1* | 10/2016 | Jones .................. C07D 405/14 |
| 2017/0008904 A1 | 1/2017 | Crew et al. |
| 2017/0037004 A1 | 2/2017 | Crew et al. |
| 2017/0065719 A1 | 3/2017 | Qian et al. |
| 2018/0015087 A1 | 1/2018 | Liu et al. |
| 2018/0085465 A1 | 3/2018 | Bradner et al. |
| 2020/0207733 A1 | 7/2020 | Norcross et al. |
| 2020/0207783 A1 | 7/2020 | Norcross et al. |
| 2021/0009559 A1 | 1/2021 | Henderson et al. |
| 2021/0032245 A1 | 2/2021 | Nasveschuk et al. |
| 2021/0070763 A1 | 3/2021 | Nasveschuk et al. |
| 2021/0198256 A1 | 7/2021 | Nasveschuk et al. |
| 2022/0098194 A1 | 3/2022 | Nasveschuk et al. |
| 2022/0251061 A1 | 8/2022 | Phillips et al. |
| 2022/0289738 A1 | 9/2022 | Norcross et al. |
| 2022/0313826 A1 | 10/2022 | Phillips et al. |
| 2022/0313827 A1 | 10/2022 | Phillips et al. |

FOREIGN PATENT DOCUMENTS

| | | |
|---|---|---|
| EP | 0011092 A1 | 5/1980 |
| EP | 145010 A2 | 7/2009 |
| EP | 275888 A2 | 12/2017 |
| JP | S6248679 A | 3/1987 |
| WO | WO 1998/011111 A1 | 3/1998 |
| WO | WO 2002/059106 A1 | 8/2002 |
| WO | WO 2006/071940 A2 | 6/2006 |
| WO | WO 2006/102557 A2 | 9/2006 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2008/122038 A1 | 10/2008 |
| WO | WO 2009/026107 A1 | 2/2009 |
| WO | WO 2009/042177 A1 | 4/2009 |
| WO | WO 2009/131687 A1 | 10/2009 |
| WO | WO 2009/139880 A1 | 11/2009 |
| WO | WO 2009/145899 A1 | 12/2009 |
| WO | WO 2010/053732 A1 | 5/2010 |
| WO | WO 2010/107485 A1 | 9/2010 |
| WO | WO 2011/097218 A1 | 8/2011 |
| WO | WO 2011/137089 A1 | 11/2011 |
| WO | WO 2011/143669 A2 | 11/2011 |
| WO | WO 2012/079022 A1 | 6/2012 |
| WO | WO 2012/178208 A2 | 12/2012 |
| WO | WO 2013/020557 A1 | 2/2013 |
| WO | WO 2013/059215 A1 | 4/2013 |
| WO | WO 2013/063560 A2 | 5/2013 |
| WO | WO 2013/106643 A2 | 7/2013 |
| WO | WO 2013/106646 A2 | 7/2013 |
| WO | WO 2013/149704 A1 | 10/2013 |
| WO | WO 2013/170147 A1 | 11/2013 |
| WO | WO 2014/145887 A1 | 9/2014 |
| WO | WO 2015/160845 A2 | 10/2015 |
| WO | WO 2016/011906 A1 | 1/2016 |
| WO | WO 2016/033100 A1 | 3/2016 |
| WO | WO 2016/065139 A1 | 4/2016 |
| WO | WO 2016/105518 A1 | 6/2016 |
| WO | WO 2016/146985 A1 | 9/2016 |
| WO | WO 2016/169989 A1 | 10/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/079267 A1 | 5/2017 |
| WO | WO 2017/117473 A1 | 7/2017 |
| WO | WO 2017/161119 A1 | 9/2017 |
| WO | WO 2017/176708 A1 | 10/2017 |
| WO | WO 2017/176957 A1 | 10/2017 |
| WO | WO 2017/176958 A1 | 10/2017 |
| WO | WO 2017/180417 A1 | 10/2017 |
| WO | WO 2017/197240 A1 | 11/2017 |
| WO | WO 2017/201069 A1 | 11/2017 |
| WO | WO 2017/201449 A1 | 11/2017 |
| WO | WO 2017/223452 A1 | 12/2017 |
| WO | WO 2018/023029 A1 | 2/2018 |
| WO | WO 2018/051107 A1 | 3/2018 |
| WO | WO 2018/052945 A1 | 3/2018 |
| WO | WO 2018/052949 A1 | 3/2018 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/183411 A1 | 10/2018 |
| WO | WO 2018/189554 A1 | 10/2018 |
| WO | WO 2018/191199 A1 | 10/2018 |

OTHER PUBLICATIONS

U.S. Appl. No. 17/843,769, Nasveschuk et al., filed Jun. 17, 2022.
U.S. Appl. No. 17/351,935, Phillips et al., filed Jun. 18, 2021.
U.S. Appl. No. 17/465,583, Nasveschuk et al., filed Sep. 2, 2021.
U.S. Appl. No. 17/524,558, Phillips et al., filed Nov. 11, 2021.
U.S. Appl. No. 17/723,199, Henderson et al., filed Apr. 18, 2022.
U.S. Appl. No. 17/959,144, Phillips et al., filed Oct. 3, 2022.
U.S. Appl. No. 17/901,775, Nasveschuk et al., filed Sep. 22, 2022.
Agafonov Roman et al., Poster Presentation titled "Quantitative and high throughput method for measuring complex formation between target proteins and E3 ubiquitin ligase", EMBO, Sep. 16, 2017.
Bartlett, et al. "The evolution of thalidomide and its IMiD derivatives as anticancer agents." Nat Rev Cancer 2004, 4(4):312-322.
Berndsen et al. "New insights into ubiquitin E3 ligase mechanism" Nat. Struct. Mol. Biol. 2014, 21:301-307.
Bondeson et al. "Catalytic in vivo protein knockdown by small-molecule PROTACs" Nature Chemical Biology 2015, 11:611-617.
Buckley et al. "HaloPROTACS: Use of Small Molecule PROTACS to Induce Degradation of HaloTag Fusion Proteins" ACS Chemical Biology 2015, 10:1831-1837.
Buckley et al. "Small-Molecule Control of Intracellular Protein Levels through Modulation of the Ubiquitin Proteasome System" Angewandte Reviews, 2014, 53:2312-2330.
Buckley et al. "Targeting the Von Hippel-Lindau E3 Ubiquitin Ligase Using Small Molecules to Disrupt the Vhl/Hif-1alpha Interaction" J. Am. Chem. Soc. 2012, 134:4465-4468.
Burkhard et al. "Synthesis and Stability of Oxetane Analogs of Thalidomide and Lenalidomide" Organic Letters 2013, 15(7):4312-4315.
Chamberlain et al. "Structure of the human cereblon-DDB1-lenalidomide complex reveals basis for responsiveness to thalidomide analogs" Nature Structural and Molecule Biology, 2014, 21(9):803-809.
Chang, X. and Stewart, K. A. "What is the functional role of the thalidomide binding protein cereblon?" Int J Biochem Mol Bio. 2011, 2(3):287-294.
Collins et al., "Chemical approaches to targeted protein degradation through modulation of the ubiquitin-protease pathway", Biochem. J. 2017, 474(7), 1127-1147.
Contino-Pepin, et al., "Preliminary biological evaluations of new thalidomide analogues for multiple sclerosis application", Bioorganic & Medicinal Chemistry Letters, 2009, 19(3), 878-881.
Corson et al. "Design and applications of bifunctional small molecules: Why two heads are better than one" ACS Chemical Biology 2008, 3(11): 677-692.

(56) References Cited

OTHER PUBLICATIONS

Crews, C. M. "Targeting the undruggable proteome: the small molecules of my dreams" Chemistry and Biology 2010, 17(6):551-555.
Database registry chemical abstracts service, Jan. 12, 2014, XP002778332; STN database accession No. 1517829-18-3.
Database registry chemical abstracts service, Sep. 4, 2011, XP002778333; STN database accession No. 1327633-84-0.
Deshaies et al. "Ring domain E3 ubiquitin ligases." Ann. Rev. Biochem. 2009, 78:399-434.
Elam W.A., et al., Poster Presentation titled "Application of Biophysical Techniques to the Targeted Protein Degradation Therapeutic Strategy", Sep. 24, 2017.
Faden et al. "Generic tools for conditionally altering protein abundance and phenotypes on domain" Biol. Chem. 2014, 395(7-8):737-762.
Fisher, Stewart L., et al.; "Targeted protein degradation and the enzymology of degraders," Elsevier, Chemical Biology, 2018, 44:47-55.
Fischer et al. "Structure of the DDB1-CRBN E3 ubiquitin ligase in complex with thalidomide" Nature 2014, 512:49-53.
Fischer et al. "The Molecular Basis of CRL4DDB2/CSA Ubiquitin Ligase Architecture, Targeting, and Activation," Cell 2011, 147:1024-1039.
Gosink et al. "Redirecting the Specificity of Ubiquitination by Modifying Ubiquitin-Conjugating Enzymes" Proc. Natl. Acad. Sci. USA 1995, 92:9117-9121.
Gustafson et al. "Small-Molecule-Mediated Degradation of the Androgen Receptor through Hydrophobic Tagging" Angewandte Chemie 2015, 54:9659-9662.
Hines et al. "Posttranslational protein knockdown couple to receptor tyrosine kinase activation with phosphoPROTACs" PNAS 2013, 110(22):8942-8947.
International Written Opinion for PCT/EP2018/073555 mailed on Mar. 7, 2019.
Ito et al., "Identification of a Primary Target of thalidomide teratogenicity", Science, 2010, 327(5971), 1345-1350, XP0055062167.
Itoh et al. "Protein knockdown using methyl bestatin-ligand hybrid molecules: design and synthesis of inducers of ubiquitination-mediated degradation of cellular retinoic acid-binding proteins" Journal of the American Chemical Society 2010, 132(16), 5820-5826.
Jacques et al. "Differentiation of anti-inflammatory and antitumorigenic properties of stabilized enantiomers of thalidomide analogs" PNAS 2015, 112:E1471-E1479.
Kronke et al. "Lenalidomide Causes Selective Degradation of IKZF1 and IKZF3 in Multiple Myeloma Cells" Science 2014, 343(6168):301-305.
Kronke et al. "Lenalidomide induces ubiquitination and degradation of CDK1[alpha] in del(5q) MDS" Nature 2015, 523(7559):183-188.
Lai et al. "Modular PROTAC Design for the Degradation of Oncogenic BCR-ABL" Angewandte Chemie International Edition 2016, 55:807-810.
Lee et al. "Targeted Degradation of the Aryl Hydrocarbon Receptor by the PROTAC Approach: A Useful Chemical Genetic Tool" ChemBioChem 2007, 8:2058-2062.
Liu et al. "Design and biological characterization of hybrid compounds of curcumin and thalidomide for multiple myeloma" Organic and Biomolecular Chemistry 2013, 11:4757.
Lu et al. "Hijacking the E3 Ubiquitin Ligase Cereblon to Efficiently Target BRD4" Chemistry and Biology 2015, 22(6):755-763.
Lu et al. "The myeloma drug lenalidomide promotes the cereblon-dependent destruction of Ikaros proteins" Science 2014, 343:305-309.
Nasveschuk C., Presentation titled "Advances in the Medicinal Chemistry of Targeted Protein Degradation", Aug. 7, 2018.
Nawaz et al. "Proteasome-Dependent Degradation of the Human Estrogen Receptor" Proc. Natl. Acad. Sci. USA 1999, 96:1858-1862.
Neklesa et al. "Small-molecule hydrophobic tagging-induced degradation of HaloTag fusion proteins." Nat Chem Biol 2011, 7(8):538-543.
Patel, J., Poster Presentation titled "Diverse Utility of Targeted Protein Degradation at C4 Therapeutics", Sep. 17, 2017.
Phillips A., Presentation titled "Targeted Protein Degradation", Applied Pharmaceutical Chemistry, Cambridge, MA. Apr. 5, 2018.
Raina et al. "Chemical Inducers of Targeted Protein Degradation" Journal of Biological Chemistry 2010, 285:11057-11060.
Rodriguez-Gonzalez et al. "Targeting steroid hormone receptors for ubiquitination and degradation in breast and prostate cancer" Oncogene 2008, 27:7201-7211.
Ruchelman et al. "Isosteric analogs of lenalidomide and pomalidomide: Synthesis and biological activity" Bioorganic and Medicinal Chemistry Letters 2012, 23:360-365.
Sakamoto et al. "Development of Protacs to Target Cancer-Promoting Proteins for Ubiquitination and Degradation" Molecular and Cellular Proteomics 2003, 2(12):1350-1357.
Sakamoto et al. "Protacs: chimeric molecules that target proteins to the Skp1-Cullin-F box complex for ubiquitination and degradation" PNAS 2001, 98(15):8554-8559.
Schneekloth et al. "Chemical approaches to controlling intracellular protein degradation" Chembiochem 2005, 6(1):40-46.
Schneekloth et al. "Chemical Genetic Control of Protein Levels: Selective in Vivo Targeted Degradation" Journal of the American Chemical Society 2004, 126(12):3748-3754.
Schneekloth et al. "Targeted Intracellular Protein Degradation Induced by a Small Molecule: En Route to Chemical Proteomics" Bioorganic and Medicinal Chemistry Letters 2008, 18:5904-5908.
Shoji, et al., "Modified DNA Aptamer That Binds the (R)-Isomer of a Thalidomide Derivative with High Enantioselectivity", J. Am. Chem. Soc., 2007, 129, 1456-1464.
Smith et al. "Targeted Intracellular Protein Degradation Induced by a Small Molecule: En Route to Chemical Proteomics" Bioorg. Med. Chem. Lett. 2008, 18(22):5904-5908.
Spratt et al. "RBR E3 ubiquitin ligases: new structures, new insights, new questions." Biochem. 2014, 458:421-437.
Toure et al. "Small-Molecule PROTACs: New Approaches to Protein Degradation" Angewandte Chemie International Edition 2016, 55:1966-1973.
Vassilev et al. "In Vivo Activation of the P53 Pathway by Small-Molecule Antagonists of MDM2" Science 2004, 303:844-848.
Vieux Ellen et al., Poster Presentation titled "Measuring Small Molecule Induced Ubiquitination of Proteins", EMBO, Sep. 18, 2017.
Wang et al. "Roles of F-box proteins in cancer." Nat. Rev. Cancer 2014, 14:233-347.
Winter et al. "Phthalimide conjugation as a strategy for in vivo target protein degradation" Science 2015, 348(6241):1376-1381.
Zeid Rhamy Presentation titled "Targeted protein degradation as a novel therapeutic approach", Gordon Research Conference, Jun. 26, 2017.
Zengerle et al. "Selective Small Molecule Induced Degradation of the BET Bromodomain Protein BRD4" ACS Chem. Biol. 2015, 10:1770-1777.
Zhou et al. "Harnessing the Ubiquitination Machinery to Target the Degradation of Specific Cellular Proteins" Molecular Cell 2000, 6:751-756.

* cited by examiner

| Cmpds (µM) | A | B |
|---|---|---|
| DMSO | 68.4 | 66.1 |
| 0.0025 | 61 | 66.1 |
| 0.008 | 63.5 | 66.1 |
| 0.025 | 58.4 | 66.1 |
| 0.08 | 55.8 | 63.5 |
| 0.25 | 53.2 | 61 |
| 0.8 | 48.1 | 58.4 |
| 2.5 | 53.2 | 53.2 |
| 8 | 55.8 | 50.6 |
| 25 | 55.8 | 50.6 |

DIHYDROQUINOLINONES FOR MEDICAL TREATMENT

CROSS-REFERENCE TO RELATED APPLICATIONS

This application is a continuation of U.S. patent application Ser. No. 16/809,345, filed Mar. 4, 2020, which is a continuation of International Application No. PCT/EP2018/073555, filed Sep. 3, 2018, which claims the benefit of priority to European Patent Application No. 17189229.2, filed Sep. 4, 2017. The entirety of each of these applications is hereby incorporated by reference herein for all purposes.

FIELD OF THE INVENTION

The present invention provides dihydroquinolinone compounds which bind to the ubiquitously expressed E3 ligase protein cereblon (CRBN) and alter the substrate specificity of the CRBN E3 ubiquitin ligase complex, resulting in breakdown of intrinsic downstream proteins. The disclosed compounds are useful for the treatment of cancer.

BACKGROUND OF THE INVENTION

The field of targeted protein degradation promoted by small molecules has been intensively studied over the last years (Collins et al. Biochem. J. 2017, 474(7), 1127-47).

Protein degradation plays a role in various cellular functions, i.e. the concentrations of regulatory proteins are adjusted through degradation into small peptides to maintain health and productivity of the cells.

Cereblon is a protein that forms an E3 ubiquitin ligase complex, which ubiquinates various other proteins. Cereblon is known as primary target for anticancer thalidomide analogs. A higher expression of cereblon has been linked to the efficiency of thalidomide analogs in cancer therapy.

US200300008832, WO2016033100, WO2009131687, WO2013149704, U.S. Pat. No. 7,235,562, EP145010, EP275888 and WO2009026107 describe certain dihydroquinolone derivatives.

In recent years, a few bifunctional compounds have been described as useful modulators of targeted ubiquitination, e.g. WO2013020557, WO2013063560, WO2013106643, WO2015160845, WO2016011906, WO2016105518, WO2017007612, WO2017024318, and WO2017117473.

However, there is still an ongoing need for effective treatment of cancers.

SUMMARY OF THE INVENTION

The present invention provides dihydroquinolinones of formula A, or a pharmaceutically acceptable salt thereof,

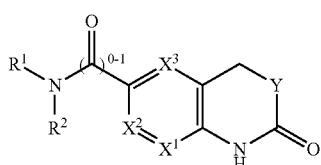

A wherein the substituents and variables are as described below and in the claims, or a pharmaceutically acceptable salt thereof.

The present compounds are useful for the therapeutic and/or prophylactic treatment of cancer.

The compounds of present invention can further be used as part of bifunctional compounds that comprise the compounds of present invention as E3 Ubiquitin Ligase moiety that is linked to a moiety that binds to a target protein where the target protein is proximate to the ubiquitin ligase to effect degradation of said protein.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of cancer.

The following definitions of the general terms used in the present description apply irrespectively of whether the terms in question appear alone or in combination with other groups.

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

The term "amino", alone or in combination with other groups, refers to $NH_2$.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. Examples are methyl and isopropyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like.

The term "hydroxy-$C_{1-6}$-alkyl", alone or in combination with other groups, refers to $C_{1-6}$-alkyl as defined herein, which is substituted by one or multiple hydroxy, particularly by 1 hydroxy. Examples are —$CH_2OH$, —$CH_2CH_2OH$ and the like.

The term "hydroxy", alone or in combination with other groups, refers to OH.

The term "halogen", alone or in combination with other groups, denotes chloro (Cl), iodo (I), fluoro (F) and bromo (Br). A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in which group at least one heterocyclic ring is aromatic. Examples are imidazolyl, quinolinyl, 1,2,3,4-tetrahydroquinolinyl, 2,3-dihydro-1H-pyrrolo[2,3-b]pyridinyl, benzimidazolyl, 1H-pyrazolyl, indolinyl, pyridinyl and the like.

The term "heterocycloalkyl" or "heterocyclyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, piperidyl, tetrahydropyridinyl, or dihydropyranyl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. A specific group is methoxy.

The term "aryl" denotes a monovalent aromatic carbocyclic mono- or bicyclic ring system comprising 6 to 10 carbon ring atoms. An example is phenyl.

Terms like "a-b-x substituted by R" means that the "x" portion of the moiety is substituted by R.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC-Compendium of Chemical Terminology, 2nd Edition, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

E1 Present invention relates to a compound of formula A, or a pharmaceutically acceptable salt thereof,

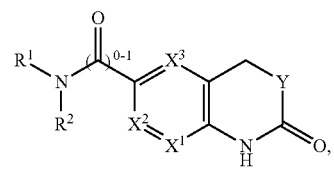

A wherein
Y is $CH_2$ or NH, in particular $CH_2$,
$X^1$ is CH or N,
$X^2$ is CH or N,
$X^3$ is CH or N,
and if one of $X^1$, $X^2$ or $X^3$ is N, then the other two are CH,
$R^1$ is each individually selected from the group consisting of
  i) —C(=O)—$R^6$,
  ii) heterocycyl,
  iii) heterocyclyl, substituted by 1-2 substituents individually selected from $R^{10}$ iv) aryl, and
v) aryl, substituted by 1-2 substituents individually selected from $R^9$;

$R^2$ is H, or $R^1$ and $R^2$ together with the nitrogen they are attached to form a heteroaryl, which can be substituted by 1-2 substituents individually selected from $R^3$, $R^3$ is each individually selected from the group consisting of
  i) —$(CH_2)_{0-1}$-aryl substituted by 1-2 substituents selected from $R^4$,
  ii) —$(CH_2)_{0-1}$-aryl,
  iii) —$(CH_2)_{0-1}$—$C_{3-7}$cycloalkyl-aryl,
  iv) —$(CH_2)_{0-2}$—$N(R^{3c})C(=O)$—$C_{1-6}$alkyl
  v) —$(CH_2)_{0-2}$—$N(R^{3c})C(=O)$—$C_{3-7}$cycloalkyl
  vi) amino-$C_{1-6}$alkyl,
  vii) —$C(=O)N(R^{3a},R^{3b})$,
  viii) —$C(=O)O$—$C_{1-6}$alkyl,
  ix) —$C_{1-6}$alkyl,
  x) —$C_{3-7}$cycloalkyl,
  xi) —$CH_2$—O—$(CH_2)_{0-1}$-aryl,
  xii) heteroaryl substituted by 1-2 substituents selected from $R^4$,
  xiii) hydroxy-$C_{1-6}$alkyl, and
  xiv) unsubstituted heteroaryl, $R^{3a}$ is selected from the group consisting of
  i) H, and
  ii) $C_{1-6}$alkyl, $R^{3b}$ is selected from the group consisting of
  i) H,
  ii) $C_{1-6}$alkyl, and
  iii) —$C_{3-7}$cycloalkyl, or $R^{3a}$ and $R^{3b}$ form together with the nitrogen they are attached to a heterocycloalkyl, $R^{3c}$ is selected from the group consisting of
  i) H, and
  ii) $C_{1-6}$alkyl, $R^4$ is selected from the group consisting of
  i) amino,
  ii) —$(CH_2)_{0-2}$—$N(R^{3c})C(=O)$—$C_{1-6}$alkyl,
  iii) —$C(=O)$—$C_{1-6}$alkyl,
  iv) —$C(=O)N(R^{3a},R^{3b})$,
  v) —$C(=O)O$—$C_{1-6}$alkyl,
  vi) $C_{1-6}$alkoxy,
  vii) $C_{1-6}$alkyl,
  viii) halo-$C_{1-6}$alkyl,
  ix) heteroaryl substituted by 1-2 substituents selected from $R^5$,
  x) hydroxy-$C_{1-6}$alkyl, and
  xi) unsubstituted heteroaryl, $R^5$ is $C_{1-6}$alkyl, $R^6$ is selected from the group consisting of
  i) unsubstituted aryl,
  ii) unsubstituted heteroaryl, and
  iii) heteroaryl substituted by 1-2 substituents selected from $R^7$, $R^7$ is selected from the group consisting of
  i) unsubstituted heteroaryl, and
  ii) heteroaryl substituted by 1-2 substituents selected from $R^8$, $R^8$ is $C_{1-6}$alkyl, $R^9$ is selected from the group consisting of
  i) $C_{1-6}$alkyl, and
  ii) —$C(=O)O$—$C_{1-6}$alkyl, $R^{10}$ is selected from the group consisting of
  i) $C_{1-6}$alkyl, and
  ii) —$C(=O)O$—$C_{1-6}$alkyl, for use in the therapeutic and/or prophylactic treatment of cancer.

E2 A certain embodiment of the invention relates to the compound of formula I as described herein for use in the therapeutic and/or prophylactic treatment of cancer, or a pharmaceutically acceptable salt thereof, wherein Y is $CH_2$.

E3 A certain embodiment of the invention relates to the compound of formula I as described herein, or a pharmaceutically acceptable salt thereof, for use in the therapeutic and/or prophylactic treatment of cancer

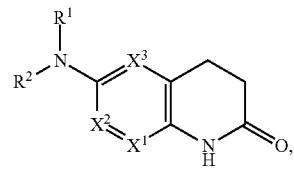

I wherein
$X^1$ is CH or N,
$X^2$ is CH or N,
$X^3$ is CH or N,
and if one of $X^1$, $X^2$ or $X^3$ is N, then the other two are CH, $R^1$ is each individually selected from the group consisting of
  i) —$C(=O)$—$R^6$,
  ii) heterocycyl,
  iii) heteocyclyl, substituted by 1-2 substituents individually selected from $R^{10}$
  iv) aryl, and
  v) aryl, substituted by 1-2 substituents individually selected from $R^9$;

$R^2$ is H, or $R^1$ and $R^2$ together with the nitrogen they are attached to form a heteroaryl, which can be substituted by 1-2 substituents individually selected from $R^3$, $R^3$ is each individually selected from the group consisting of
  i) —$(CH_2)_{0-1}$-aryl substituted by 1-2 substituents selected from $R^4$,
  ii) —$(CH_2)_{0-1}$-aryl,
  iii) —$(CH_2)_{0-1}$—$C_{3-7}$cycloalkyl-aryl,
  iv) —$(CH_2)_{0-2}$—$N(R^{3c})C(=O)$—$C_{1-6}$alkyl
  v) —$(CH_2)_{0-2}$—$N(R^{3c})C(=O)$—$C_{3-7}$cycloalkyl
  vi) amino-$C_{1-6}$alkyl,
  vii) —$C(=O)N(R^{3a},R^{3b})$,
  viii) —$C(=O)O$—$C_{1-6}$alkyl,
  ix) —$C_{1-6}$alkyl,
  x) —$C_{3-7}$cycloalkyl,
  xi) —$CH_2$—O—$(CH_2)_{0-1}$-aryl,
  xii) heteroaryl substituted by 1-2 substituents selected from $R^4$,
  xiii) hydroxy-$C_{1-6}$alkyl, and
  xiv) unsubstituted heteroaryl, $R^{3a}$ is selected from the group consisting of
  i) H, and
  i) $C_{1-6}$alkyl, $R^{3b}$ is selected from the group consisting of
  i) H,
  ii) $C_{1-6}$alkyl, and
  iii) —$C_{3-7}$cycloalkyl, or $R^{3a}$ and $R^{3b}$ form together with the nitrogen they are attached to a heterocycloalkyl, $R^{3c}$ is selected from the group consisting of
i) H, and
ii) $C_{1-6}$alkyl, $R^4$ is selected from the group consisting of
i) amino,
ii) —$(CH_2)_{0-2}$—$N(R^{3c})C(=O)$—$C_{1-6}$alkyl,
iii) —$C(=O)$—$C_{1-6}$alkyl,
iv) —$C(=O)N(R^{3a},R^{3b})$,
v) —$C(=O)O$—$C_{1-6}$alkyl,
vi) $C_{1-6}$alkoxy,
vii) $C_{1-6}$alkyl,
viii) halo-$C_{1-6}$alkyl,
ix) heteroaryl substituted by 1-2 substituents selected from $R^5$,
x) hydroxy-$C_{1-6}$alkyl, and
xi) unsubstituted heteroaryl, $R^5$ is $C_{1-6}$alkyl, $R^6$ is selected from the group consisting of
i) unsubstituted aryl,
ii) unsubstituted heteroaryl, and
iii) heteroaryl substituted by 1-2 substituents selected from $R^7$, $R^7$ is selected from the group consisting of
i) unsubstituted heteroaryl, and
ii) heteroaryl substituted by 1-2 substituents selected from $R^8$, $R^8$ is $C_{1-6}$alkyl, $R^9$ is selected from the group consisting of
i) $C_{1-6}$alkyl, and
ii) —$C(=O)O$—$C_{1-6}$alkyl, $R^{10}$ is selected from the group consisting of
i) $C_{1-6}$alkyl, and
ii) —$C(=O)O$—$C_{1-6}$alkyl, for use in the therapeutic and/or prophylactic treatment of cancer.

E4 A certain embodiment of the invention relates to the compound of formula I as described herein, or a pharmaceutically acceptable salt thereof,

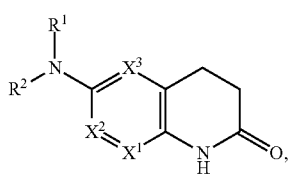

I wherein
$X^1$ is CH or N,
$X^2$ is CH or N,
$X^3$ is CH or N,
and if one of $X^1$, $X^2$ or $X^3$ is N, then the other two are CH,
$R^1$ is -$C(=O)$—$R^6$,
$R^2$ is H,
or $R^1$ and $R^2$ together with the nitrogen they are attached to form a heteroaryl, which can be substituted by 1-2 substituents individually selected from $R^3$,
$R^3$ is each individually selected from the group consisting of
i) —$(CH_2)_{0-1}$-aryl substituted by 1-2 substituents selected from $R^4$,
ii) —$(CH_2)_{0-1}$-aryl,
iii) —$C(=O)N(R^{3a},R^{3b})$,
iv) —$(CH_2)_{0-2}$—$N(R^{3c})C(=O)$—$C_{3-7}$cycloalkyl
v) —$(CH_2)_{0-2}$—$N(R^{3c})C(=O)$—$C_{1-6}$alkyl vi) —$C(=O)O$—$C_{1-6}$alkyl,
vii) —$(CH_2)_{0-1}$—$C_{3-7}$cycloalkyl-aryl,
viii) —$C_{1-6}$alkyl,
ix) —$C_{3-7}$cycloalkyl,
x) —$CH_2$—O—$(CH_2)_{0-1}$-aryl,
xi) heteroaryl substituted by 1-2 substituents selected from $R^4$,
xii) hydroxy-$C_{1-6}$alkyl, and
xiii) unsubstituted heteroaryl, $R^{3a}$ is selected from the group consisting of
i) H, and
ii) $C_{1-6}$alkyl, $R^{3b}$ is selected from the group consisting of
i) H,
ii) $C_{1-6}$alkyl, and
iii) —$C_{3-7}$cycloalkyl,
or $R^{3a}$ and $R^{3b}$ form together with the nitrogen they are attached to a heterocycloalkyl, $R^{3c}$ is selected from the group consisting of
i) H, and
ii) $C_{1-6}$alkyl, $R^4$ is selected from the group consisting of
i) unsubstituted heteroaryl,
ii) heteroaryl substituted by 1-2 substituents selected from $R^5$, and
iii) $C_{1-6}$alkoxy, $R^5$ is $C_{1-6}$alkyl, $R^6$ is selected from the group consisting of
i) unsubstituted heteroaryl, and
ii) heteroaryl substituted by 1-2 substituents selected from $R^7$, $R^7$ is selected from the group consisting of
i) unsubstituted heteroaryl, and
ii) heteroaryl substituted by 1-2 substituents selected from $R^8$, $R^8$ is $C_{1-6}$alkyl, for use in the therapeutic and/or prophylactic treatment of cancer.

E5 A certain embodiment of the invention relates to the compound of formula I as described herein, or a pharmaceutically acceptable salt thereof, wherein
$R^3$ is each individually selected from the group consisting of
i) —$(CH_2)_{0-1}$-aryl substituted by 1-2 substituents selected from $R^4$,
ii) —$(CH_2)_{0-1}$-aryl,
iii) —$(CH_2)_{0-1}$—$C_{3-7}$cycloalkyl-aryl,
iv) —$(CH_2)_{0-2}$—$N(R^{3c})C(=O)$—$C_{1-6}$alkyl
v) —$(CH_2)_{0-2}$—$N(R^{3c})C(=O)$—$C_{3-7}$cycloalkyl
vi) amino-$C_{1-6}$alkyl,
vii) —$C(=O)N(R^{3a},R^{3b})$,
viii) —$C(=O)O$—$C_{1-6}$alkyl,
ix) —$C_{1-6}$alkyl,
x) —$C_{3-7}$cycloalkyl,
xi) —$CH_2$—O—$(CH_2)_{0-1}$-aryl,
xii) heteroaryl substituted by 1-2 substituents selected from $R^4$,
xiii) hydroxy-$C_{1-6}$alkyl, and
xiv) unsubstituted heteroaryl, for use in the therapeutic and/or prophylactic treatment of cancer.

E6 A certain embodiment of the invention relates to the compound of formula I as described herein, or a pharmaceutically acceptable salt thereof, wherein
$R^3$ is each individually selected from the group consisting of
i) H,
ii) —$C(=O)C_{1-6}$alkyl iii) —C(=O)—N(R⁹',R¹⁰'),
iv) —C(=O)OC$_{1-6}$alkyl,
v) —C$_{1-6}$alkoxy,
vi) —C$_{1-6}$alkyl,
vii) —C$_{1-6}$alkyl-N(R¹¹)—C(=O)—R¹²,
viii) -halogen,
ix) -halogen-C$_{1-6}$alkyl,
x) -hydroxy-C$_{1-6}$alkyl,
xi) —N(R⁹',R¹⁰'), and
xii) —NH—C(=O)C$_{1-6}$alkyl,
wherein R⁹', R¹⁰', R¹¹ and R¹² are each independently selected from H and C$_{1-6}$alkyl,
for use in the therapeutic and/or prophylactic treatment of cancer.

E7 A certain embodiment of the invention relates to the compound of formula I as described herein, or a pharmaceutically acceptable salt thereof, for use in the therapeutic and/or prophylactic treatment of cancer, wherein X¹, X² and X³ are CH.

E8 A certain embodiment of the invention relates to the compound of formula I as described herein, or a pharmaceutically acceptable salt thereof, for use in the therapeutic and/or prophylactic treatment of cancer, wherein X¹ is CH.

E9 A certain embodiment of the invention relates to the compound of formula I as described herein, or a pharmaceutically acceptable salt thereof, for use in the therapeutic and/or prophylactic treatment of cancer, wherein X² is CH.

E10 A certain embodiment of the invention relates to the compound of formula I as described herein, or a pharmaceutically acceptable salt thereof, for use in the therapeutic and/or prophylactic treatment of cancer, wherein X³ is CH.

E11 A certain embodiment of the invention relates to the compound of formula I as described herein, or a pharmaceutically acceptable salt thereof, for use in the therapeutic and/or prophylactic treatment of cancer, which compound is selected from the group consisting of (RS)—N-(7-oxo-5,6,7,8-tetrahydro-1,8-naphthyridin-3-yl)-1,2,3,4-tetrahydronaphthalene-1-carboxamide,
2-((benzyloxy)methyl)-N-methyl-1-(2-oxo-1,2,3,4-tetrahydroquinolin-6-yl)-1H-benzo[d]imidazole-5-carboxamide,
2-(2-(cyclopropanecarboxamido)ethyl)-N-methyl-1-(2-oxo-1,2,3,4-tetrahydroquinolin-6-yl)-1H-benzo[d]imidazole-5-carboxamide,
2-(2-acetamidophenyl)-N-methyl-1-(2-oxo-3,4-dihydro-1H-quinolin-6-yl)benzimidazole-5-carboxamide,
2-(2-acetyl-3-pyridyl)-N-methyl-1-(2-oxo-3,4-dihydro-1H-quinolin-6-yl)benzimidazole-5-carboxamide,
2-(2-acetylphenyl)-N-methyl-1-(2-oxo-3,4-dihydro-1H-quinolin-6-yl)benzimidazole-5-carboxamide,
2-(2-aminoethyl)-N-methyl-1-(2-oxo-1,2,3,4-tetrahydroquinolin-6-yl)-1H-benzo[d]imidazole-5-carboxamide,
2-(2-aminophenyl)-N-methyl-1-(2-oxo-3,4-dihydro-1H-quinolin-6-yl)benzimidazole-5-carboxamide,
2-(2-fluoro-5-methoxy-phenyl)-N-methyl-1-(2-oxo-3,4-dihydro-1H-quinolin-6-yl)benzimidazole-5-carboxamide,
2-(2-methoxy-4-pyridyl)-N-methyl-1-(7-oxo-6,8-dihydro-5H-1,8-naphthyridin-3-yl)benzimidazole-5-carboxamide,
2-(2-methoxybenzyl)-N-methyl-1-(2-oxo-1,2,3,4-tetrahydroquinolin-6-yl)-1H-benzo[d]imidazole-5-carboxamide,
2-(2-methoxypyridin-3-yl)-N-methyl-1-(2-oxo-1,2,3,4-tetrahydroquinolin-6-yl)-1H-benzo[d]imidazole-5-carboxamide,
2-(2-methoxypyridin-4-yl)-N-methyl-1-(2-oxo-1,2,3,4-tetrahydroquinolin-6-yl)-1H-benzo[d]imidazole-5-carboxamide,
2-(3-acetamido-2-pyridyl)-N-methyl-1-(2-oxo-3,4-dihydro-1H-quinolin-6-yl)benzimidazole-5-carboxamide,
2-(3-amino-2-pyridyl)-N-methyl-1-(2-oxo-3,4-dihydro-1H-quinolin-6-yl)benzimidazole-5-carboxamide,
2-(3-methoxyphenyl)-N-methyl-1-(2-oxo-3,4-dihydro-1H-quinolin-6-yl)benzimidazole-5-carboxamide,
2-(3-methylimidazol-4-yl)-N-(2-oxo-3,4-dihydro-1H-quinolin-6-yl)quinoline-4-carboxamide,
2-(4-methoxy-6-methyl-2-pyridyl)-N-methyl-1-(2-oxo-3,4-dihydro-1H-quinolin-6-yl)benzimidazole-5-carboxamide,
2-(4-methoxypyridin-2-yl)-N-methyl-1-(2-oxo-1,2,3,4-tetrahydroquinolin-6-yl)-1H-benzo[d]imidazole-5-carboxamide,
2-(5-fluoro-2-methoxy-4-pyridyl)-N-methyl-1-(2-oxo-3,4-dihydro-1H-quinolin-6-yl)benzimidazole-5-carboxamide,
2-(5-methoxy-2-methyl-phenyl)-N-methyl-1-(2-oxo-3,4-dihydro-1H-quinolin-6-yl)benzimidazole-5-carboxamide,
2-(6-methoxypyridin-2-yl)-N-methyl-1-(2-oxo-1,2,3,4-tetrahydroquinolin-6-yl)-1H-benzo[d]imidazole-5-carboxamide,
2-(6-methoxypyridin-3-yl)-N-methyl-1-(2-oxo-1,2,3,4-tetrahydroquinolin-6-yl)-1H-benzo[d]imidazole-5-carboxamide,
2-(hydroxymethyl)-N-methyl-1-(2-oxo-1,2,3,4-tetrahydroquinolin-6-yl)-1H-benzo[d]imidazole-5-carboxamide,
2-[[2-methoxy-4-(trifluoromethyl)phenyl]methyl]-N-methyl-1-(2-oxo-3,4-dihydro-1H-quinolin-6-yl)benzimidazole-5-carboxamide,
2-[2-(hydroxymethyl)-4-pyridyl]-N-methyl-1-(2-oxo-3,4-dihydro-1H-quinolin-6-yl)benzimidazole-5-carboxamide,
2-[2-(hydroxymethyl)phenyl]-N-methyl-1-(2-oxo-3,4-dihydro-1H-quinolin-6-yl)benzimidazole-5-carboxamide,
2-[4-(acetamidomethyl)phenyl]-N-methyl-1-(2-oxo-3,4-dihydro-1H-quinolin-6-yl)benzimidazole-5-carboxamide,
2-benzyl-N-methyl-1-(2-oxo-1,2,3,4-tetrahydroquinolin-6-yl)-1H-benzo[d]imidazole-5-carboxamide,
2-cyclopropyl-N-methyl-1-(2-oxo-1,2,3,4-tetrahydroquinolin-6-yl)-1H-benzo[d]imidazole-5-carboxamide,
2-ethyl-N-methyl-1-(2-oxo-3,4-dihydro-1H-quinolin-6-yl)benzimidazole-5-carboxamide,
2-isopropyl-N,N-dimethyl-1-(6-oxo-7,8-dihydro-5H-1,5-naphthyridin-2-yl)benzimidazole-5-carboxamide,
2-isopropyl-N-methyl-1-(2-oxo-1,2,3,4-tetrahydroquinazolin-6-yl)-1H-benzo[d]imidazole-5-carboxamide,
2-isopropyl-N-methyl-1-(6-oxo-7,8-dihydro-5H-1,5-naphthyridin-2-yl)benzimidazole-5-carboxamide,
2-isopropyl-N-methyl-1-(7-oxo-6,8-dihydro-5H-1,8-naphthyridin-3-yl)benzimidazole-5-carboxamide,
6-((2-aminophenyl)amino)-3,4-dihydroquinazolin-2(1H)-one,
6-(1H-imidazol-1-yl)-3,4-dihydro-1,8-naphthyridin-2(1H)-one,
6-(2,3-dihydropyrrolo[2,3-b]pyridine-1-carbonyl)-3,4-dihydro-1H-1,8-naphthyridin-2-one,
6-(2,3-dihydropyrrolo[2,3-b]pyridine-1-carbonyl)-3,4-dihydro-1H-quinolin-2-one,
6-(2-isopropyl-1H-benzo[d]imidazol-1-yl)-3,4-dihydroquinazolin-2(1H)-one,
6-(3,4-dihydro-2H-quinoline-1-carbonyl)-3,4-dihydro-1H-1,8-naphthyridin-2-one,
6-(3,4-dihydro-2H-quinoline-1-carbonyl)-3,4-dihydro-1H-quinolin-2-one,
6-(5-(4-methoxyphenyl)-1H-imidazol-1-yl)-3,4-dihydroquinolin-2(1H)-one, 6-(5-phenyl-1H-imidazol-1-yl)-3,4-dihydroquinolin-2(1H)-one,
6-(indoline-1-carbonyl)-3,4-dihydro-1H-1,8-naphthyridin-2-one,
6-(indoline-1-carbonyl)-3,4-dihydro-1H-quinolin-2-one,
7-(1H-imidazol-1-yl)-3,4-dihydroquinolin-2(1H)-one,
ethyl 5-(methylcarbamoyl)-1-(2-oxo-1,2,3,4-tetrahydroquinolin-6-yl)-1H-benzo[d]imidazole-2-carboxylate,
methyl 2-(2-methoxypyridin-4-yl)-1-(2-oxo-1,2,3,4-tetrahydroquinolin-6-yl)-1H-benzo[d]imidazole-5-carboxylate,
methyl 2-[[5-(methylcarbamoyl)-1-(2-oxo-3,4-dihydro-1H-quinolin-6-yl)benzimidazol-2-yl]methyl]benzoate,
methyl 2-[5-(methylcarbamoyl)-1-(2-oxo-3,4-dihydro-1H-quinolin-6-yl)benzimidazol-2-yl]pyridine-3-carboxylate,
methyl 2-isopropyl-1-(6-oxo-7,8-dihydro-5H-1,5-naphthyridin-2-yl)benzimidazole-5-carboxylate,
methyl 4-((2-oxo-1,2,3,4-tetrahydroquinolin-6-yl)amino)benzoate,
N-(1-acetyl-4-piperidyl)-2-oxo-3,4-dihydro-1H-quinoline-6-carboxamide,
N-methyl-1-(2-oxo-1,2,3,4-tetrahydroquinolin-6-yl)-2-(1H-pyrazol-4-yl)-1H-benzo[d]imidazole-5-carboxamide,
N-methyl-1-(2-oxo-1,2,3,4-tetrahydroquinolin-6-yl)-2-(1-phenylcyclopropyl)-1H-benzo[d]imidazole-5-carboxamide,
N-methyl-1-(2-oxo-1,2,3,4-tetrahydroquinolin-6-yl)-2-(quinolin-4-yl)-1H-benzo[d]imidazole-5-carboxamide,
N-methyl-1-(2-oxo-3,4-dihydro-1H-quinolin-6-yl)-2-[3-(trifluoromethyl)-4-pyridyl]benzimidazole-5-carboxamide,
N-methyl-2-(morpholine-4-carbonyl)-1-(2-oxo-1,2,3,4-tetrahydroquinolin-6-yl)-1H-benzo[d]imidazole-5-carboxamide,
N-methyl-2-[2-(3-methylimidazol-4-yl)-4-quinolyl]-1-(2-oxo-3,4-dihydro-1H-quinolin-6-yl)benzimidazole-5-carboxamide,
N-methyl-2-[3-(methylcarbamoyl)-2-pyridyl]-1-(2-oxo-3,4-dihydro-1H-quinolin-6-yl)benzimidazole-5-carboxamide, and
N-methyl-2-[2-(methylcarbamoyl)phenyl]-1-(2-oxo-3,4-dihydro-1H-quinolin-6-yl)benzimidazole-5-carboxamide.

E12 A certain embodiment of the invention relates to the compound of formula I as described herein, or a pharmaceutically acceptable salt thereof, for use in the therapeutic and/or prophylactic treatment of cancer, which compound is selected from the group consisting of
2-(2-(cyclopropanecarboxamido)ethyl)-N-methyl-1-(2-oxo-1,2,3,4-tetrahydroquinolin-6-yl)-1H-benzo[d]imidazole-5-carboxamide,
2-((benzyloxy)methyl)-N-methyl-1-(2-oxo-1,2,3,4-tetrahydroquinolin-6-yl)-1H-benzo[d]imidazole-5-carboxamide,
2-(2-methoxybenzyl)-N-methyl-1-(2-oxo-1,2,3,4-tetrahydroquinolin-6-yl)-1H-benzo[d]imidazole-5-carboxamide,
2-(2-methoxypyridin-4-yl)-N-methyl-1-(2-oxo-1,2,3,4-tetrahydroquinolin-6-yl)-1H-benzo[d]imidazole-5-carboxamide,
2-(hydroxymethyl)-N-methyl-1-(2-oxo-1,2,3,4-tetrahydroquinolin-6-yl)-1H-benzo[d]imidazole-5-carboxamide,
2-benzyl-N-methyl-1-(2-oxo-1,2,3,4-tetrahydroquinolin-6-yl)-1H-benzo[d]imidazole-5-carboxamide,
2-cyclopropyl-N-methyl-1-(2-oxo-1,2,3,4-tetrahydroquinolin-6-yl)-1H-benzo[d]imidazole-5-carboxamide,
ethyl 5-(methylcarbamoyl)-1-(2-oxo-1,2,3,4-tetrahydroquinolin-6-yl)-1H-benzo[d]imidazole-2-carboxylate,
N-methyl-1-(2-oxo-1,2,3,4-tetrahydroquinolin-6-yl)-2-(1H-pyrazol-4-yl)-1H-benzo[d]imidazole-5-carboxamide,
N-methyl-1-(2-oxo-1,2,3,4-tetrahydroquinolin-6-yl)-2-(1-phenylcyclopropyl)-1H-benzo[d]imidazole-5-carboxamide,
N-methyl-1-(2-oxo-1,2,3,4-tetrahydroquinolin-6-yl)-2-(quinolin-4-yl)-1H-benzo[d]imidazole-5-carboxamide,
2-(3-methylimidazol-4-yl)-N-(2-oxo-3,4-dihydro-1H-quinolin-6-yl)quinoline-4-carboxamide,
2-ethyl-N-methyl-1-(2-oxo-3,4-dihydro-1H-quinolin-6-yl)benzimidazole-5-carboxamide,
6-(5-phenyl-1H-imidazol-1-yl)-3,4-dihydroquinolin-2(1H)-one,
6-imidazol-1-yl-3,4-dihydro-1H-quinolin-2-one,
N-methyl-2-[2-(3-methylimidazol-4-yl)-4-quinolyl]-1-(2-oxo-3,4-dihydro-1H-quinolin-6-yl)benzimidazole-5-carboxamide, and
6-(1H-imidazol-1-yl)-3,4-dihydro-1,8-naphthyridin-2(1H)-one.

E13 A compound of formula I, or a pharmaceutically acceptable salt thereof,

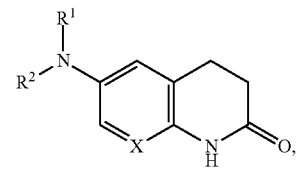

wherein
X is CH or N,
R$^1$ is-C(O)—R$^6$,
R$^2$ is H,
or R$^1$ and R$^2$ together with the nitrogen they are attached to form a heteroaryl, which can be substituted by 1-2 substituents selected from R$^3$,
R$^3$ is selected from the group consisting of
  i) —(CH$_2$)$_{0-1}$-aryl substituted by 1-2 substituents selected from R$^4$
  ii) —(CH$_2$)$_{0-1}$-aryl,
  iii) —C(=O)N(R$^{3a}$,R$^{3b}$),
  iv) —C(=O)O—C$_{1-6}$alkyl,
  v) —C(C$_{3-7}$cycloalkyl)-aryl
  vi) C$_{1-6}$alkyl,
  vii) —C$_{3-7}$cycloalkyl
  viii) —CH$_2$—O—(CH$_2$)$_{0-1}$-aryl,
  ix) heteroaryl substituted by 1-2 substituents selected from R$^4$,
  x) hydroxy-C$_{1-6}$alkyl, and
  xi) unsubstituted heteroaryl,
R$^{3a}$ is selected from the group consisting of
  i) H, and
  ii) C$_{1-6}$alkyl,
R$^{3b}$ is selected from the group consisting of
  i) H,
  ii) C$_{1-6}$alkyl, and
  iii) —C$_{3-7}$cycloalkyl
or R$^{3a}$ and R$^{3b}$ form together with the nitrogen they are attached to a heterocycloalkyl,
R$^4$ is selected from the group consisting of
  i) unsubstituted heteroaryl,
  ii) heteroaryl substituted by 1-2 substituents selected from R5, and
  iii) C$_{1-6}$alkoxy
R$^5$ is C$_{1-6}$alkyl, R⁶ is selected from the group consisting of
i) unsubstituted heteroaryl, and
ii) heteroaryl substituted by 1-2 substituents selected from R⁷,
R⁷ is selected from the group consisting of
i) unsubstituted heteroaryl, and
ii) heteroaryl substituted by 1-2 substituents selected from R⁸,
R⁸ is C$_{1-6}$alkyl,
with the proviso that 6-imidazol-1-yl-3,4-dihydro-1H-quinolin-2-one is excluded.

E14 The compound according to any one of the embodiments, wherein X is CH.

E15 The compound according to any one of the embodiments, wherein R¹ and R² together with the nitrogen they are attached to form a heteroaryl, in particular an imidazolyl or benzimidazolyl, each of which can be substituted by 1-2 substituents individually selected from R³, wherein
R³ is each individually selected from the group consisting of
i) —(CH$_2$)$_{0-1}$-aryl substituted by 1-2 substituents selected from R⁴,
ii) —(CH$_2$)$_{0-1}$-aryl,
iii) —C(=O)N(R$^{3a}$,R$^{3b}$),
iv) —C(=O)O—C$_{1-6}$alkyl,
v) —C(C$_{3-7}$cycloalkyl)-aryl,
vi) C$_{1-6}$alkyl,
vii) —C$_{3-7}$cycloalkyl,
viii) —CH$_2$—O—(CH$_2$)$_{0-1}$-aryl,
ix) heteroaryl substituted by 1-2 substituents selected from R⁴,
x) hydroxy-C$_{1-6}$alkyl, and
xi) unsubstituted heteroaryl,
R$^{3a}$ is selected from the group consisting of
i) H, and
ii) C$_{1-6}$alkyl,
R$^{3b}$ is selected from the group consisting of
i) H,
ii) C$_{1-6}$alkyl, and
iii) —C$_{3-7}$cycloalkyl,
R⁴ is selected from the group consisting of
i) unsubstituted heteroaryl,
ii) heteroaryl substituted by 1-2 substituents selected from R⁵, and
iii) C$_{1-6}$alkoxy,
R⁵ is C$_{1-6}$alkyl.

E16 The compound according to any one of the embodiments, wherein R³ is selected from the group consisting of
i) 1H-pyrazolyl,
i) methylimidazolyl-quinolyl-,
iii) methoxybenzyl,
iv) methoxypyridinyl,
v) benzyl,
vi) —C(=O)N(H,Me),
vii) —C(=O)O-ethyl,
viii) —C(=O)N(H,cyclopropyl),
ix) —C(cyclopropyl)-phenyl,
x) —CH$_2$—CH$_2$OH, and
xi) —CH$_2$—O-benzyl,
xii) cyclopropyl,
xiii) ethyl,
xiv) phenyl, and
xv) quinolyl.

E17 The compound according to any one of the embodiments, wherein R³ is methylimidazolyl-quinolyl-.

E18 The compound according to any one of the embodiments, or a pharmaceutically acceptable salt thereof, that is selected from the group consisting of
2-(2-(cyclopropanecarboxamido)ethyl)-N-methyl-1-(2-oxo-1,2,3,4-tetrahydroquinolin-6-yl)-1H-benzo[d]imidazole-5-carboxamide,
2-((benzyloxy)methyl)-N-methyl-1-(2-oxo-1,2,3,4-tetrahydroquinolin-6-yl)-1H-benzo[d]imidazole-5-carboxamide,
2-(2-methoxybenzyl)-N-methyl-1-(2-oxo-1,2,3,4-tetrahydroquinolin-6-yl)-1H-benzo[d]imidazole-5-carboxamide,
2-(2-methoxypyridin-4-yl)-N-methyl-1-(2-oxo-1,2,3,4-tetrahydroquinolin-6-yl)-1H-benzo[d]imidazole-5-carboxamide,
2-(hydroxymethyl)-N-methyl-1-(2-oxo-1,2,3,4-tetrahydroquinolin-6-yl)-1H-benzo[d]imidazole-5-carboxamide,
2-benzyl-N-methyl-1-(2-oxo-1,2,3,4-tetrahydroquinolin-6-yl)-1H-benzo[d]imidazole-5-carboxamide,
2-cyclopropyl-N-methyl-1-(2-oxo-1,2,3,4-tetrahydroquinolin-6-yl)-1H-benzo[d]imidazole-5-carboxamide,
ethyl 5-(methylcarbamoyl)-1-(2-oxo-1,2,3,4-tetrahydroquinolin-6-yl)-1H-benzo[d]imidazole-2-carboxylate,
N-methyl-1-(2-oxo-1,2,3,4-tetrahydroquinolin-6-yl)-2-(1H-pyrazol-4-yl)-1H-benzo[d]imidazole-5-carboxamide,
N-methyl-1-(2-oxo-1,2,3,4-tetrahydroquinolin-6-yl)-2-(1-phenylcyclopropyl)-1H-benzo[d]imidazole-5-carboxamide,
N-methyl-1-(2-oxo-1,2,3,4-tetrahydroquinolin-6-yl)-2-(quinolin-4-yl)-1H-benzo[d]imidazole-5-carboxamide,
2-(3-methylimidazol-4-yl)-N-(2-oxo-3,4-dihydro-1H-quinolin-6-yl)quinoline-4-carboxamide,
2-ethyl-N-methyl-1-(2-oxo-3,4-dihydro-1H-quinolin-6-yl)benzimidazole-5-carboxamide,
6-(5-phenyl-1H-imidazol-1-yl)-3,4-dihydroquinolin-2(1H)-one,
6-imidazol-1-yl-3,4-dihydro-1H-quinolin-2-one, and
N-methyl-2-[2-(3-methylimidazol-4-yl)-4-quinolyl]-1-(2-oxo-3,4-dihydro-1H-quinolin-6-yl)benzimidazole-5-carboxamide.

E19 The compound of formula I according to any of the embodiments, which is a compound of formula II, or a pharmaceutically acceptable salt thereof,

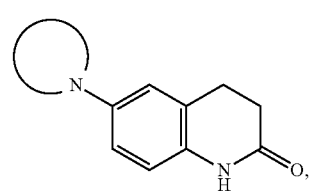

wherein
the ring is benzimidazolyl-5-carboximide, which can be substituted by 1-2 substituents selected from R³,
R³ is selected from the group consisting of
i) —(CH$_2$)$_{0-1}$-aryl substituted by 1-2 substituents selected from R⁴
ii) —(CH$_2$)$_{0-1}$-aryl,
iii) —C(=O)O—C$_{1-6}$alkyl,
iv) —C(C$_{3-7}$cycloalkyl)-aryl
v) C$_{1-6}$alkyl,
vi) —C$_{3-7}$cycloalkyl
vii) —CH$_2$—O—(CH$_2$)$_{0-1}$-aryl,
viii) —C(=O)N(H, cyclopropyl),
ix) heteroaryl substituted by 1-2 substituents selected from R⁴, x) hydroxy-$C_{1-6}$alkyl, and
xi) unsubstituted heteroaryl,
$R^4$ is selected from the group consisting of
i) unsubstituted heteroaryl,
ii) heteroaryl substituted by 1-2 substituents selected from $R^5$, and
iii) $C_{1-6}$alkoxy
$R^5$ is $C_{1-6}$alkyl.

E20 The compound of according to any of the embodiments, wherein $R^3$ is selected from the group consisting of
i) 1H-pyrazolyl,
ii) methylimidazolyl-quinolyl-,
iii) methoxybenzyl,
iv) methoxypyridinyl,
v) benzyl,
vi) —C(=O)N(H,cyclopropyl),
vii) —C(=O)O-ethyl.
viii) —C(cyclopropyl)-phenyl,
ix) —CH₂—CH₂OH, and
x) —CH₂—O-benzyl,
xi) cyclopropyl,
xii) ethyl, and
xiii) quinolyl.

E21 The compound according to any one of the embodiments, wherein $R^3$ is selected from the group consisting of
i) 1H-pyrazolyl,
ii) methylimidazolyl-quinolyl-,
iii) methoxybenzyl,
iv) methoxypyridinyl,
v) benzyl,
vi) —C(=O)O-ethyl.
vii) —C(cyclopropyl)-phenyl,
viii) —CH₂—CH₂OH, and
ix) —CH₂—O-benzyl,
x) cyclopropyl,
xi) ethyl,
xii) phenyl, and
xiii) quinolyl.

E22 The compound according to any one of the embodiments, wherein $R^3$ is methylimidazolyl-quinolyl-.

E23 The compound of formula I according to any one of the embodiments, or a pharmaceutically acceptable salt thereof, that is selected from the group consisting of
2-(2-(cyclopropanecarboxamido)ethyl)-N-methyl-1-(2-oxo-1,2,3,4-tetrahydroquinolin-6-yl)-1H-benzo[d]imidazole-5-carboxamide,
2-((benzyloxy)methyl)-N-methyl-1-(2-oxo-1,2,3,4-tetrahydroquinolin-6-yl)-1H-benzo[d]imidazole-5-carboxamide,
2-(2-methoxybenzyl)-N-methyl-1-(2-oxo-1,2,3,4-tetrahydroquinolin-6-yl)-1H-benzo[d]imidazole-5-carboxamide,
2-(2-methoxypyridin-4-yl)-N-methyl-1-(2-oxo-1,2,3,4-tetrahydroquinolin-6-yl)-1H-benzo[d]imidazole-5-carboxamide,
2-(hydroxymethyl)-N-methyl-1-(2-oxo-1,2,3,4-tetrahydroquinolin-6-yl)-1H-benzo[d]imidazole-5-carboxamide,
2-benzyl-N-methyl-1-(2-oxo-1,2,3,4-tetrahydroquinolin-6-yl)-1H-benzo[d]imidazole-5-carboxamide,
2-cyclopropyl-N-methyl-1-(2-oxo-1,2,3,4-tetrahydroquinolin-6-yl)-1H-benzo[d]imidazole-5-carboxamide,
ethyl 5-(methylcarbamoyl)-1-(2-oxo-1,2,3,4-tetrahydroquinolin-6-yl)-1H-benzo[d]imidazole-2-carboxylate,
N-methyl-1-(2-oxo-1,2,3,4-tetrahydroquinolin-6-yl)-2-(1H-pyrazol-4-yl)-1H-benzo[d]imidazole-5-carboxamide,
N-methyl-1-(2-oxo-1,2,3,4-tetrahydroquinolin-6-yl)-2-(1-phenylcyclopropyl)-1H-benzo[d]imidazole-5-carboxamide,
N-methyl-1-(2-oxo-1,2,3,4-tetrahydroquinolin-6-yl)-2-(quinolin-4-yl)-1H-benzo[d]imidazole-5-carboxamide,
2-ethyl-N-methyl-1-(2-oxo-3,4-dihydro-1H-quinolin-6-yl)benzimidazole-5-carboxamide,
6-imidazol-1-yl-3,4-dihydro-1H-quinolin-2-one, and
N-methyl-2-[2-(3-methylimidazol-4-yl)-4-quinolyl]-1-(2-oxo-3,4-dihydro-1H-quinolin-6-yl)benzimidazole-5-carboxamide.

E24 A compound, or pharmaceutically acceptable salts thereof, having a chemical structure comprising:

$$P\text{-}L\text{-}C$$

wherein
L is a linker group;
C is a compound of formula I according to any one of the embodiments,
  wherein L is chemically linked to C; and
P is a protein target moiety that binds to a target protein or a target polypeptide,
  wherein L is chemically linked to P.

E25 The compound according to any one of the embodiments, wherein L is selected from the group consisting of:
i) —NHCH₂—(CH₂)₁₋₃₀—CH₂NH—, and
ii) —NH—(CH₂CH₂O)₁₋₂₅—CH₂CH₂—NH—.

E26 The compound according to any one of the embodiments, wherein P is a BRD4 inhibitor, in particular wherein P is

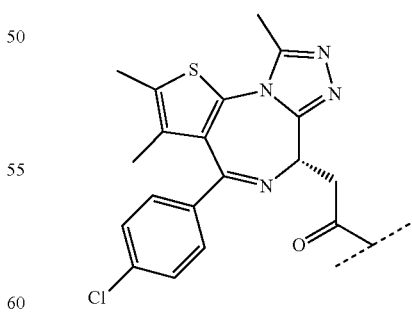

E27 The compound according to any one of the embodiments, selected from the group consisting of
N-(10-(2-(((6S)-4-(4-chlorophenyl)-2,3,9-trimethyl-6H-thieno[3,2-f][1,2,4]triazolo[4,3-a][1,4]diazepin-6-yl)acetamido)decyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide, N-(2-(2-(2-(2-(((6S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide, and N-(5-(2-(((6S)-4-(4-chlorophenyl)-2,3,9-trimethyl-6H-thieno[3,2-f][1,2,4]triazolo[4,3-a][1,4]diazepin-6-yl)acetamido)pentyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide.

E28 A certain embodiment of the invention relates to the compound of formula I as described herein, or a pharmaceutically acceptable salt thereof, for use as therapeutically active substance.

E29 A certain embodiment of the invention relates to the compound of formula I as described herein, or a pharmaceutically acceptable salt thereof, for the use in the therapeutic and/or prophylactic treatment of cancer.

E30 A certain embodiment of the invention relates to the compound of formula I as described herein, or a pharmaceutically acceptable salt thereof, for the manufacture of a medicament for the therapeutic and/or prophylactic treatment of cancer.

E31 A certain embodiment of the invention relates to a pharmaceutical composition comprising the compound of formula I as described herein, or a pharmaceutically acceptable salt thereof, and a pharmaceutically acceptable auxiliary substance.

E32 A certain embodiment of the invention relates to a method for the therapeutic and/or prophylactic treatment of cancer, by administering the compound of formula I as described herein, or a pharmaceutically acceptable salt thereof, to a patient.

E33 A certain embodiment of the invention relates to the compound of P-L-C as described herein, or a pharmaceutically acceptable salt thereof, for use as therapeutically active substance.

E34 A certain embodiment of the invention relates to the compound of P-L-C as described herein, or a pharmaceutically acceptable salt thereof, for the use in the therapeutic and/or prophylactic treatment of cancer.

E35 A certain embodiment of the invention relates to the compound of P-L-C as described herein, or a pharmaceutically acceptable salt thereof, for the manufacture of a medicament for the therapeutic and/or prophylactic treatment of cancer.

E36 A certain embodiment of the invention relates to a pharmaceutical composition comprising the compound of P-L-C as described herein, or a pharmaceutically acceptable salt thereof, and a pharmaceutically acceptable auxiliary substance, in particular an inert carrier.

E37 A certain embodiment of the invention relates to a method for the therapeutic and/or prophylactic treatment of cancer, by administering the compound of P-L-C as described herein, or a pharmaceutically acceptable salt thereof, to a patient.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I or formula P-L-C may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula A, I or formula P-L-C may be prepared in accordance with the schemes described in the examples. The starting material is commercially available or may be prepared in accordance with known methods.

The preparation of compounds of formula A or I of the present invention may be carried out in sequential or convergent synthetic routes. Syntheses of the compounds of the invention are shown in the following schemes 1-8 and in the description of 65 specific examples. The skills required for carrying out the reaction and purification of the resulting products are known to those skilled in the art. The substituents and indices used in the following description of the processes have the significance given herein before unless indicated to the contrary.

In more detail, the compounds of formula A or I can be manufactured by the methods given below, by the methods given in the examples or by analogous methods. Appropriate reaction conditions for the individual reaction steps are known to a person skilled in the art. The reaction sequence is not limited to the one displayed in schemes 1-8, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

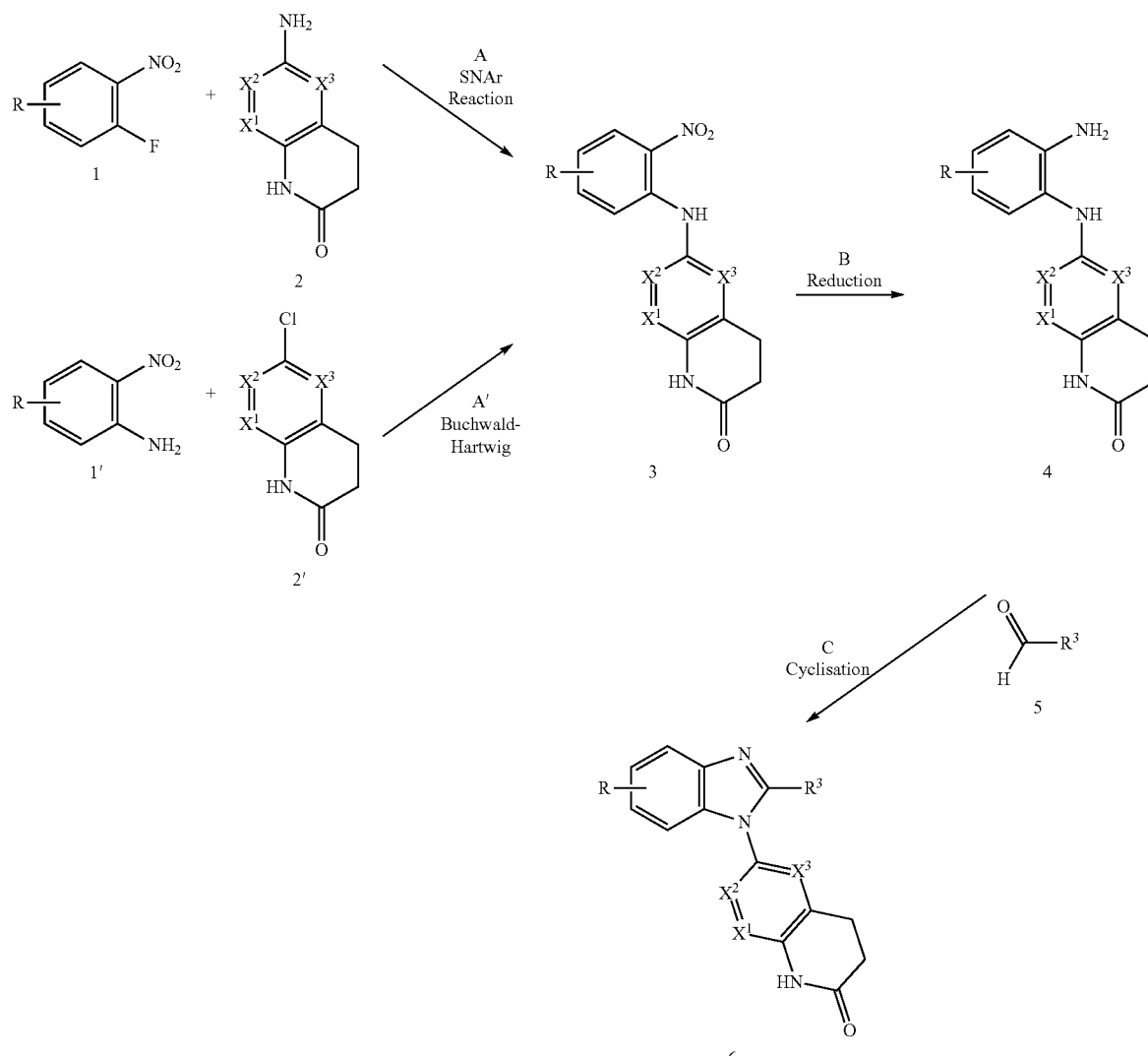

R = H, —C(O)NHMe, —C(O)OMe
R1 = as defined in herein
X1, X2, X3 = as defined in herein The substituents are as described above and R is H, —C(O)NHMe, —C(O)OMe.

Step A or Step A': Nitro-amino-arene compound 3 can be obtained by an aromatic nucleophilic substitution ($S_NAr$) reaction between a 1,2-fluoro-nitro-arene 1 and an aromatic amine compound 2 or by a Buchwald-Hartwig reaction between a 1,2-amino-nitro arene 1' and an aromatic chloride compound 2'.

Examples of suitable 1,2-fluoro-nitro-arenes 1 include, but are not limited to, 1-fluoro-2-nitrobenzene (CAS 1493-27-2), 4-fluoro-N-methyl-3-nitrobenzamide (CAS 475216-25-2), 3-fluoro-N-methyl-4-nitrobenzamide (CAS 658700-20-0), methyl 4-fluoro-3-nitrobenzoate (CAS 329-59-9), methyl 3-fluoro-4-nitrobenzoate (CAS 185629-31-6).

Examples of suitable aromatic amine compounds 2 include, but are not limited to, 6-amino-3,4-dihydro-1H-quinolin-2-one (CAS 22246-13-5).

The $S_NAr$ reaction is carried out in the presence of an organic base such as N,N-diisopropylethylamine, triethylamine or N-methylmorpholine in a polar aprotic organic solvent such as N-methyl-2-pyrrolidinone or N,N-dimethylformamide at elevated temperatures. Preferred conditions are N,N-diisopropylethylamine in N-methyl-2-pyrrolidinone at 60-120° C. overnight.

Examples of suitable 1,2-amino-nitro arene 1' include, but are not limited to, 4-amino-3-nitro-benzoate (CAS 3987-92-6).

Examples of suitable aromatic halides compounds 2' include, but are not limited to, 6-chloro-3,4-dihydro-1H-1,5-naphthyridin-2-one (CAS 1256795-00-2).

The Buchwald-Hartwig reaction is carried out in the presence of a palladium catalyst, a ligand, and a base in solvents such as dioxane, DME, THF, toluene, DMF and DMSO at elevated temperatures.

Preferred conditions are catalytic tris(dibenzylidineacetone)dipalladium, 4,5-bis(diphenylphosphino)-9,9-dimethylxanthene and cesium carbonate in a sealed tube heated at 120° C. for 12 hours.

Step B: Reduction of nitro-amino-arene compound 3 to diamino-arene 4 can be effected by hydrogenation with hydrogen under normal or elevated pressure in the presence of a catalyst such as PtO₂, Pd—C or Raney Nickel in polar solvents such as MeOH, EtOH, dioxane, THF, or mixtures thereof.

Preferred conditions are 1 atm of hydrogen in the presence of 10% palladium on charcoal in a mixture of methanol and THF at room temperature for 2-18 hours.

Step C: Benzimidazole 6 can be obtained by cyclisation of diamino-arene 4 with an aldehyde 5 in the presence of sodium metabisulfite. The cyclisation reaction is carried out in a polar aprotic organic solvent such as N-methyl-2-pyrrolidinone or N,N-dimethylformamide at elevated temperatures. Preferred conditions are N,N-dimethylformamide at 80-120° C. for 2-48 hours.

a polar ethereal solvent such as dioxane, THF, DME or TBME at room temperature or at elevated temperatures for 2-18 hours. Preferred conditions are 1 M aq. LiOH solution in a mixture of THF and MeOH at room temperature for 18 h.

Step B: Amide bond formation can be accomplished by a coupling reaction between carboxylic acid 8 and a primary or secondary amine 9 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or in a polar aprotic organic solvent such as N-methyl-2-pyrrolidinone or N,N-dimethylformamide at room temperature or at elevated temperatures for 2-18 hours.

Preferred conditions are HATU with N,N-diisopropylethylamine in a mixture of THF and N,N-dimethylformamide at room temperature for 18 hours.

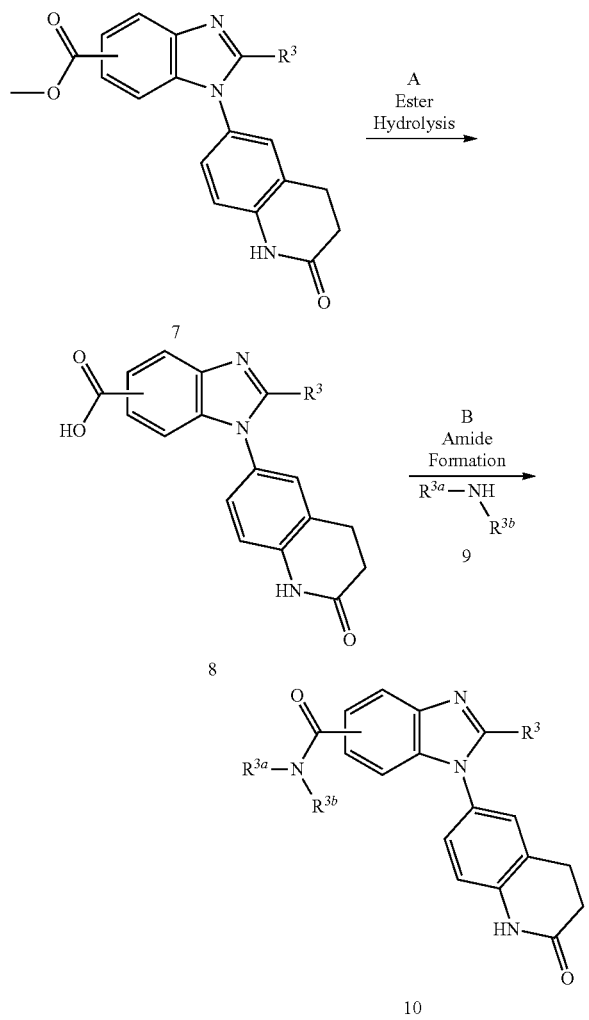

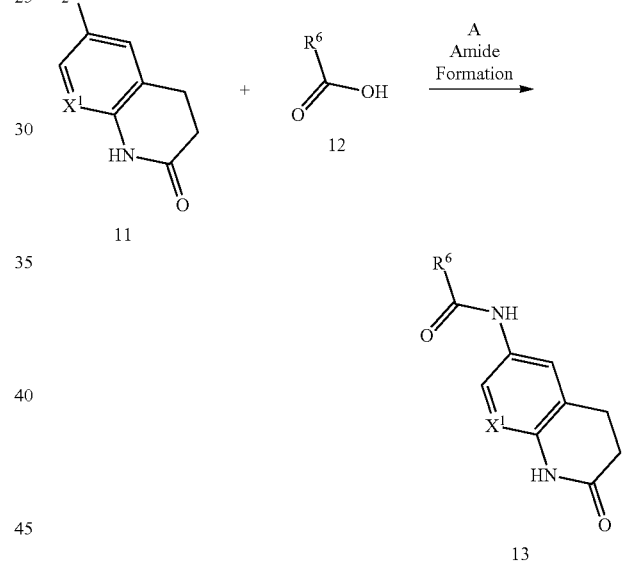

R3 = as defined herein
R3a, R3b = as defined herein

The substituents are as described above and $R^{3a}$ and $R^{3b}$ are independently of each other hydrogen or methyl.

Step A: Ester compound 7 can be hydrolysed to carboxylic acid 8 by treatment with an aqueous base such as lithium hydroxide, sodium hydroxide or potassium hydroxide. The hydrolysis reaction is carried out in a mixture of water and $X^1$ and the substituent $R^6$ are as described herein.

Step A: Amide bond formation can be accomplished by a coupling reaction between a carboxylic acid 12 and a suitable amine 11 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or in a polar aprotic organic solvent such as N-methyl-2-pyrrolidinone or N,N-dimethylformamide at room temperature or at elevated temperatures for 2-18 hours.

Examples of suitable amines 11 include, but are not limited to 6-amino-3,4-dihydroquinolin-2(1H)-one and 6-amino-3,4-dihydro-1,8-naphthyridin-2(1H)-one.

Preferred conditions are HATU with N,N-diisopropylethylamine in N,N-dimethylformamide at room temperature for 2-3 hours.

Scheme 4

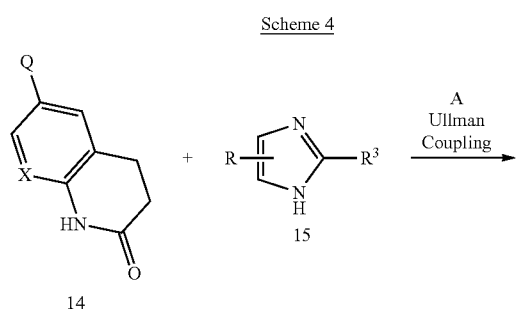

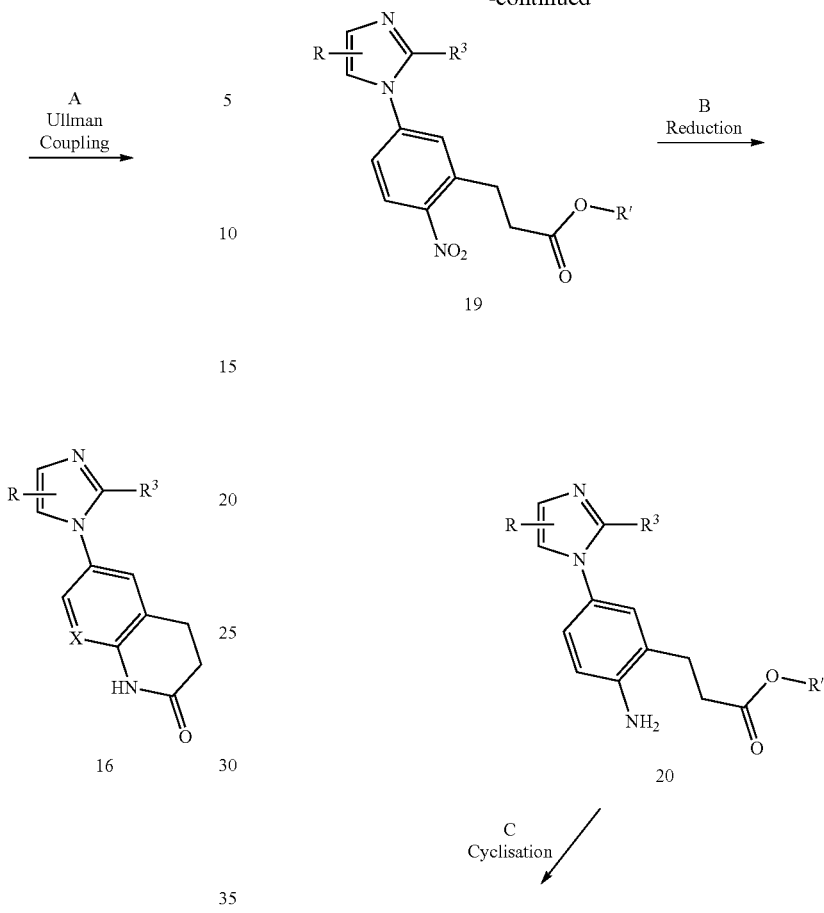

X = CH or N
Q = Br or I
R = H, ─C(O)NHMe, ─C(O)OMe
R3 as defined herein

The substituents are as described above and Q is Br or I.

Step A: Ullmann coupling between a suitable aryl bromide or aryl iodide 14 and an imidazole compound 15 can be accomplished by treatment with a copper catalyst, a diamine ligand, and a base such as K₂CO₃, Na₂CO₃, Cs₂CO₃, K₂HPO₄, KO'Bu, in solvents such as DMF, acetonitrile, DMSO, THF, DME, toluene, 1,4-dioxane, or mixtures thereof, at elevated temperatures.

Examples of suitable aryl halide compounds 11 include, but are not limited to, 6-bromo-3,4-dihydro-1H-quinolin-2-one (CAS 3279-90-1), 6-iodo-3,4-dihydro-1H-quinolin-2-one (CAS 296759-29-0) or 6-bromo-3,4-dihydro-1,8-naphthyridin-2(1H)-one (CAS 129686-16-4).

Preferred conditions are CuI, hexamethylenetetramine and potassium carbonate in DMF at 130° C. for 18-24 hours.

Scheme 5

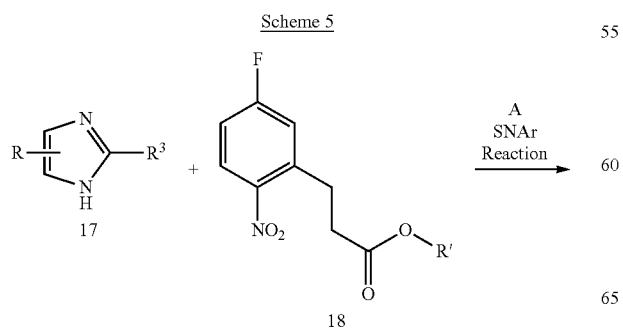

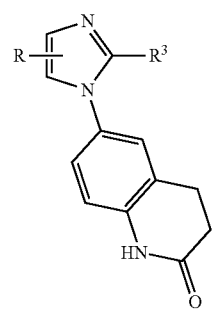

R = H, ─C(O)NHMe, ─C(O)OMe
R' = Me, Et
R3 = as defined in herein

The substituents are as described above and R' is methyl or ethyl.

Step A: Nitro-ester compound 19 can be obtained by an aromatic nucleophilic substitution ($S_NAr$) reaction between an imidazole compound 17 and a suitable fluoro-nitro-arene compound 18. Examples of suitable fluoro-nitro-arene compounds 18 include, but are not limited to, ethyl 3-(5-fluoro-2-nitrophenyl)propanoate (CAS 2369-11-1) or methyl 3-(5-fluoro-2-nitro-phenyl)propanoate (CAS 1493774-33-6).

The S$_N$Ar reaction is carried out in the presence of an inorganic base such as sodium carbonate or potassium carbonate in a polar non-protic organic solvent such as N,N-dimethylformamide at elevated temperatures. Preferred conditions are potassium carbonate in N,N-dimethylformamide at 130° C. under microwave irradiation for 15 minutes.

Step B: Reduction of nitro-ester compound 19 to amino-ester compound 20 can be effected by hydrogenation with hydrogen under normal or elevated pressure in the presence of a catalyst such as PtO$_2$, Pd—C or Raney nickel in polar solvents such as MeOH, EtOH, dioxane, THF, or mixtures thereof.

Preferred conditions are 1 atm of hydrogen in the presence of 10% palladium on charcoal in a mixture of methanol and THF at room temperature for 3 hours.

Step C: Dihydroquinolinone 21 can be obtained by cyclisation of amino-ester 20. The cyclisation reaction is carried out in the presence of a base such as sodium methoxide or sodium ethoxide in an alcohol solvent such as methanol or ethanol at elevated temperatures. Preferred conditions are sodium methoxide in ethanol at reflux for 48 hours.

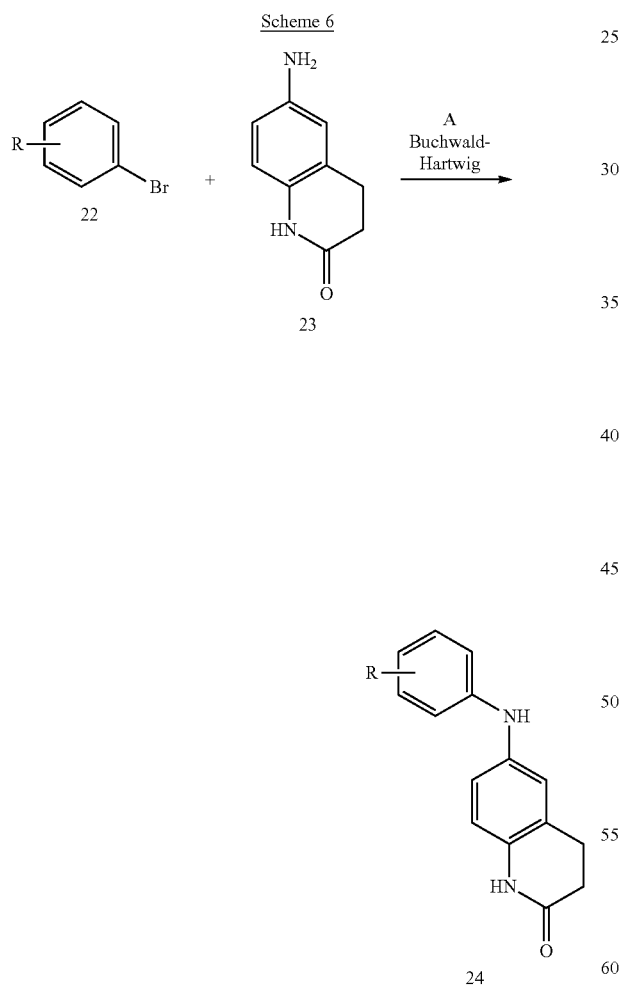

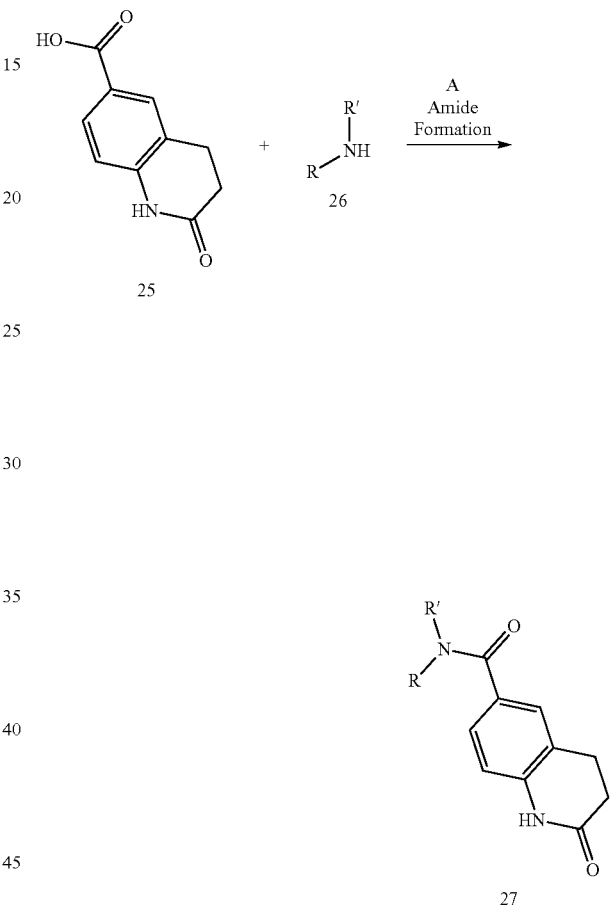

The substituent R is as described herein.

Step A: C—N bond formation can be accomplished by treatment of aryl bromide 22 with amino-quinolinone 23 in the presence of a palladium or copper catalyst, a ligand, and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium, 2-dicyclohexylphosphino-2',4',6'-triisopropylbiphenyl and sodium tert-butoxide in a sealed tube heated at 100° C. for 1 hour according to a modification of the procedure of Hartwig and co-workers *J. Am. Chem. Soc.* 1996, 118, 7217-7218.

The substituent R and R' are as described herein.

Step A: Amide bond formation can be accomplished by a coupling reaction between a carboxylic acid 25 and a suitable amine 26 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or in a polar aprotic organic solvent such as N-methyl-2-pyrrolidinone or N,N-dimethylformamide at room temperature or at elevated temperatures for 2-18 hours.

Examples of suitable amines 26 include, but are not limited to indoline (CAS 496-15-1).

Preferred conditions are HATU with N,N-diisopropylethylamine in N,N-dimethylformamide at room temperature for 2-3 hours.

Scheme 8

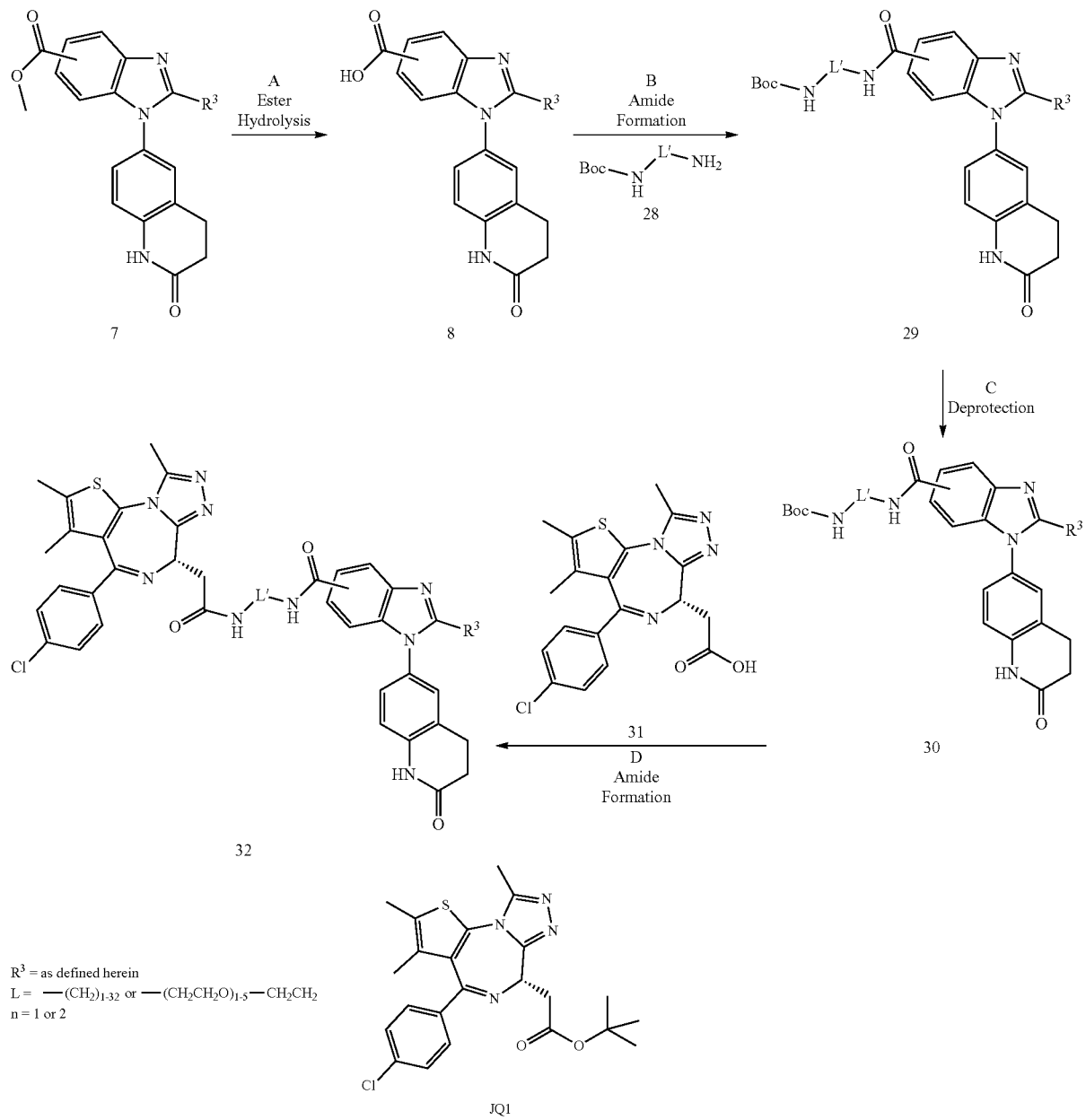

R³ = as defined herein
L = —(CH₂)₁₋₃₂ or —(CH₂CH₂O)₁₋₅—CH₂CH₂
n = 1 or 2

As an illustrative example, degrader compounds targeting the BET bromodomain BRD4 can be prepared based on the known BRD4 ligand JQ1 (Filippakopoulos, P. et al. *Nature* 2010, 468, 1067-1073). The synthesis employs the corresponding carboxylic acid derivative 31 (CAS 202592-23-2).

Step A: Ester compound 7 can be hydrolysed to carboxylic acid 8 by treatment with an aqueous base such as lithium hydroxide, sodium hydroxide or potassium hydroxide. The hydrolysis reaction is carried out in a mixture of water and a polar ethereal solvent such as dioxane, THF, DME or TBME at room temperature or at elevated temperatures for 2-18 hours. Preferred conditions are 1 M aq. LiOH solution in a mixture of THF and MeOH at room temperature for 18 h.

Step B: Amide bond formation can be accomplished by a coupling reaction between carboxylic acid 8 and a linker-containing compound 28 bearing a terminal amine functionality and a terminal BOC-protected amine functionality. The reaction is carried out in the presence of a coupling reagent such as DCC, EDC, TBTU or HATU in the presence of an organic base such as triethylamine, N,N-diisopropylethylamine, N-methylmorpholine or 4-(N,N-dimethylamino) pyridine in halogenated solvents such as dichloromethane or 1,2-dichloroethane or ethereal solvents such as diethyl ether, dioxane, THF, DME or TBME in a polar aprotic organic solvent such as N-methyl-2-pyrrolidinone or N,N-dimethylformamide at room temperature or at elevated temperatures for 2-18 hours.

Preferred conditions are HATU with N,N-diisopropylethylamine in N,N-dimethylformamide at room temperature for 18 hours.

Step C: Removal of the Boc N-protecting group of 29 can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, EtOAc, MeOH, EtOH or $H_2O$ at 0° C. to reflux temperature.

Preferred conditions are 4 M aq. HCl in dioxane and EtOAc at room temperature for 3 hours.

Step D: Amide bond formation can be accomplished by a coupling reaction between carboxylic acid 31 and amine 30 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME in a polar aprotic organic solvent such as N-methyl-2-pyrrolidinone or N,N-dimethylformamide at room temperature or at elevated temperatures for 2-18 hours.

Preferred conditions are HATU with N,N-diisopropylethylamine in N,N-dimethylformamide at room temperature for 2 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

Salts of Compounds of Formula I

In cases where the compounds of formula I are basic they may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Insofar as their preparation is not described in the examples, the compounds of formula I or formula P-L-C as well as all intermediate products can be prepared according to analogous methods or according to the methods set forth herein. Starting materials are commercially available, known in the art or can be prepared by methods known in the art or in analogy thereto.

It will be appreciated that the compounds of general formula I or formula P-L-C in this invention may be derivatised at functional groups to provide derivatives which are capable of conversion back to the parent compound in vivo.

PHARMACOLOGICAL TESTS

Figure 1:
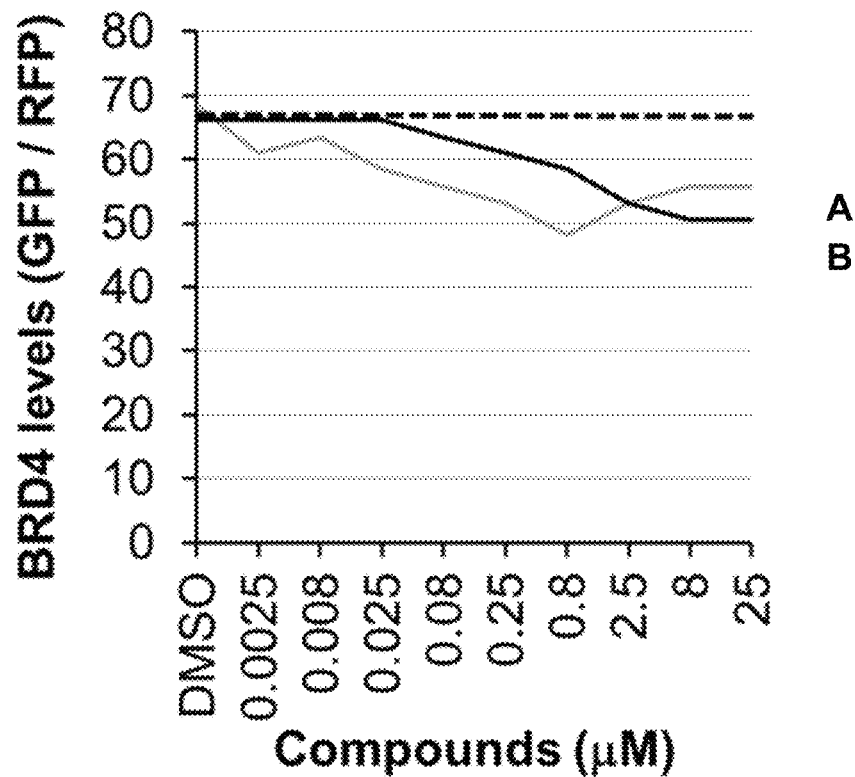
FIG. 1. Data from the dual fluorescent FACS assay show that compounds reduce BRD4-eGFP levels. Values given in the curve plot (left panel) and in the table (right panel) are the Medians of GFP vs. RFP fluorescence, the dotted line represents the mean GFP vs. RFP values in the DMSO conditions.
Figure 2:
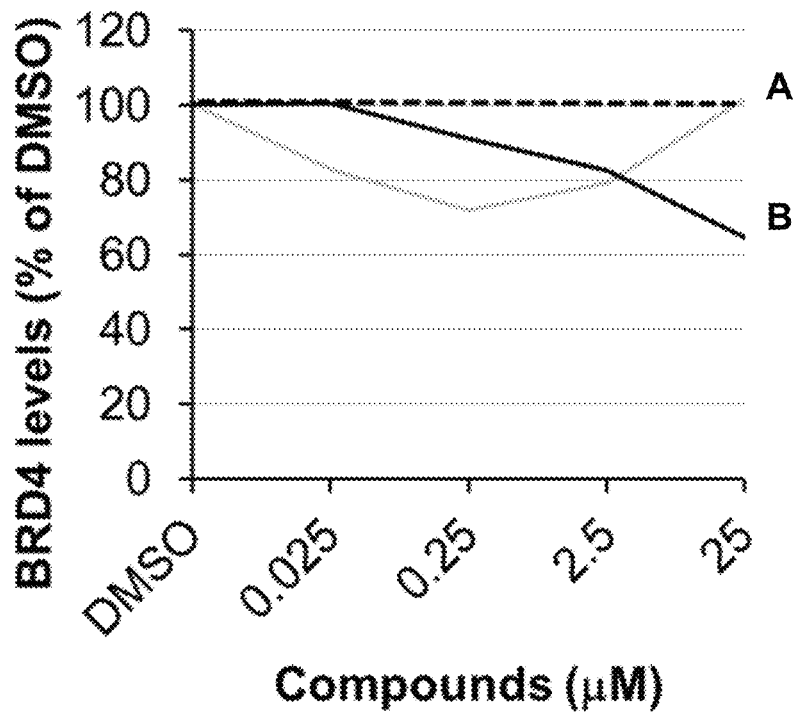
FIG. 2. Immunoassay data showing degradation of endogenous BRD4 upon compound treatment. Values shown are signal peak areas which were normalized to a loading control (vinculin) and expressed as % of DMSO.
Figure 2:
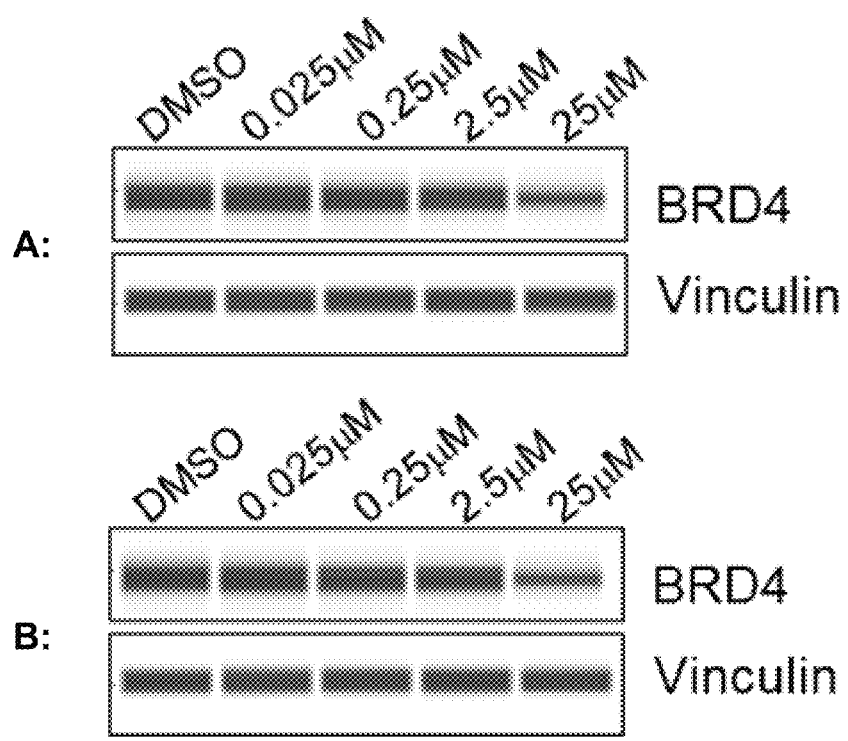

The compounds of formula I or formula P-L-C and their pharmaceutically acceptable salts possess valuable pharmacological properties. The compounds were investigated in accordance with the test given hereinafter.

Dual Fluorescent Reporter Assay

In order to measure BRD4 protein abundance in a mammalian cell system at medium throughput, a dual fluorescent reporter system was developed based on a principle described in [1]. Transient expression vectors were designed that contain the BRD4 coding sequence (NM_058243.2) fused to a fluorescent tag. Vectors were synthesized at ATUM (Newark, CA, USA) using the pD2610 CMV backbone and were built up as follows: c-terminal version BRD4_eGFP—IRES—FresnoRFP_NLS, n-terminal version eGFP_BRD4—IRES—FresnoRFP_NLS, empty vector control eGFP—IRES—FresnoRFP_NLS. The c-terminal version was used for the reporter assays, as it presented with the best assay window. HEK293A cells (Invitrogen, Cat. No. R705-07) were cultured in Dulbecco's Modified Eagle Medium (DMEM), 10% fetal calf serum, 2 mM L-Glutamine, 1% Penicillin/Streptomycin. Transfections of the plasmids were performed with Lipofectamine 2000 according to the manufacturer's protocol (Invitrogen, Carlsbad, CA, USA). 40 hours after transfection, cells were seeded at a density of 40'000/100 ul/96 well flat-bottom and 8 hours later treated with compounds (stocks 10 mM in DMSO) at a 10-point dilution ranging from 0-25 µM. After 16 hours of treatment, cells were washed with PBS, resuspended in Accumax solution (Sigma-Aldrich Cat. No. A7089) and analyzed by flow-cytometry (CytoFlex S, BeckmanCoulter). Single cells were gated based on their forward and side-scatter profiles and pulse-width was used to exclude doublets. A minimum of 20'000 cells was acquired per sample. Analysis was performed with the program Flow Jo V10.1 on BRD4-eGFP low/medium cells (<106 FL1-A Mean Fluorescence Intensity (MFI)). A factor was derived to normalize BRD4-eGFP values to the RFP protein abundance control (20×FL1A-GFP/FL11A-RFP), then Median and Mode values were calculated and used for comparisons between treatment conditions.

Capillary-Based Immunoassays to Measure Endogenous BRD4 Levels

The biological activity of selected compounds (cut-off >20% reduction in BRD4-eGFP levels) was confirmed in an additional assay which allowed the quantification of endogenous BRD4 levels. To this end, HEK293A cells (origin and culture conditions see above) were seeded at 400'000/300 ul/48 well and were treated 6 hours later with compound concentrations as indicated for. 16 hours after the treatment, the cells were washed with PBS and lysed in 50 ul of UREA lysis buffer (10 mM Tris-HCl pH 8, 2% CHAPS, 7M UREA, 0.4% DTT), supplemented with 1× protease inhibitor cocktail (Complete Mini, Roche) and 1× phosphatase inhibitor cocktail (PhosSTOP, Sigma-Aldrich). Samples were then analyzed by Peggy Sue or WES capillary-based immunoassay systems according to the manufacturer's protocol (Protein Simple/Bio-Techne, San Jose, California, 95134 USA). Antibodies used were anti-BRD4 (Cell signaling, CST 13440 1:50) and anti-Vinculin (Sigma, V9131, 1:4000). To quantify BRD4 protein levels, the peak signal areas were normalized to the vinculin loading control and to the DMSO condition.

Further, please see Yen, H.-C. S., Xu, Q., Chou, D. M., Zhao, Z. & Elledge, S. J. Global Protein Stability Profiling in Mammalian Cells. *Science* 2008, 322, 918-923, doi: 10.1126/science.1160489.

Fluorescence Direct Binding Protocol

Principle

Determination of the affinities of compounds to protein containing one or more tryptophan is measurable by monitoring the fluorescence emission in direct mode. The measurements depending on the protein available amounts are performed either manually in a cuvette on ISS-PC1 photon counting spectrofluorometer or automatically in well plates on a fluorescence plate reader device. Fluorescence titrations are performed at 20° C. in the chosen binding assay buffer by using a defined constant protein concentration against ligand concentration variations. Small aliquots of known ligand concentration solubilized in DMSO were added and the fluorescence, excited at 280 nm, was recorded at 340 nm. The fluorescence intensity was corrected for protein dilution and for the filter effect (Birdsall, B., King, R. W., Wheeler, M. R., Lewis, C. A. Jr, Goode, S. R., Dunlap, R. B. & Roberts, G. C. *Anal. Biochem.* 1983, 132, 353-361). The corrected fluorescence intensity was plotted against the ligand concentration and fitted using a four-parameter sigmoidal function, from which the equilibrium dissociation constant $K_d$ was computed using the law of mass action assuming a 1:1 protein-ligand complex (Eftink, *Methods Enzymol.* 1997, 278, 221-57).

Process

1) Optimization of measurement parameters to minimize protein consumption and to minimize the dilution effect and the DMSO content 2) Titration measurements of the protein against ligand by at least 12 titration steps to obtain a good s-curve fit 3) Repeat the same titration measurements with the ligand alone to enable correction 4) Check the stability of the protein once by titration against DMSO alone 5) Determination of the molar extinction coefficients of the ligand at 280 and 340 nm with help of a UV-spectrophotometer 6) Use Excel template for the correction of the measured raw data 7) Use GraphPad Prism software for the quadratic binding fit and the $K_d$ evaluation.

Experimental Details

TABLE 1

Protein - buffers, Reference compound: thalidomide, Contergan, Softenon

| Protein Batch # | Cereblon_17_13 |
| --- | --- |
| Construct name | hCereblon(M1-L442)_hDDB1(M1-H1140) |
| Concentration | 2.54 mg/ml |
| MW | 180180 Da |
| Molar extinction coefficient | $\varepsilon_{280} = 165045 M^{-1} \cdot cm^{-1}$ |
| Storage buffer | 20 mM MES pH 6.5 200 mM NaCl 1 mM TCEP |
| Assay buffer | 50 mM Hepes 7.4 200 mM NaCl |

TABLE 2

Settings

| Device | ISS-PC1 |
| --- | --- |
| Excitation wavelength [nm] | 280 |
| Emission wavelength [nm] | 340 |
| Cuvette | Hellma 115F-QS |
| Volume [µL] | 500 |

Protein Preparation:

TABLE 3

Protein preparation

| Volume Protein [µL] | Volume buffer [µL] | Protein concentration [M] |
| --- | --- | --- |
| 1.8 @ 2.54 mg/ml | 498.2 | 5.0E−8 |

TABLE 4

Titration steps

| C Lig [M] | C Aliquot [M] | V Aliquot [µL] | C Prot [M] | Dilution factor |
| --- | --- | --- | --- | --- |
| 1E−10 | 1.0E−07 | 0.5 | 4.995E−08 | 1.001 |
| 1.1E−09 | 1.0E−06 | 0.5 | 4.990E−08 | 1.002 |
| 3.1E−09 | 1.0E−06 | 1 | 4.980E−08 | 1.004 |
| 5.1E−09 | 1.0E−06 | 1 | 4.970E−08 | 1.006 |
| 1.51E−08 | 1.0E−05 | 0.5 | 4.965E−08 | 1.007 |
| 2.51E−08 | 1.0E−05 | 0.5 | 4.960E−08 | 1.008 |
| 4.51E−08 | 1.0E−05 | 1 | 4.950E−08 | 1.01 |
| 6.51E−08 | 1.0E−05 | 1 | 4.941E−08 | 1.012 |
| 1.651E−07 | 1.0E−04 | 0.5 | 4.936E−08 | 1.013 |
| 3.651E−07 | 1.0E−04 | 1 | 4.926E−08 | 1.015 |
| 5.651E−07 | 1.0E−04 | 1 | 4.916E−08 | 1.017 |
| 7.651E−07 | 1.0E−04 | 1 | 4.907E−08 | 1.019 |
| 9.651E−07 | 1.0E−04 | 1 | 4.897E−08 | 1.021 |
| 1.9651E−06 | 1.0E−03 | 0.5 | 4.892E−08 | 1.022 |
| 2.9651E−06 | 1.0E−03 | 0.5 | 4.888E−08 | 1.023 |
| 1.29651E−05 | 1.0E−02 | 0.5 | 4.883E−08 | 1.024 |
| 2.29651E−05 | 1.0E−02 | 0.5 | 4.878E−08 | 1.025 |
| 4.29651E−05 | 1.0E−02 | 1 | 4.869E−08 | 1.027 |
| 6.29651E−05 | 1.0E−02 | 1 | 4.859E−08 | 1.029 |
| 8.29651E−05 | 1.0E−02 | 1 | 4.850E−08 | 1.031 |

TABLE 5 affinities of examples to CRBN protein

| Example | Name | Fluorescence h-Cereblon_DDB1 Mean $K_d$_EQ (μM) |
|---|---|---|
| 1 | 6-Imidazol-1-yl-3,4-dihydro-1H-quinolin-2-one | 0.416 |
| 2 | N-Methyl-2-[2-(3-methylimidazol-4-yl)-4-quinolyl]-1-(2-oxo-3,4-dihydro-1H-quinolin-6-yl)benzimidazole-5-carboxamide | 0.040 |
| 3 | 2-Ethyl-N-methyl-1-(2-oxo-3,4-dihydro-1H-quinolin-6-yl)benzimidazole-5-carboxamide | 0.190 |
| 4 | N-Methyl-1-(2-oxo-1,2,3,4-tetrahydroquinolin-6-yl)-2-(quinolin-4-yl)-1H-benzo[d]imidazole-5-carboxamide | 0.049 |
| 5 | 3-(1-Methyl-1H-imidazol-5-yl)-N-(2-oxo-1,2,3,4-tetrahydroquinolin-6-yl)-1-naphthamide | 0.677 |
| 6 | 2-Benzyl-N-methyl-1-(2-oxo-1,2,3,4-tetrahydroquinolin-6-yl)-1H-benzo[d]imidazole-5-carboxamide | 0.702 |
| 7 | 2-Cyclopropyl-N-methyl-1-(2-oxo-1,2,3,4-tetrahydroquinolin-6-yl)-1H-benzo[d]imidazole-5-carboxamide | 0.456 |
| 8 | 2-((Benzyloxy)methyl)-N-methyl-1-(2-oxo-1,2,3,4-tetrahydroquinolin-6-yl)-1H-benzo[d]imidazole-5-carboxamide | 0.788 |
| 9 | 6-(1H-Imidazol-1-yl)-3,4-dihydro-1,8-naphthyridin-2(1H)-one | 0.016 |
| 10 | 2-(2-Methoxybenzyl)-N-methyl-1-(2-oxo-1,2,3,4-tetrahydroquinolin-6-yl)-1H-benzo[d]imidazole-5-carboxamide | 0.010 |
| 11 | N-Methyl-1-(2-oxo-1,2,3,4-tetrahydroquinolin-6-yl)-2-(1-phenylcyclopropyl)-1H-benzo[d]imidazole-5-carboxamide | 0.616 |
| 12 | N-Methyl-1-(2-oxo-1,2,3,4-tetrahydroquinolin-6-yl)-2-(1H-pyrazo]-4-y])-1H-benzo[d]imidazole-5-carboxamide | 0.250 |
| 13 | 2-(2-Methoxypyridin-4-yl)-N-methyl-1-(2-oxo-1,2,3,4 tetrahydroquinolin-6-yl)-1H-benzo[d]imidazole-5-carboxamide | 0.031 |
| 14 | 6-(5-Phenyl-1H-imidazol-1-yl)-3,4-dihydroquinolin-2(1H)-one | 0.009 |
| 15 | 2-(Hydroxymethyl)-N-methyl-1-(2-oxo-1,2,3,4-tetrahydroquinolin-6-yl)-1H-benzo[d]imidazole-5-carboxamide | 0.011 |
| 16 | 2-(2-(Cyclopropanecarboxamido)ethyl)-N-methyl-1-(2-oxo-1,2,3,4-tetrahydroquinolin-6-yl)-1H-benzo[d]imidazole-5-carboxamide | 0.027 |
| 17 | Ethyl 5-(methylcarbamoyl)-1-(2-oxo-1,2,3,4-tetrahydroquinolin-6-yl)-1H-benzo[d]imidazole-2-carboxylate | 0.010 |
| 18 | 2-(2-aminoethyl)-N-methyl-1-(2-oxo-1,2,3,4-tetrahydroquinolin-6-yl)-1H-benzo[d]imidazole-5-carboxamide | 0.004 |
| 19 | Methyl 4-((2-oxo-1,2,3,4-tetrahydroquinolin-6-yl)amino)benzoate | 0.030 |
| 20 | N-Methyl-2-(morpholine-4-carbonyl)-1-(2-oxo-1,2,3,4-tetrahydroquinolin-6-yl)-1H-benzo[d]imidazole-5-carboxamide | 0.010 |
| 21 | (RS)-N-(7-Oxo-5,6,7,8-tetrahydro-1,8-naphthyridin-3-yl)-1,2,3,4-tetrahydronaphthalene-1-carboxamide | 0.004 |
| 22 | Methyl 2-(2-methoxypyridin-4-yl)-1-(2-oxo-1,2,3,4 tetrahydroquinolin-6-yl)-1H-benzo[d]imidazole-5-carboxylate | 0.004 |
| 23 | 2-(6-Methoxypyridin-2-yl)-N-methyl-1-(2-oxo-1,2,3,4-tetrahydroquinolin-6-yl)-1H-benzo[d]imidazole-5-carboxamide | 0.015 |
| 24 | 2-(6-Methoxypyridin-3-yl)-N-methyl-1-(2-oxo-1,2,3,4-tetrahydroquinolin-6-yl)-1H-benzo[d]imidazole-5-carboxamide | 0.012 |
| 25 | 2-(4-Methoxypyridin-2-yl)-N-methyl-1-(2-oxo-1,2,3,4-tetrahydroquinolin-6-yl)-1H-benzo[d]imidazole-5-carboxamide | 0.003 |
| 26 | 2-(2-Methoxypyridin-3-yl)-N-methyl-1-(2-oxo-1,2,3,4-tetrahydroquinolin-6-yl)-1H-benzo[d]imidazole-5-carboxamide | 0.015 |
| 27 | 6-(5-(4-Methoxyphenyl)-1H-imidazol-1-yl)-3,4-dihydroquinolin-2(1H)-one | 0.022 |
| 28 | 2-Isopropyl-N-methyl-1-(7-oxo-6,8-dihydro-5H-1,8-naphthyridin-3-yl)benzimidazole-5-carboxamide | 0.008 |

TABLE 5-continued affinities of examples to CRBN protein

| Example | Name | Fluorescence h-Cereblon_DDB1 Mean $K_d$_EQ (μM) |
|---|---|---|
| 29 | 2-(2-Methoxy-4-pyridyl)-N-methyl-1-(7-oxo-6,8-dihydro-5H-1,8-naphthyridin-3-yl)benzimidazole-5-carboxamide | 0.035 |
| 30 | 2-(2-Acetylphenyl)-N-methyl-1-(2-oxo-3,4-dihydro-1H-quinolin-6-yl)benzimidazole-5-carboxamide | 0.579 |
| 31 | N-Methyl-2-[2-(methylcarbamoyl)phenyl]-1-(2-oxo-3,4-dihydro-1H-quinolin-6-yl)benzimidazole-5-carboxamide | 0.004 |
| 32 | 2-(3-Methoxyphenyl)-N-methyl-1-(2-oxo-3,4-dihydro-1H-quinolin-6-yl)benzimidazole-5-carboxamide | 0.017 |
| 33 | 2-(5-Methoxy-2-methyl-phenyl)-N-methyl-1-(2-oxo-3,4-dihydro-1H-quinolin-6-yl)benzimidazole-5-carboxamide | 0.045 |
| 34 | 2-[4-(Acetamidomethyl)phenyl]-N-methyl-1-(2-oxo-3,4-dihydro-1H-quinolin-6-yl)benzimidazole-5-carboxamide | 0.431 |
| 35 | 2-(2-Fluoro-5-methoxy-phenyl)-N-methyl-1-(2-oxo-3,4-dihydro-1H-quinolin-6-yl)benzimidazole-5-carboxamide | 0.014 |
| 36 | 2-[2-(Hydroxymethyl)phenyl]-N-methyl-1-(2-oxo-3,4-dihydro-1H-quinolin-6-yl)benzimidazole-5-carboxamide | 0.039 |
| 37 | 2-(2-Acetamidophenyl)-N-methyl-1-(2-oxo-3,4-dihydro-1H-quinolin-6-yl)benzimidazole-5-carboxamide | 0.439 |
| 38 | 2-(2-Aminophenyl)-N-methyl-1-(2-oxo-3,4-dihydro-1H-quinolin-6-yl)benzimidazole-5-carboxamide | 0.006 |
| 39 | 2-(4-Methoxy-6-methyl-2-pyridyl)-N-methyl-1-(2-oxo-3,4-dihydro-1H-quinolin-6-yl)benzimidazole-5-carboxamide | 0.006 |
| 40 | Methyl 2-[5-(methylcarbamoyl)-1-(2-oxo-3,4-dihydro-1H-quinolin-6-yl)benzimidazol-2-yl]pyridine-3-carboxylate | 0.069 |
| 41 | Methyl 2-[[5-(methylcarbamoyl)-1-(2-oxo-3,4-dihydro-1H-quinolin-6-yl)benzimidazol-2-yl]methyl]benzoate | 0.068 |
| 42 | 2-(3-Acetamido-2-pyridyl)-N-methyl-1-(2-oxo-3,4-dihydro-1H-quinolin-6-yl)benzimidazole-5-carboxamide | 0.004 |
| 43 | 2-(3-Amino-2-pyridyl)-N-methyl-1-(2-oxo-3,4-dihydro-1H-quinolin-6-yl)benzimidazole-5-carboxamide | 0.031 |
| 44 | 2-(5-Fluoro-2-methoxy-4-pyridyl)-N-methyl-1-(2-oxo-3,4-dihydro-1H-quinolin-6-yl)benzimidazole-5-carboxamide | 0.010 |
| 45 | N-Methyl-1-(2-oxo-3,4-dihydro-1H-quinolin-6-yl)-2-[3-(trifluoromethyl)-4-pyridyl]benzimidazole-5-carboxamide | 0.027 |
| 46 | 2-[2-(Hydroxymethyl)-4-pyridyl]-N-methyl-1-(2-oxo-3,4-dihydro-1H-quinolin-6-yl)benzimidazole-5-carboxamide | 0.014 |
| 47 | 2-[[2-Methoxy-4-(trifluoromethyl)phenyl]methyl]-N-methyl-1-(2-oxo-3,4-dihydro-1H-quinolin-6-yl)benzimidazole-5-carboxamide | 0.017 |
| 48 | 2-(2-Acetyl-3-pyridyl)-N-methyl-1-(2-oxo-3,4-dihydro-1H-quinolin-6-yl)benzimidazole-5-carboxamide | 0.004 |
| 49 | N-Methyl-2-[3-(methylcarbamoyl)-2-pyridyl]-1-(2-oxo-3,4-dihydro-1H-quinolin-6-yl)benzimidazole-5-carboxamide | 0.002 |
| 50 | Methyl 2-isopropyl-1-(6-oxo-7,8-dihydro-5H-1,5-naphthyridin-2-yl)benzimidazole-5-carboxylate | 0.020 |
| 51 | 2-Isopropyl-N-methyl-1-(6-oxo-7,8-dihydro-5H-1,5-naphthyridin-2-yl)benzimidazole-5-carboxamide | 0.011 |
| 52 | 2-Isopropyl-N,N-dimethyl-1-(6-oxo-7,8-dihydro-5H-1,5-naphthyridin-2-yl)benzimidazole-5-carboxamide | 0.022 |
| 53 | 7-(1H-Imidazol-1-yl)-3,4-dihydroquinolin-(1H)-one | 0.016 |
| 54 | 6-(Indoline-1-carbonyl)-3,4-dihydro-1H-quinolin-2-one | 0.232 |
| 55 | 6-(2,3-Dihydropyrrolo[2,3-b]pyridine-1-carbonyl)-3,4-dihydro-1H-quinolin-2-one | 0.023 |
| 56 | 6-(3,4-Dihydro-2H-quinoline-1-carbonyl)-3,4-dihydro-1H-quinolin-2-one | 0.005 |
| 57 | N-(1-Acetyl-4-piperidyl)-2-oxo-3,4-dihydro-1H-quinoline-6-carboxamide | 0.041 |
| 58 | 6-(Indoline-1-carbonyl)-3,4-dihydro-1H-1,8-naphthyridin-2-one | 0.062 |
| 59 | 6-(2,3-Dihydropyrrolo[2,3-b]pyridine-1-carbonyl)-3,4-dihydro-1H-1,8-naphthyridin-2-one | 0.003 |
| 60 | 6-(3,4-Dihydro-2H-quinoline-1-carbonyl)-3,4-dihydro-1H-1,8-naphthyridin-2-one | 0.001 |
| 61 | 6-(2-Isopropyl-1H-benzo[d]imidazol-1-yl)-3,4-dihydroquinazolin-2(1H)-one | 0.171 |

TABLE 5-continued affinities of examples to CRBN protein

| Example | Name | Fluorescence h-Cereblon_DDB1 Mean $K_d$_EQ (μM) |
|---|---|---|
| 62 | 2-Isopropyl-N-methyl-1-(2-oxo-1,2,3,4-tetrahydroquinazolin-6-yl)-1H-benzo[d]imidazole-5-carboxamide | 0.12 |
| A | N-(10-(2-(((6S)-4-(4-Chlorophenyl)-2,3,9-trimethyl-6H-thieno[3,2-f][1,2,4]triazolo[4,3-a][1,4]diazepin-6-yl)acetamido)decyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide | 0.338 |
| B | N-(5-(2-(((6S)-4-(4-Chlorophenyl)-2,3,9-trimethyl-6H-thieno[3,2-f][1,2,4]triazolo[4,3-a][1,4]diazepin-6-yl)acetamido)pentyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide | 0.258 |
| C | N-(2-(2-(2-(2-(((6S)-4-(4-Chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide | 0.524 |

Pharmaceutical Compositions

The compounds of formula I or formula P-L-C and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I or formula P-L-C and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or formula P-L-C or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I or formula P-L-C. Examples of compositions according to the invention are:

Example A

Tablets of the following composition are manufactured in the usual manner:

TABLE 6 possible tablet composition

| ingredient | mg/tablet | | | |
|---|---|---|---|---|
| | 5 | 25 | 100 | 500 |
| Compound of formula A, I or formula P-L-C | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 7 possible capsule ingredient composition

| ingredient | mg/capsule | | | |
|---|---|---|---|---|
| | 5 | 25 | 100 | 500 |
| Compound of formula A, I or formula P-L-C | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula A, I or formula P-L-C, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 8 possible soft gelatin capsule ingredient composition

| ingredient | mg/capsule |
|---|---|
| Compound of formula A, I or formula P-L-C | 5 |
| Yellow wax | 8 |
| Hydrogenated Soya bean oil | 8 |
| Partially hydrogenated plant oils | 34 |
| Soya bean oil | 110 |
| Total | 165 |

TABLE 9 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula A, I or formula P-L-C is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 10 possible suppository composition

| ingredient | mg/supp. |
|---|---|
| Compound of formula A, I or formula P-L-C | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula A, I or formula P-L-C is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 11 possible injection solution composition

| ingredient | mg/injection solution. |
|---|---|
| Compound of formula A, I or formula P-L-C | 3 |
| Polyethylene Glycol 400 | 150 |
| acetic acid | q.s. ad pH 5.0 |
| water for injection solutions | ad 1.0 ml |

Manufacturing Procedure

The compound of formula A, I or formula P-L-C is dissolved in a mixture of Polyethylene Glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Example E

Sachets of the following composition are manufactured:

TABLE 12 possible sachet composition

| ingredient | mg/sachet |
|---|---|
| Compound of formula I or formula P-L-C | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |

TABLE 12-continued

| possible sachet composition | |
|---|---|
| ingredient | mg/sachet |
| Magnesium stearate | 10 |
| Flavoring additives | 1 |
| Total | 2500 |

Manufacturing Procedure

The compound of formula A, I or formula P-L-C is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

Example 1

6-Imidazol-1-yl-3,4-dihydro-1H-quinolin-2-one

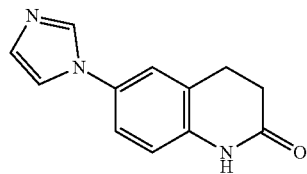 [SMILES: O=C1CCc2cc(-n3ccnc3)ccc2N1]

The title compound can be purchased.

Example 2

N-Methyl-2-[2-(3-methylimidazol-4-yl)-4-quinolyl]-1-(2-oxo-3,4-dihydro-1H-quinolin-6-yl)benzimidazole-5-carboxamide

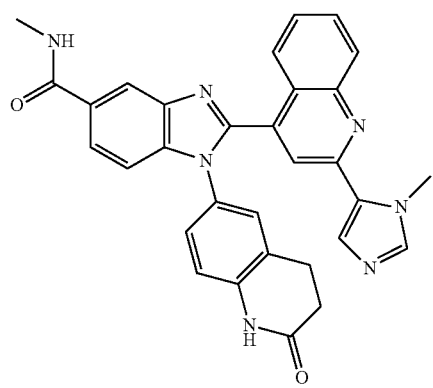 [SMILES: CNC(=O)c1ccc2c(c1)nc(-c1cc(-c3cncn3C)nc3ccccc13)n2-c1ccc2c(c1)CCC(=O)N2]

a) Methyl 3-nitro-4-((2-oxo-1,2,3,4-tetrahydroquinolin-6-yl)amino)benzoate

To a stirred solution of methyl 4-fluoro-3-nitrobenzoate (300 mg) and 6-amino-3,4-dihydro-1H-quinolin-2-one (244 mg) in N-methyl-2-pyrrolidinone (3 ml) was added dropwise N,N-diisopropylethylamine (395 µl). The reaction mixture was heated at 60° C. overnight. TLC analysis showed the reaction was complete. The reaction mixture was then cooled to room temperature and diluted with ethyl acetate and with water. The resulting mixture was filtered through sintered glass to afford methyl 3-nitro-4-((2-oxo-1,2,3,4-tetrahydroquinolin-6-yl)amino)benzoate as a red solid (365 mg, 71%). The filtrate was washed three times with water and then the organic layer was dried over $Na_2SO_4$ and concentrated in vacuo to afford methyl 3-nitro-4-((2-oxo-1,2,3,4-tetrahydroquinolin-6-yl)amino)benzoate (441 mg, 86%) as a red solid. MS (ISP): 342.1 ([M+H]$^+$).

b) Methyl 3-amino-4-((2-oxo-1,2,3,4-tetrahydroquinolin-6-yl)amino)benzoate

To a stirred suspension of methyl 3-nitro-4-((2-oxo-1,2,3,4-tetrahydroquinolin-6-yl)amino)benzoate (440 mg) in methanol (120 ml) and THF (40 ml) was added 10% palladium on charcoal (69 mg). The reaction mixture was stirred at room temperature under an atmosphere of hydrogen for 2 h. The reaction mixture was filtered through celite, washing with methanol. The filtrate was then concentrated in vacuo to afford methyl 3-amino-4-((2-oxo-1,2,3,4-tetrahydroquinolin-6-yl)amino)benzoate (351 mg, 88%) as a grey solid. MS (ISP): 312.1 ([M+H]$^+$).

c) Methyl 2-[2-(3-methylimidazol-4-yl)-4-quinolyl]-1-(2-oxo-3,4-dihydro-1H-quinolin-6-yl)benzimidazole-5-carboxylate To a stirred solution of methyl 3-amino-4-((2-oxo-1,2,3,4-tetrahydroquinolin-6-yl)amino)benzoate (106 mg) and 2-(1-methyl-1H-imidazol-5-yl)quinoline-4-carbaldehyde (CAS 432517-57-2) (88.9 mg) in N,N-dimethylformamide (4 ml) was added sodium metabisulfite (129 mg) at room temperature. The reaction mixture was then heated at 80° C. for 2 h. TLC and LC-MS analysis showed the reaction was incomplete. A further portion of sodium metabisulfite (129 mg) was added and the reaction mixture was then heated at 120° C. for 5 h. TLC and LC-MS analysis showed the reaction was complete. The reaction mixture was then cooled to room temperature and poured into EtOAc/THF (1:1 mixture). The resulting mixture was washed sequentially with water and with saturated brine. The organic phase was then separated, dried over $Na_2SO_4$, filtered, and concentrated in vacuo to afford methyl 2-[2-(3-methylimidazol-4-yl)-4-quinolyl]-1-(2-oxo-3,4-dihydro-1H-quinolin-6-yl)benzimidazole-5-carboxylate (204 mg, 99%, 88% purity) as a yellow amorphous solid which was used in the next step without further purification. MS (ISP): 529.2 ([M+H]$^+$).

d) 2-[2-(3-Methylimidazol-4-yl)-4-quinolyl]-1-(2-oxo-3,4-dihydro-1H-quinolin-6-yl)benzimidazole-5-carboxylic acid To a stirred solution of methyl 2-[2-(3-methylimidazol-4-yl)-4-quinolyl]-1-(2-oxo-3,4-dihydro-1H-quinolin-6-yl)benzimidazole-5-carboxylate (203 mg) in THF (2 ml) and MeOH (1 ml) was added dropwise 1 M aq. LiOH solution (1.01 ml). The reaction mixture was stirred at room temperature overnight. Subsequent LC-MS showed the reaction was complete. Water was added and then a few drops of 1 N aq. NaOH solution were added until the pH was basic. The mixture was extracted twice with EtOAc. 5 N aq. HCl was then added to the aqueous layer until pH 1 was reached. The aqueous layer was extracted twice with THF/EtOAc (3:1). LC-MS analysis showed no product remained in the organic layer. The aqueous layer was concentrated in vacuo and the residue was lyophilised to afford 2-[2-(3-methylimidazol-4-yl)-4-quinolyl]-1-(2-oxo-3,4-dihydro-1H-quinolin-6-yl)benzimidazole-5-carboxylic acid as a yellow solid (311 mg, 100%, 56% purity) which was used in the next step without further purification. MS (ISP): 515.2 ([M+H]$^+$).

e) N-Methyl-2-[2-(3-methylimidazol-4-yl)-4-quinolyl]-1-(2-oxo-3,4-dihydro-1H-quinolin-6-yl)benzimidazole-5-carboxamide To a suspension of 2-[2-(3-methylimidazol-4-yl)-4-quinolyl]-1-(2-oxo-3,4-dihydro-1H-quinolin-6-yl)benzimidazole-5-carboxylic acid (310 mg), N,N-diisopropylethylamine (236 µl) and methylamine (337 µl, 2 M solution in THF) in DMF (2 ml) was added HATU (308 mg). The reaction mixture was stirred at room temperature overnight. The resulting yellow suspension was filtered through sintered glass. The filtrate was concentrated in vacuo and the residue was purified by reversed phase HPLC to afford N-methyl-2-[2-(3-methylimidazol-4-yl)-4-quinolyl]-1-(2-oxo-3,4-dihydro-1H-quinolin-6-yl)benzimidazole-5-carboxamide as an off-white solid (50 mg, 28%). MS (ISP): 528.8 ([M+H]$^+$).

Example 3

2-Ethyl-N-methyl-1-(2-oxo-3,4-dihydro-1H-quinolin-6-yl)benzimidazole-5-carboxamide

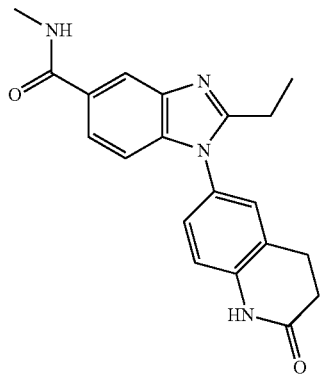 [SMILES: CCc1nc2cc(C(=O)NC)ccc2n1-c1ccc2c(c1)CCC(=O)N2]

The title compound was obtained in analogy to example 2 using propionaldehyde (CAS 123-38-6) in place of 2-(1-methyl-1'H-imidazol-5-yl)quinoline-4-carbaldehyde in step c. White solid. MS (ISP): 349.1 ([M+H]$^+$).

Example 4

N-Methyl-1-(2-oxo-1,2,3,4-tetrahydroquinolin-6-yl)-2-(quinolin-4-yl)-1H-benzo[d]imidazole-5-carboxamide

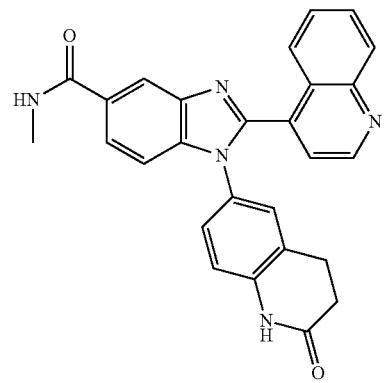 [SMILES: CNC(=O)c1ccc2c(c1)nc(-c1ccnc3ccccc13)n2-c1ccc2c(c1)CCC(=O)N2]

The title compound was obtained in analogy to example 2 using quinoline-4-carboxaldehyde (CAS 4363-93-3) in place of 2-(1-methyl-1'H-imidazol-5-yl)quinoline-4-carbaldehyde in step c. White solid. MS (ISP): 448.3 ([M+H]$^+$).

Example 5

3-(1-Methyl-1H-imidazol-5-yl)-N-(2-oxo-1,2,3,4-tetrahydroquinolin-6-yl)-1-naphthamide

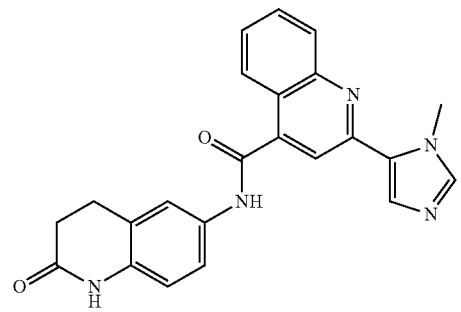 [SMILES: Cn1cncc1-c1cc(C(=O)Nc2ccc3c(c2)CCC(=O)N3)c2ccccc2n1]

To a mixture of 6-amino-3,4-dihydroquinolin-2(1H)-one (35.4 mg) and 2-(1-methyl-1H-imidazol-5-yl)quinoline-4-carboxylic acid (CAS 432516-70-6) (50.24 mg) were added a solution of 0.27 M HATU in DMF (811 µl) and N,N-diisopropylethylamine (69.3 µl). The reaction mixture was stirred at room temperature for 2.5 hours. LC-MS analysis indicated that the reaction was complete. The reaction mixture was directly purified by reversed phase HPLC. The collected fractions were concentrated in vacuo and the residue was resuspended in ethyl acetate and water. The organic phase was then separated, dried over Na$_2$SO$_4$, filtered, and concentrated in vacuo to afford 3-(1-methyl-1H-imidazol-5-yl)-N-(2-oxo-1,2,3,4-tetrahydroquinolin-6-yl)-1-naphthamide (39 mg, 50%) as an off-white. MS (ISP): 398.6 ([M+H]$^+$).

Example 6

2-Benzyl-N-methyl-1-(2-oxo-1,2,3,4-tetrahydroquinolin-6-yl)-1H-benzo[d]imidazole-5-carboxamide

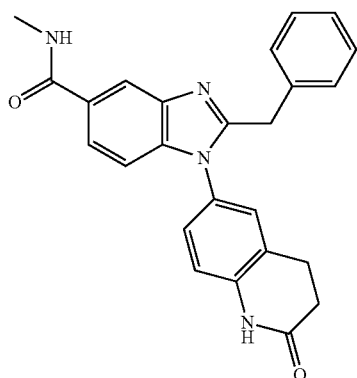 [SMILES: CNC(=O)c1ccc2c(c1)nc(Cc1ccccc1)n2-c1ccc2c(c1)CCC(=O)N2]

a) N-Methyl-3-nitro-4-((2-oxo-1,2,3,4-tetrahydroquinolin-6-yl)amino)benzamide

To a stirred solution of 4-fluoro-N-methyl-3-nitrobenzamide (500 mg) in N-methyl-2-pyrrolidinone (5 ml) were added 6-amino-3,4-dihydroquinolin-2(1H)-one (450 mg) and N,N-diisopropylethylamine (489 mg). The reaction mixture was heated at 80° C. for 3 days. LC-MS analysis indicated that the reaction was incomplete. The reaction mixture was heated at 120° C. for 1 day. The reaction mixture was cooled to room temperature and ethyl acetate (10 ml) and water (3 ml) were added. An orange precipitate formed. The precipitate was collected by filtration, washed with ethyl acetate, and dried in vacuo to give N-methyl-3-nitro-4-((2-oxo-1,2,3,4-tetrahydroquinolin-6-yl)amino)benzamide as an orange solid (825 mg, 96%). MS (ISP): 341.0 ([M+H]$^+$).

b) 3-Amino-N-methyl-4-[(2-oxo-3,4-dihydro-1H-quinolin-6-yl)amino]benzamide

To a stirred suspension of N-methyl-3-nitro-4-((2-oxo-1,2,3,4-tetrahydroquinolin-6-yl)amino)benzamide (825 mg) in methanol (20 ml) and THF (40 ml) was added 10% palladium on charcoal (258 mg). The reaction mixture was stirred at room temperature under an atmosphere of hydrogen for 15 h. The reaction mixture was filtered through celite, washing with methanol. The filtrate was then concentrated in vacuo to afford 3-amino-N-methyl-4-[(2-oxo-3,4-dihydro-1H-quinolin-6-yl)amino]benzamide (73 mg, 10%) as an off-white solid. MS (ISP): 311.0 ([M+H]$^+$).

c) 2-Benzyl-N-methyl-1-(2-oxo-1,2,3,4-tetrahydroquinolin-6-yl)-1H-benzo[d]imidazole-5-carboxamide To a stirred solution of 3-amino-N-methyl-4-((2-oxo-1,2,3,4-tetrahydroquinolin-6-yl)amino)benzamide (85 mg) and 2-phenylacetaldehyde (CAS 122-78-1) (36.2 mg) in N,N-dimethylformamide (1 ml) was added sodium metabisulfite (104 mg) at room temperature. The reaction mixture was then heated at 120° C. for 16 h. TLC and LC-MS analysis showed the reaction was complete. The reaction mixture was then cooled to room temperature and diluted with EtOAc. The resulting mixture was washed with water. The organic phase was then separated, dried over Na$_2$SO$_4$, filtered, and concentrated in vacuo. The residue was purified by flash chromatography (silica gel, 10 g, 0% to 10% methanol in dichloromethane) to afford 2-benzyl-N-methyl-1-(2-oxo-1,2,3,4-tetrahydroquinolin-6-yl)-1H-benzo[d]imidazole-5-carboxamide as a light brown solid (24 mg, 21%). MS (ISP): 411.6 ([M+H]$^+$).

Example 7

2-Cyclopropyl-N-methyl-1-(2-oxo-1,2,3,4-tetrahydroquinolin-6-yl)-1H-benzo[d]imidazole-5-carboxamide

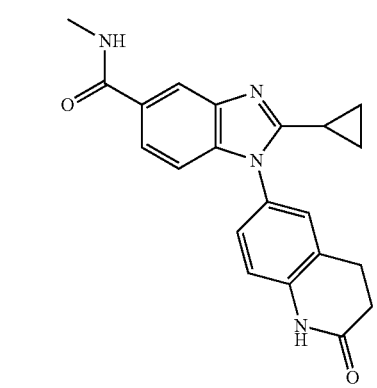 [SMILES: CNC(=O)c1ccc2c(c1)nc(C1CC1)n2-c1ccc2c(c1)CCC(=O)N2]

The title compound was obtained in analogy to example 6 using cyclopropanecarbaldehyde (CAS 7051-34-5) in place of 2-phenylacetaldehyde in step c. Grey solid. MS (ISP): 361 ([M+H]$^+$).

Example 8

2-((Benzyloxy)methyl)-N-methyl-1-(2-oxo-1,2,3,4-tetrahydroquinolin-6-yl)-1H-benzo[d]imidazole-5-carboxamide

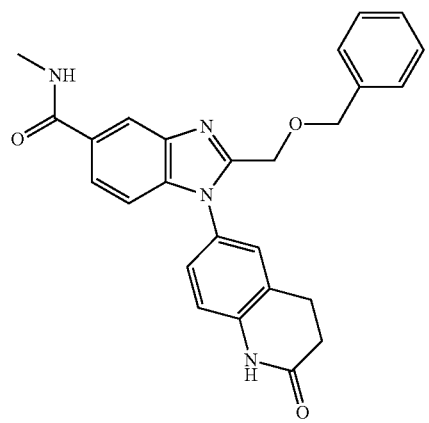 [SMILES: CNC(=O)c1ccc2c(c1)nc(COCc1ccccc1)n2-c1ccc2c(c1)CCC(=O)N2]

The title compound was obtained in analogy to example 6 using 2-(benzyloxy)acetaldehyde (CAS 60656-87-3) in place of 2-phenylacetaldehyde in step c. Yellow solid. MS (ISP): 441.3 ([M+H]$^+$).

Example 9

6-(1H-Imidazol-1-yl)-3,4-dihydro-1,8-naphthyridin-2(1H)-one

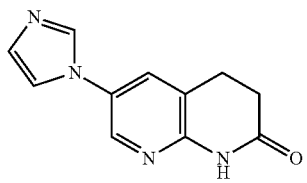 [SMILES: O=C1CCc2cc(-n3ccnc3)cnc2N1]

To a solution of 6-bromo-3,4-dihydro-1,8-naphthyridin-2(1H)-one (100 mg) in DMF (2 ml) were added 1H-imidazole (CAS 288-32-4) (33 mg), CuI (8.39 mg), hexamethylenetetramine (6.17 mg) and potassium carbonate (123 mg). The reaction mixture was heated at 130° C. for 22 hours. The reaction mixture was diluted with water (40 ml) and ethyl acetate (20 ml). The two layers were separated and the aqueous layer was back-extracted twice with ethyl acetate (2×20 ml). The combined organic layers were dried over Na$_2$SO$_4$, filtered and concentrated in vacuo. The residue was purified by chromatography (silica gel; 12 g; eluent: heptane/ethyl acetate=100/0 to 0/100 and then to 10% MeOH) to afford 6-(1H-imidazol-1-yl)-3,4-dihydro-1,8-naphthyridin-2(1H)-one as a light yellow solid (21.9 mg, 23%). %). MS (ISP): 215.4 ([M+H]$^+$).

Example 10

2-(2-Methoxybenzyl)-N-methyl-1-(2-oxo-1,2,3,4-tetrahydroquinolin-6-yl)-1H-benzo[d]imidazole-5-carboxamide

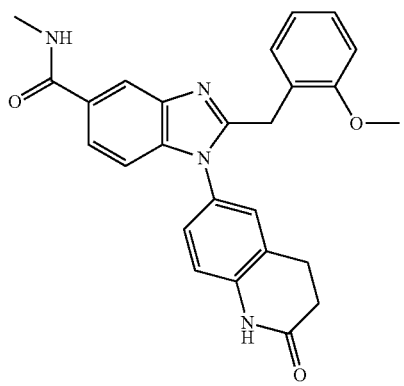 [SMILES: CNC(=O)c1ccc2c(c1)nc(Cc1ccccc1OC)n2-c1ccc2c(c1)CCC(=O)N2]

The title compound was obtained in analogy to example 6 using 2-(2-methoxyphenyl)acetaldehyde (CAS 33567-59-8) in place of 2-phenylacetaldehyde in step c. Light yellow solid. MS (ISP): 441.3 ([M+H]$^+$).

Example 11

N-Methyl-1-(2-oxo-1,2,3,4-tetrahydroquinolin-6-yl)-2-(1-phenylcyclopropyl)-1H-benzo[d]imidazole-5-carboxamide

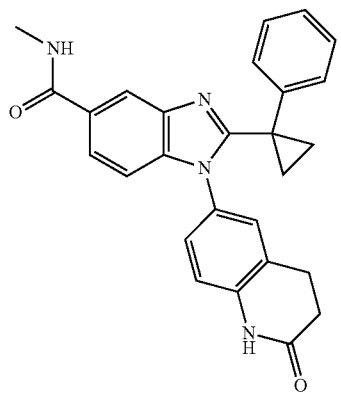 [SMILES: CNC(=O)c1ccc2c(c1)nc(C1(c3ccccc3)CC1)n2-c1ccc2c(c1)CCC(=O)N2]

The title compound was obtained in analogy to example 6 using 1-phenylcyclopropane-carbaldehyde (CAS 21744-88-7) in place of 2-phenylacetaldehyde in step c. Light yellow solid. MS (ISP): 437.5 ([M+H]$^+$).

Example 12

N-Methyl-1-(2-oxo-1,2,3,4-tetrahydroquinolin-6-yl)-2-(1H-pyrazol-4-yl)-1H-benzo[d]imidazole-5-carboxamide

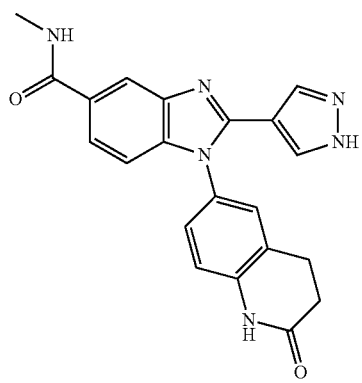 [SMILES: CNC(=O)c1ccc2c(c1)nc(-c1cn[nH]c1)n2-c1ccc2c(c1)CCC(=O)N2]

To a stirred solution of methyl 3-amino-N-methyl-4-((2-oxo-1,2,3,4-tetrahydroquinolin-6-yl)amino)benzamide (80 mg) in N,N-dimethylformamide (1 ml) was added 1H-pyrazole-4-carboxaldehyde (CAS 35344-95-7) (41.5 mg). After stirring for 2 hours at 80° C., sodium metabisulfite (98 mg) was added and the reaction mixture was heated at 120° C. for 48 h. TLC and LC-MS analysis showed the reaction was complete. The reaction mixture was then cooled to room temperature and diluted with EtOAc. The resulting mixture was washed with water. The organic phase was then separated, dried over Na$_2$SO$_4$, filtered, and concentrated in vacuo. The residue was stirred in dichloromethane, filtered, washed with dichloromethane to afford N-methyl-1-(2-oxo-1,2,3,4-tetrahydroquinolin-6-yl)-2-(1H-pyrazol-4-yl)-1H- benzo[d]imidazole-5-carboxamide as a light brown solid (47.8 mg, 48%). MS (ISP): 387.2 ([M+H]+).

Example 13

2-(2-Methoxypyridin-4-yl)-N-methyl-1-(2-oxo-1,2,3,4-tetrahydroquinolin-6-yl)-1H-benzo[d]imidazole-5-carboxamide

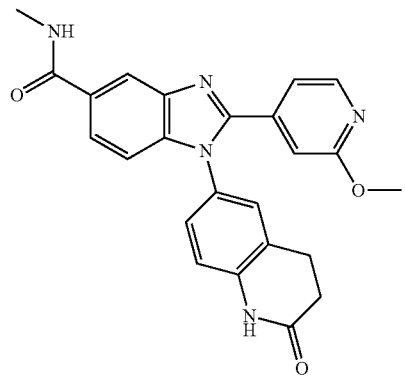 [SMILES: CNC(=O)c1ccc2c(c1)nc(-c1ccnc(OC)c1)n2-c1ccc2c(c1)CCC(=O)N2]

The title compound was obtained in analogy to example 6 using 2-methoxyisonicotinaldehyde (CAS 72716-87-1) in place of 2-phenylacetaldehyde in step c. Light yellow solid. MS (ISP): 428.3 ([M+H]+).

Example 14

6-(5-Phenyl-1H-imidazol-1-yl)-3,4-dihydroquinolin-2(1H)-one

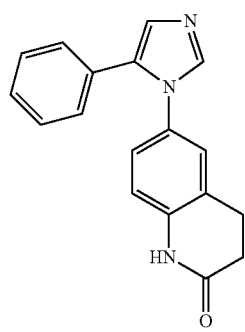 [SMILES: O=C1CCc2cc(-n3cncc3-c3ccccc3)ccc2N1]

a) Ethyl 3-(5-fluoro-2-nitrophenyl)propanoate

To a flask containing THF (200 ml) was added with stirring LiHMDS (20.5 ml, 1 M solution in THF). The solution was cooled to −78° C. and ethyl acetate (2 ml) was added slowly. After stirring for 30 min, a solution of 2-(bromomethyl)-4-fluoro-1-nitrobenzene (CAS 82420-35-7) (4 g) dissolved in THF (100 ml) was added dropwise over 30 min. The reaction mixture was then allowed to warm to room temperature and stirring continued for a further 2 hours. The reaction was quenched with water and the mixture was extracted three times with ethyl acetate. The combined organic phases were washed sequentially with water and with sat. brine, dried over MgSO4, filtered, and concentrated in vacuo. The crude material was purified by flash chromatography (silica gel, eluent: 0 to 10% of ethyl acetate in hexane) to afford ethyl 3-(5-fluoro-2-nitrophenyl)propanoate (2.20 g, 53% yield) as a yellow oil. MS (ISP): 242.1 ([M+H]+).

b) Ethyl 3-(2-nitro-5-(5-phenyl-1H-imidazol-1-yl)phenyl)propanoate

To a stirred solution of 5-phenyl-1H-imidazole (CAS 670-95-1) (100 mg) in N,N-dimethylformamide (2 ml) were added sequentially ethyl 3-(5-fluoro-2-nitrophenyl)propanoate (184 mg) and potassium carbonate (201 mg). The reaction mixture was irradiated in a microwave synthesizer apparatus for 15 min at 130° C. LC/MS analysis indicated that the reaction was finished. The reaction mixture was partitioned between ethyl acetate and water. The organic layer was separated and the aqueous phase was extracted twice with ethyl acetate. The combined organic layers were dried over MgSO4, filtered, and concentrated in vacuo. The crude material was purified by flash chromatography (silica gel, eluent: 0 to 10% of methanol in dichloromethane) to afford ethyl 3-(2-nitro-5-(5-phenyl-1H-imidazol-1-yl)phenyl)propanoate (98 mg, 39% yield) as a white solid. MS (ISP): 366.2 ([M+H]+).

c) Ethyl 3-(2-amino-5-(5-phenyl-1H-imidazol-1-yl)phenyl)propanoate

To a stirred suspension of ethyl 3-(2-nitro-5-(5-phenyl-1H-imidazol-1-yl)phenyl)propanoate (98 mg) in methanol (20 ml) and THF (40 ml) was added 10% palladium on charcoal (10 mg). The reaction mixture was stirred under an atmosphere of hydrogen at room temperature for 3 h. The reaction mixture was filtered through celite, washing with methanol. The filtrate was then concentrated in vacuo to afford ethyl 3-(2-amino-5-(5-phenyl-1H-imidazol-1-yl)phenyl)propanoate (90 mg, 100%) as an off-white foam. MS (ISP): 336.96 ([M+H]+).

d) 6-(5-Phenyl-1H-imidazol-1-yl)-3,4-dihydroquinolin-2(1H)-one

A solution of ethyl 3-(2-amino-5-(5-phenyl-1H-imidazol-1-yl)phenyl)propanoate (90 mg) was stirred in ethanol (1 ml) at reflux for 48 hours. TLC analysis indicated that the reaction was incomplete. After cooling to room temperature, sodium methanolate (50 mg) was added and the mixture was then heated at reflux for 6 hours. The reaction mixture was cooled to room temperature and concentrated in vacuo. The residue was partitioned between CH2Cl2/MeOH (90:10) and water. The organic layer was separated, dried over MgSO4, filtered, and concentrated in vacuo. The residue was suspended in CH2Cl2 and the mixture was stirred at room temperature for 30 min. The resulting solid was collected by filtration to afford 6-(5-phenyl-1H-imidazol-1-yl)-3,4-dihydroquinolin-2(1H)-one_as a white solid (30 mg, 39%). MS (ISP): 290.2 ([M+H]+).

Example 15

2-(Hydroxymethyl)-N-methyl-1-(2-oxo-1,2,3,4-tetrahydroquinolin-6-yl)-1H-benzo[d]imidazole-5-carboxamide

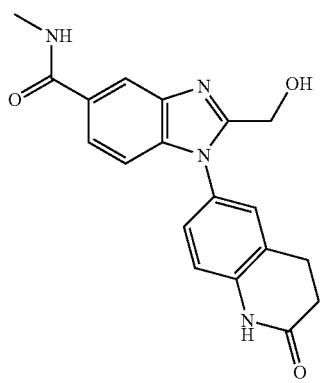 [SMILES: CNC(=O)c1ccc2c(c1)nc(CO)n2-c1ccc2c(c1)CCC(=O)N2]

To a stirred suspension of 2-(benzyloxymethyl)-N-methyl-1-(2-oxo-3,4-dihydro-1H-quinolin-6-yl)benzimidazole-5-carboxamide (63 mg, example 8) in methanol (3 ml) was added 10% palladium on charcoal (20 mg). The reaction mixture was hydrogenated at 70° C. and 5 bar for 18 hours. The reaction mixture was cooled to room temperature and then filtered through celite, washing with methanol. The filtrate was then concentrated in vacuo to afford 2-(hydroxymethyl)-N-methyl-1-(2-oxo-1,2,3,4-tetrahydroquinolin-6-yl)-1H-benzo[d]imidazole-5-carboxamide (25.3 mg, 51%) as a white crystalline solid. MS (ISP): 351.1 ([M+H]$^+$).

Example 16

2-(2-(Cyclopropanecarboxamido)ethyl)-N-methyl-1-(2-oxo-1,2,3,4-tetrahydroquinolin-6-yl)-1H-benzo[d]imidazole-5-carboxamide

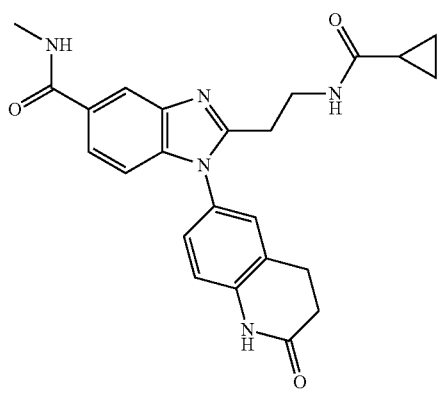 [SMILES: CNC(=O)c1ccc2c(c1)nc(CCNC(=O)C1CC1)n2-c1ccc2c(c1)CCC(=O)N2]

a) Benzyl (2-(5-(methylcarbamoyl)-1-(2-oxo-1,2,3,4-tetrahydroquinolin-6-yl)-1H-benzo[d]imidazol-2-yl)ethyl)carbamate The title compound was obtained in analogy to example 6 using benzyl (3-oxopropyl)carbamate (CAS 65564-05-8) in place of 2-phenylacetaldehyde in step c. Light yellow solid. MS (ISP): 498.1 ([M+H]$^+$).

b) 2-(2-Aminoethyl)-N-methyl-1-(2-oxo-1,2,3,4-tetrahydroquinolin-6-yl)-1H-benzo[d]imidazole-5-carboxamide To a stirred suspension of benzyl (2-(5-(methylcarbamoyl)-1-(2-oxo-1,2,3,4-tetrahydroquinolin-6-yl)-1H-benzo[d]imidazol-2-yl)ethyl)carbamate (194 mg) in methanol (4 ml) was added 10% palladium on charcoal (20 mg). The reaction mixture was hydrogenated at 70° C. and 5 bar for 18 hours. The reaction mixture was filtered through celite, washing with methanol. The filtrate was then concentrated in vacuo to afford 2-(2-aminoethyl)-N-methyl-1-(2-oxo-1,2,3,4-tetrahydroquinolin-6-yl)-1H-benzo[d]imidazole-5-carboxamide (59 mg, 42%) as a colorless oil. MS (ISP): 364.3 ([M+H]$^+$).

c) 2-(2-(Cyclopropanecarboxamido)ethyl)-N-methyl-1-(2-oxo-1,2,3,4-tetrahydroquinolin-6-yl)-1H-benzo[d]imidazole-5-carboxamide To a stirred solution of 2-(2-aminoethyl)-N-methyl-1-(2-oxo-1,2,3,4-tetrahydroquinolin-6-yl)-1H-benzo[d]imidazole-5-carboxamide (59 mg) in dichloromethane (2 ml) were added sequentially cyclopropanecarbonyl chloride (CAS 4023-34-1) (16.2 µl) and triethylamine (45.3 µl). The reaction mixture was stirred at room temperature for 48 hours. LC-MS analysis indicated that the reaction was complete. The reaction mixture was partitioned between dichloromethane and water. The organic layer was dried over MgSO$_4$, filtered, and concentrated in vacuo. The crude material was purified by flash chromatography (silica gel, eluent: 0 to 10% of methanol in dichloromethane) to afford 2-(2-(cyclopropanecarboxamido)ethyl)-N-methyl-1-(2-oxo-1,2,3,4-tetrahydroquinolin-6-yl)-1H-benzo[d]imidazole-5-carboxamide (6 mg, 7%, 90% purity) as a white solid. MS (ISP): 432.1 ([M+H]$^+$).

Example 17

Ethyl 5-(methylcarbamoyl)-1-(2-oxo-1,2,3,4-tetrahydroquinolin-6-yl)-1H-benzo[d]imidazole-2-carboxylate

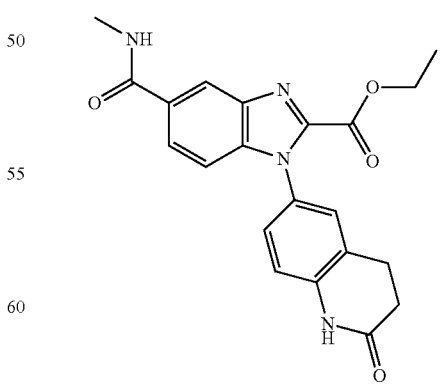

To a stirred solution of methyl 3-amino-N-methyl-4-((2-oxo-1,2,3,4-tetrahydroquinolin-6-yl)amino)benzamide (80 mg) in N,N-dimethylformamide (1 ml) was added ethyl 2-oxoacetate (CAS 924-44-7) (26.2 µl). After stirring for 2 hours at 80° C., sodium metabisulfite (98 mg) was added and the reaction mixture was heated at 120° C. for 16 h. LC-MS analysis indicated that the reaction was incomplete. A further aliquot of ethyl 2-oxoacetate (26.2 µl) was added and the reaction mixture was stirred at 120° C. for 4 hours. The reaction mixture was then cooled to room temperature and diluted with EtOAc. The resulting mixture was washed with water. The organic phase was then separated, dried over $Na_2SO_4$, filtered, and concentrated in vacuo. The crude material was purified by flash chromatography (silica gel, eluent: 0 to 5% of methanol in dichloromethane) to afford ethyl 5-(methylcarbamoyl)-1-(2-oxo-1,2,3,4-tetrahydroquinolin-6-yl)-1H-benzo[d]imidazole-2-carboxylate (26 mg, 26%) as an off-white solid. MS (ISP): 393.1 ([M+H]$^+$).

Example 18

2-(2-Aminoethyl)-N-methyl-1-(2-oxo-1,2,3,4-tetrahydroquinolin-6-yl)-1H-benzo[d]imidazole-5-carboxamide

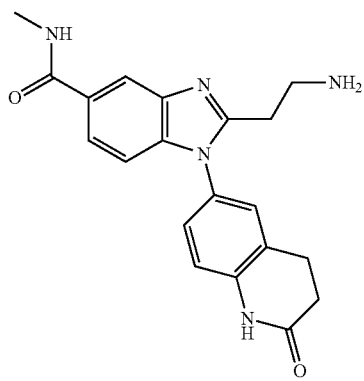 [SMILES: CNC(=O)c1ccc2c(c1)nc(CCN)n2-c1ccc2c(c1)CCC(=O)N2]

a) Benzyl (2-(5-(methylcarbamoyl)-1-(2-oxo-1,2,3,4-tetrahydroquinolin-6-yl)-1H-benzo[d]imidazol-2-yl)ethyl)carbamate The title compound was obtained in analogy to example 2 using benzyl (3-oxopropyl)carbamate in place of 2-(1-methyl-1H-imidazol-5-yl)quinoline-4-carbaldehyde in step c and stirring at 120° C. overnight instead of for 5 hours. Yellow solid. MS (ISP): 496.1 ([M+H]$^+$).

b) 2-(2-Aminoethyl)-N-methyl-1-(2-oxo-1,2,3,4-tetrahydroquinolin-6-yl)-1H-benzo[d]imidazole-5-carboxamide To a stirred solution of benzyl (2-(5-(methylcarbamoyl)-1-(2-oxo-1,2,3,4-tetrahydroquinolin-6-yl)-1H-benzo[d]imidazol-2-yl)ethyl)carbamate (106.0 mg) in methanol (2 ml) was added 10% palladium on charcoal (22.7 mg). The reaction mixture was stirred at room temperature under an atmosphere of hydrogen for 16 hours. The reaction mixture was filtered, washing with methanol. The filtrate was then concentrated in vacuo. The residue was suspended in ethyl acetate and stirred for 2 hours. The suspension was filtered and the solid was dried under vacuo to afford 2-(2-aminoethyl)-N-methyl-1-(2-oxo-1,2,3,4-tetrahydroquinolin-6-yl)-1H-benzo[d]imidazole-5-carboxamide (40 mg, 87%) as a light brown solid. MS (ISP): 364.0 ([M+H]$^+$).

Example 19

Methyl 4-((2-oxo-1,2,3,4-tetrahydroquinolin-6-yl)amino)benzoate

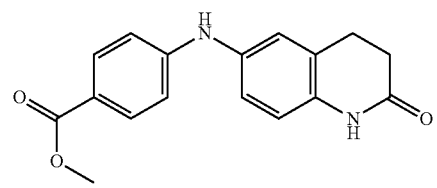 [SMILES: COC(=O)c1ccc(Nc2ccc3c(c2)CCC(=O)N3)cc1]

To a solution of 6-bromo-3,4-dihydroquinolin-2(1H)-one (CAS 3279-90-1) (50 mg) and methyl 4-aminobenzoate (CAS 619-45-4) (43.5 mg) in toluene (1 ml) were added sequentially under argon tris(dibenzylidineacetone)dipalladium (3.04 mg), 2-dicyclohexylphosphino-2',4',6'-triisopropylbiphenyl (5.27 mg) and sodium tert-butoxide (31.9 mg). The reaction mixture was stirred at 100° C. for 1 hour. After cooling to room temperature, the reaction mixture was diluted with ethyl acetate and washed with water. The organic layer was dried over sodium sulfate, filtered and concentrated in vacuo. The residue was purified by chromatography (silica gel, eluent: 0 to 10% of methanol in dichloromethane) to afford methyl 4-((2-oxo-1,2,3,4-tetrahydroquinolin-6-yl)amino)benzoate (25.8 mg, 39.4%) as a light yellow solid. MS (ISP): 297.2 ([M+H]$^+$).

Example 20

N-Methyl-2-(morpholine-4-carbonyl)-1-(2-oxo-1,2,3,4-tetrahydroquinolin-6-yl)-1H-benzo[d]imidazole-5-carboxamide

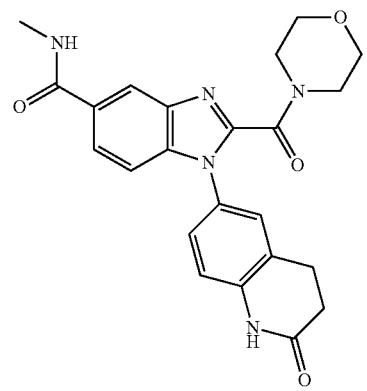 [SMILES: CNC(=O)c1ccc2c(c1)nc(C(=O)N1CCOCC1)n2-c1ccc2c(c1)CCC(=O)N2]

To a stirred solution of ethyl 5-(methylcarbamoyl)-1-(2-oxo-1,2,3,4-tetrahydroquinolin-6-yl)-1H-benzo[d]imidazole-2-carboxylate (22 mg) in dioxane (572 µl) at room temperature under argon was added a solution of 2 M triethylaluminium in toluene (112 µl). After stirring at room temperature for 10 minutes, morpholine (19.5 mg) was added and the reaction mixture was then stirred at 95° C. for 1 hour. According to LC-MS, the reaction was finished. The reaction mixture was carefully quenched with water (0.5 ml), and the solvent was then concentrated in vacuo. The residue was purified by chromatography (silica gel, eluent: 0 to 10% of methanol in dichloromethane) to afford N-methyl-2-(morpholine-4-carbonyl)-1-(2-oxo-1,2,3,4-tetrahydroquinolin-6-yl)-1H-benzo[d]imidazole-5-carboxamide (19 mg, 78.2%) as a light yellow solid. MS (ISP): 434.2 ([M+H]$^+$).

Example 21

(RS)—N-(7-Oxo-5,6,7,8-tetrahydro-1,8-naphthyridin-3-yl)-1,2,3,4-tetrahydronaphthalene-1-carboxamide

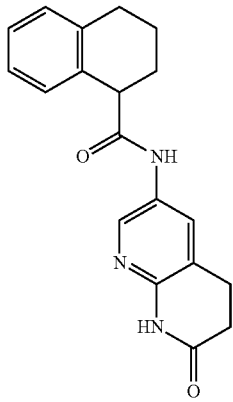 [SMILES: O=C1CCc2cc(NC(=O)C3CCCc4ccccc43)cnc2N1]

The title compound was obtained in analogy to example 5 using 6-amino-3,4-dihydro-1,8-naphthyridin-2(1H)-one (CAS 1378866-33-1) in place of 6-amino-3,4-dihydroquinolin-2(1H)-one and 1,2,3,4-tetrahydronaphthalene-1-carboxylic acid (CAS 1914-65-4) in place of 2-(1-methyl-1H-imidazol-5-yl)quinoline-4-carboxylic acid. White solid. MS (ISP): 322.2 ([M+H]$^+$).

Example 22

Methyl 2-(2-methoxypyridin-4-yl)-1-(2-oxo-1,2,3,4-tetrahydroquinolin-6-yl)-1H-benzo[d]imidazole-5-carboxylate

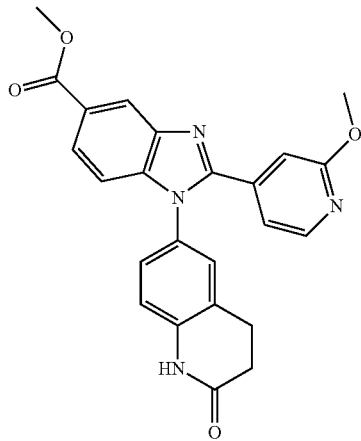 [SMILES: COC(=O)c1ccc2c(c1)nc(-c1ccnc(OC)c1)n2-c1ccc2c(c1)CCC(=O)N2]

The title compound was obtained in analogy to example 2 steps a-c using 2-methoxyisonicotinaldehyde in place of 2-(1-methyl-1H-imidazol-5-yl)quinoline-4-carbaldehyde in step c. Light brown solid. MS (ISP): 429.2 ([M+H]$^+$).

Example 23

2-(6-Methoxypyridin-2-yl)-N-methyl-1-(2-oxo-1,2,3,4-tetrahydroquinolin-6-yl)-1H-benzo[d]imidazole-5-carboxamide

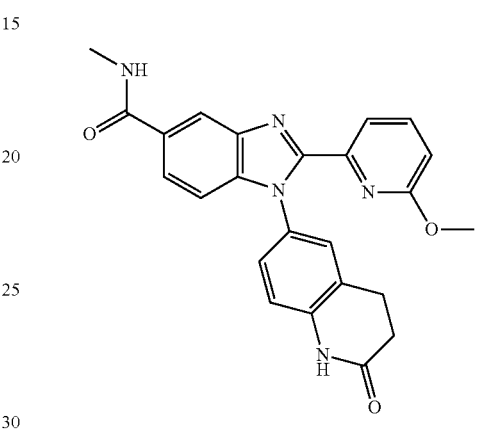

The title compound was obtained in analogy to example 6 using 6-methoxypicolinaldehyde (CAS 269058-49-3) in place of 2-phenylacetaldehyde in step c. Light yellow solid. MS (ISP): 428.4 ([M+H]$^+$).

Example 24

2-(6-Methoxypyridin-3-yl)-N-methyl-1-(2-oxo-1,2,3,4-tetrahydroquinolin-6-yl)-1H-benzo[d]imidazole-5-carboxamide

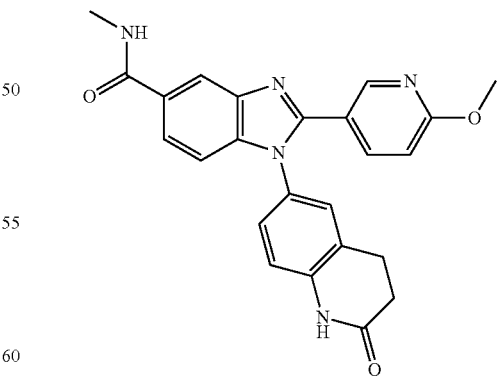

The title compound was obtained in analogy to example 6 using 6-methoxynicotinaldehyde (CAS 65873-72-5) in place of 2-phenylacetaldehyde in step c. Light yellow solid. MS (ISP): 428.3 ([M+H]$^+$).

Example 25

2-(4-Methoxypyridin-2-yl)-N-methyl-1-(2-oxo-1,2,3,4-tetrahydroquinolin-6-yl)-1H-benzo[d]imidazole-5-carboxamide

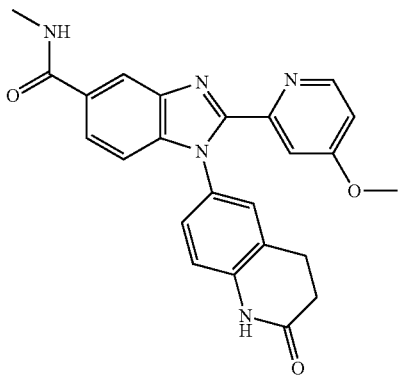

The title compound was obtained in analogy to example 6 using 4-methoxypicolinaldehyde (CAS 16744-81-3) in place of 2-phenylacetaldehyde in step c. Light yellow solid. MS (ISP): 428.3 ([M+H]$^+$).

Example 26

2-(2-Methoxypyridin-3-yl)-N-methyl-1-(2-oxo-1,2,3,4-tetrahydroquinolin-6-yl)-1H-benzo[d]imidazole-5-carboxamide

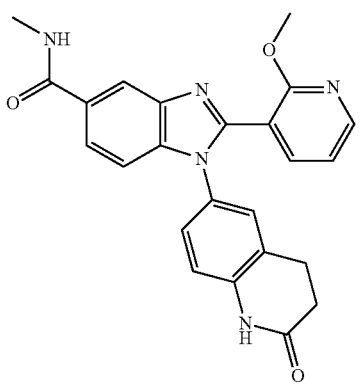 [SMILES: CNC(=O)c1ccc2c(c1)nc(-c1cccnc1OC)n2-c1ccc2c(c1)CCC(=O)N2]

The title compound was obtained in analogy to example 6 using 2-methoxynicotinaldehyde (CAS 71255-09-9) in place of 2-phenylacetaldehyde in step c. Light yellow solid. MS (ISP): 428.3 ([M+H]$^+$).

Example 27

6-(5-(4-Methoxyphenyl)-1H-imidazol-1-yl)-3,4-dihydroquinolin-2(1H)-one

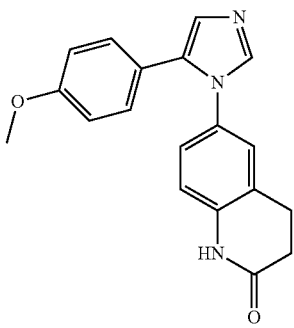 [SMILES: COc1ccc(-c2cncn2-c2ccc3c(c2)CCC(=O)N3)cc1]

The title compound was obtained in analogy to example 14 using 5-(4-methoxyphenyl)-1H-imidazole (CAS 35512-31-3) in place of 5-phenyl-1H-imidazole in step c. Light brown solid. MS (ISP): 434.2 ([M+H]$^+$).

Example 28

2-Isopropyl-N-methyl-1-(7-oxo-6,8-dihydro-5H-1,8-naphthyridin-3-yl)benzimidazole-5-carboxamide

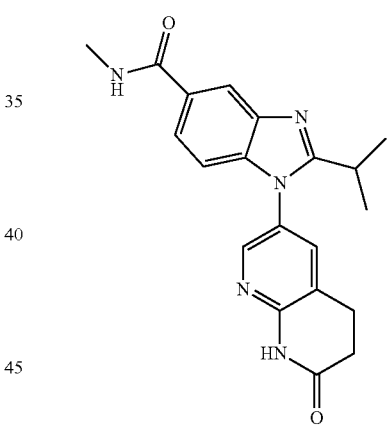

a) Methyl 3-nitro-4-[(7-oxo-6,8-dihydro-5H-1,8-naphthyridin-3-yl)amino]benzoate

To a solution of 6-amino-3,4-dihydro-1H-1,8-naphthyridin-2-one (1.1 g) in N-methyl-2-pyrrolidinone (15 ml) were added methyl 4-fluoro-3-nitro-benzoate (0.68 g) and N,N-diisopropylethylamine (1.2 ml). The mixture was stirred at 120° C. for 12 hours. The reaction mixture was cooled to 20° C., and was then poured into water. The solid obtained was filtered, and the filter cake was washed with ethyl acetate and dried in vacuo to afford methyl 3-nitro-4-[(7-oxo-6,8-dihydro-5H-1,8-naphthyridin-3-yl)amino]benzoate (320 mg, 24.5%) as a brown solid. MS (ISP): 343.1 ([M+H]$^+$).

b) Methyl 3-amino-4-[(7-oxo-6,8-dihydro-5H-1,8-naphthyridin-3-yl)amino]benzoate

To a stirred solution of methyl 3-nitro-4-[(7-oxo-6,8-dihydro-5H-1,8-naphthyridin-3-yl)amino]benzoate (360 mg) in methanol (10 ml) was added 10% palladium on charcoal (100 mg). The reaction mixture was stirred at room temperature under an atmosphere of hydrogen for 12 hours. The reaction mixture was filtered, washing with N,N-dimethylformamide. The filtrate was then concentrated in vacuo to afford methyl 3-amino-4-[(7-oxo-6,8-dihydro-5H-1,8-naphthyridin-3-yl)amino]benzoate (280 mg, 89%) as a brown solid. MS (ISP): 343.1 ([M+H]$^+$).

c) Methyl 2-isopropyl-1-(7-oxo-6,8-dihydro-5H-1,8-naphthyridin-3-yl)benzimidazole-5-carboxylate To a solution of methyl 3-amino-4-[(7-oxo-6,8-dihydro-5H-1,8-naphthyridin-3-yl)amino]benzoate (130 mg) and isobutyraldehyde (CAS 78-84-2) (28.21 mg) in DMF (6 ml) was added sodium metabisulfite (81.8 mg). The reaction mixture was stirred at 110° C. for 1 hour. The mixture was poured into water and extracted with ethyl acetate (3×10 ml). The combined organic layer was concentrated in vacuo to afford methyl 2-isopropyl-1-(7-oxo-6,8-dihydro-5H-1,8-naphthyridin-3-yl)benzimidazole-5-carboxylate (140 mg, 87.8%) as a yellow oil. MS (ISP): 365.1 ([M+H]$^+$).

d) 2-Isopropyl-1-(7-oxo-6,8-dihydro-5H-1,8-naphthyridin-3-yl)benzimidazole-5-carboxylic acid Methyl 2-isopropyl-1-(7-oxo-6,8-dihydro-5H-1,8-naphthyridin-3-yl)benzimidazole-5-carboxylate (120 mg) was dissolved in a 1:1 mixture of THF/1 M aqueous lithium hydroxide solution (8.0 ml). After stirring at 15° C. for 3 hours, the reaction mixture was extracted three times with ethyl acetate. The aqueous layer was adjusted to pH 2 by addition of 1 N aq. HCl and was then concentrated in vacuo before purification with preparative HPLC to afford 2-isopropyl-1-(7-oxo-6,8-dihydro-5H-1,8-naphthyridin-3-yl)benzimidazole-5-carboxylic acid (17.8 mg, 17%) as a yellow solid. MS (ISP): 351.2 ([M+H]$^+$).

e) 2-Isopropyl-N-methyl-1-(7-oxo-6,8-dihydro-5H-1,8-naphthyridin-3-yl)benzimidazole-5-carboxamide To a mixture of -isopropyl-1-(7-oxo-6,8-dihydro-5H-1,8-naphthyridin-3-yl)benzimidazole-5-carboxylic acid (100 mg) and HATU (67.72 mg) in DMF (5 ml) were added N,N-diisopropylethylamine (0.08 ml) and methylamine (CAS 74-89-5) (0.15 ml). The reaction mixture was stirred at 15° C. for 12 hours. The mixture was poured into water and extracted with ethyl acetate (3×10 ml). The combined organic layers were concentrated and purified by preparative HPLC to afford 2-isopropyl-N-methyl-1-(7-oxo-6,8-dihydro-5H-1,8-naphthyridin-3-yl)benzimidazole-5-carboxamide (16.8 mg, 31.1%) as a yellow solid. MS (ISP): 364.4 ([M+H]$^+$).

Example 29

2-(2-Methoxy-4-pyridyl)-N-methyl-1-(7-oxo-6,8-dihydro-5H-1,8-naphthyridin-3-yl)benzimidazole-5-carboxamide

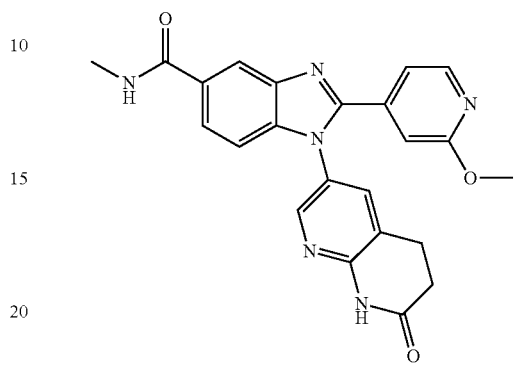

a) N-Methyl-3-nitro-4-[(7-oxo-6,8-dihydro-5H-1,8-naphthyridin-3-yl)amino]benzamide To a solution of 6-amino-3,4-dihydro-1H-1,8-naphthyridin-2-one (1.0 g) in N-methyl-2-pyrrolidinone (5 ml) were added 4-fluoro-N-methyl-3-nitro-benzamide (0.78 g) and N,N-diisopropylethylamine (1.4 ml). The mixture was stirred at 120° C. for 12 hours. The reaction mixture was then cooled to 20° C. and poured into water. The resulting solid was collected by filtration, and the filter cake was washed with ethyl acetate and dried in vacuo to afford N-methyl-3-nitro-4-[(7-oxo-6,8-dihydro-5H-1,8-naphthyridin-3-yl)amino]benzamide (290 mg, 19.7%) as a brown solid. MS (ISP): 342.1 ([M+H]$^+$).

b) 3-Amino-N-methyl-4-[(7-oxo-6,8-dihydro-5H-1,8-naphthyridin-3-yl)amino]benzamide To a stirred solution of N-methyl-3-nitro-4-[(7-oxo-6,8-dihydro-5H-1,8-naphthyridin-3-yl)amino]benzamide (290 mg) in methanol (6 ml) was added 10% palladium on charcoal (100 mg). The reaction mixture was stirred at room temperature under an atmosphere of hydrogen for 12 hours. The reaction mixture was filtered, washing with N,N-dimethylformamide. The filtrate was then concentrated in vacuo to afford 3-amino-N-methyl-4-[(7-oxo-6,8-dihydro-5H-1,8-naphthyridin-3-yl)amino]benzamide (180 mg, 63.7%) as a brown solid. MS (ISP): 312.3 ([M+H]$^+$).

c) 2-(2-Methoxy-4-pyridyl)-N-methyl-1-(7-oxo-6,8-dihydro-5H-1,8-naphthyridin-3-yl)benzimidazole-5-carboxamide To a solution of 3-amino-N-methyl-4-[(7-oxo-6,8-dihydro-5H-1,8-naphthyridin-3-yl)amino]benzamide (120 mg) and 2-methoxypyridine-4-carboxaldehyde (28.2 mg) in DMF (6 ml) was added sodium metabisulfite (109 mg). The reaction mixture was stirred at 110° C. for 1 hour. The mixture was then poured into water and extracted with ethyl acetate (3×10 ml). The combined organic layers were concentrated in vacuo and purified by preparative HPLC to afford methyl 2-(2-methoxy-4-pyridyl)-N-methyl-1-(7-oxo- 6,8-dihydro-5H-1,8-naphthyridin-3-yl)benzimidazole-5-carboxamide (63.8 mg, 38.6%) as a brown solid. MS (ISP): 429.3 ([M+H]+).

Example 30

2-(2-Acetylphenyl)-N-methyl-1-(2-oxo-3,4-dihydro-1H-quinolin-6-yl)benzimidazole-5-carboxamide

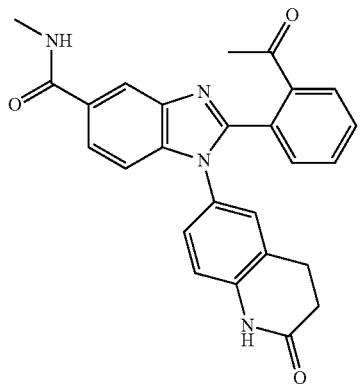 [SMILES: CNC(=O)c1ccc2c(c1)nc(-c1ccccc1C(C)=O)n2-c1ccc2c(c1)CCC(=O)N2]

To a 4 M solution of HCl in dioxane were added 3-amino-N-methyl-4-[(7-oxo-6,8-dihydro-5H-1,8-naphthyridin-3-yl)amino]benzamide (200.0 mg) and 2-acetylbenzoic acid (CAS 577-56-0) (126.95 mg). The reaction mixture was stirred at 110° C. for 12 hours and was then concentrated in vacuo and purified by preparative HPLC to afford 2-(2-acetylphenyl)-N-methyl-1-(2-oxo-3,4-dihydro-1H-quinolin-6-yl)benzimidazole-5-carboxamide (4.4 mg, 2.6%) as a white solid. MS (ISP): 439.3 ([M+H]+).

Example 31

N-Methyl-2-[2-(methylcarbamoyl)phenyl]-1-(2-oxo-3,4-dihydro-1H-quinolin-6-yl)benzimidazole-5-carboxamide

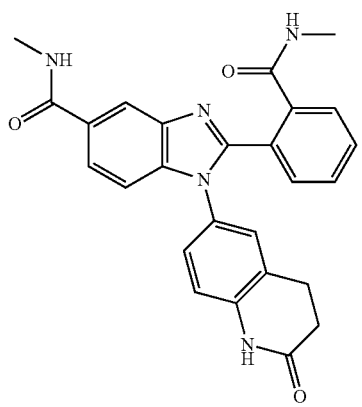 [SMILES: CNC(=O)c1ccc2c(c1)nc(-c1ccccc1C(=O)NC)n2-c1ccc2c(c1)CCC(=O)N2]

a) 2-[5-(Methylcarbamoyl)-1-(2-oxo-3,4-dihydro-1H-quinolin-6-yl)benzimidazol-2-yl]benzoic acid The title compound was obtained in analogy to example 6 using 2-formylbenzoic acid (CAS 119-67-5) in place of 2-phenylacetaldehyde in step c. Yellow oil. MS (ISP): 441.1 ([M+H]+).

b) N-Methyl-2-[2-(methylcarbamoyl)phenyl]-1-(2-oxo-3,4-dihydro-1H-quinolin-6-yl)benzimidazole-5-carboxamide The title compound was obtained in analogy to example 2 step e using 2-[5-(methylcarbamoyl)-1-(2-oxo-3,4-dihydro-1H-quinolin-6-yl)benzimidazol-2-yl]benzoic acid in place 2-[2-(3-methylimidazol-4-yl)-4-quinolyl]-1-(2-oxo-3,4-dihydro-1H-quinolin-6-yl)benzimidazole-5-carboxylic acid. White solid. MS (ISP): 454.3 ([M+H]+).

Example 32

2-(3-Methoxyphenyl)-N-methyl-1-(2-oxo-3,4-dihydro-1H-quinolin-6-yl)benzimidazole-5-carboxamide

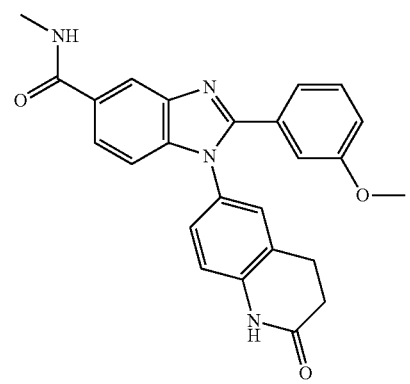

The title compound was obtained in analogy to example 6 using 3-methoxybenzaldehyde (CAS 591-31-1) in place of 2-phenylacetaldehyde in step c. White solid. MS (ISP): 427.3 ([M+H]+).

Example 33

2-(5-Methoxy-2-methyl-phenyl)-N-methyl-1-(2-oxo-3,4-dihydro-1H-quinolin-6-yl)benzimidazole-5-carboxamide

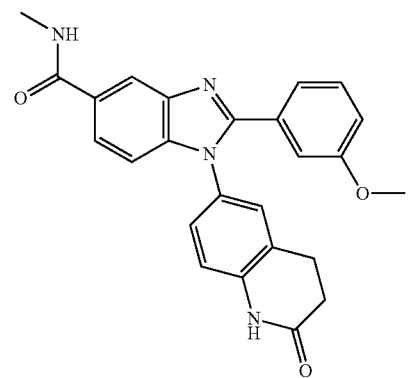

The title compound was obtained in analogy to example 6 using 5-methoxy-2-methyl-benzaldehyde (CAS 56724-09-5) in place of 2-phenylacetaldehyde in step c. White solid. MS (ISP): 441.3 ([M+H]⁺).

Example 34

2-[4-(Acetamidomethyl)phenyl]-N-methyl-1-(2-oxo-3,4-dihydro-1H-quinolin-6-yl)benzimidazole-5-carboxamide

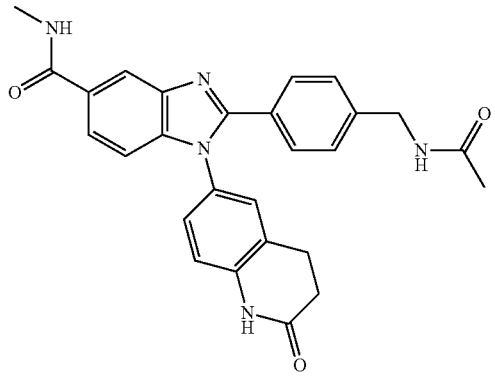 [SMILES: CNC(=O)c1ccc2c(c1)nc(-c1ccc(CNC(C)=O)cc1)n2-c1ccc2c(c1)CCC(=O)N2]

The title compound was obtained in analogy to example 6 using N-[(4-formylphenyl)methyl]acetamide (CAS 156866-50-1) in place of 2-phenylacetaldehyde in step c. White solid. MS (ISP): 468.3 ([M+H]⁺).

Example 35

2-(2-Fluoro-5-methoxy-phenyl)-N-methyl-1-(2-oxo-3,4-dihydro-1H-quinolin-6-yl)benzimidazole-5-carboxamide

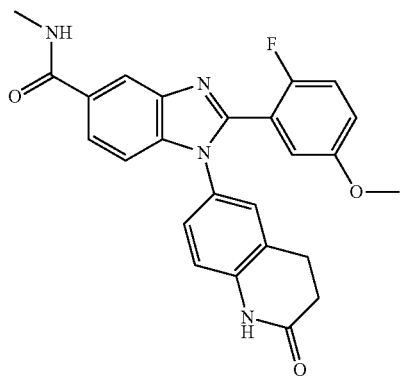

The title compound was obtained in analogy to example 6 using 2-fluoro-5-methoxybenzaldehyde (CAS 105728-90-3) in place of 2-phenylacetaldehyde in step c. White solid. MS (ISP): 445.2 ([M+H]⁺).

Example 36

2-[2-(Hydroxymethyl)phenyl]-N-methyl-1-(2-oxo-3,4-dihydro-1H-quinolin-6-yl)benzimidazole-5-carboxamide

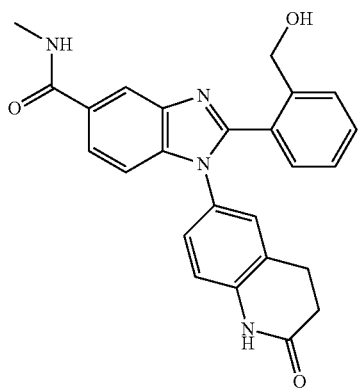 [SMILES: CNC(=O)c1ccc2c(c1)nc(-c1ccccc1CO)n2-c1ccc2c(c1)CCC(=O)N2]

a) Methyl 2-[5-(methylcarbamoyl)-1-(2-oxo-3,4-dihydro-1H-quinolin-6-yl)benzimidazol-2-yl]benzoate The title compound was obtained in analogy to example 6 using methyl 2-formylbenzoate (CAS 4122-56-9) in place of 2-phenylacetaldehyde in step c. White solid. MS (ISP): 455.1 ([M+H]⁺).

b) 2-[2-(Hydroxymethyl)phenyl]-N-methyl-1-(2-oxo-3,4-dihydro-1H-quinolin-6-yl)benzimidazole-5-carboxamide To a cooled solution of methyl 2-[5-(methylcarbamoyl)-1-(2-oxo-3,4-dihydro-1H-quinolin-6-yl)benzimidazol-2-yl] benzoate (120 mg) in THF (10 ml) at 0° C. was added dropwise DIBAL-H (0.24 ml). The reaction mixture was stirred at 15° C. for 24 hours then a solution of saturated aq. potassium sodium tartrate was added to quench the reaction and the mixture was then stirred at 15° C. for 1 hour. The suspension was filtered, and the filtrate was concentrated and purified by preparative HPLC to afford 2-[2-(hydroxymethyl)phenyl]-N-methyl-1-(2-oxo-3,4-dihydro-1H-quinolin-6-yl)benzimidazole-5-carboxamide (8 mg, 11.8%) as a yellow solid. MS (ISP): 427.3 ([M+H]⁺).

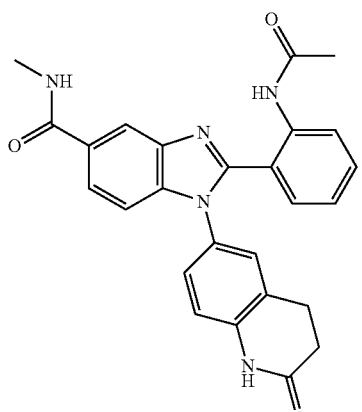

The title compound was obtained in analogy to example 6 using N-(2-formylphenyl)acetamide (CAS 13493-47-5) in place of 2-phenylacetaldehyde in step c. Yellow solid. MS (ISP): 454.0 ([M+H]+).

Example 38

2-(2-Aminophenyl)-N-methyl-1-(2-oxo-3,4-dihydro-1H-quinolin-6-yl)benzimidazole-5-carboxamide

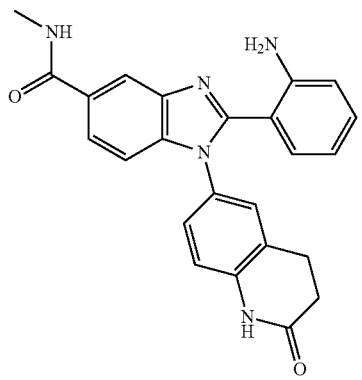

To a mixture of 2-(2-acetamidophenyl)-N-methyl-1-(2-oxo-3,4-dihydro-1H-quinolin-6-yl)benzimidazole-5-carboxamide (570 mg) in methanol (10 ml) was added cesium carbonate (148 mg). The reaction mixture was stirred at 80° C. for 36 hours and was then concentrated in vacuo and purified by preparative HPLC to afford 2-(2-aminophenyl)-N-methyl-1-(2-oxo-3,4-dihydro-1H-quinolin-6-yl)benzimidazole-5-carboxamide (15.7 mg) as a yellow solid. MS (ISP): 412.3 ([M+H]+).

Example 39

2-(4-Methoxy-6-methyl-2-pyridyl)-N-methyl-1-(2-oxo-3,4-dihydro-1H-quinolin-6-yl)benzimidazole-5-carboxamide

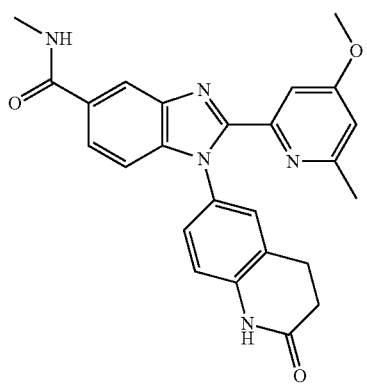 [SMILES: CNC(=O)c1ccc2c(c1)nc(-c1cc(OC)cc(C)n1)n2-c1ccc2c(c1)CCC(=O)N2]

The title compound was obtained in analogy to example 6 using 4-methoxy-6-methyl-pyridine-2-carbaldehyde (CAS 75358-79-1) in place of 2-phenylacetaldehyde in step c. Yellow solid. MS (ISP): 442.3 ([M+H]+).

Example 40

Methyl 2-[5-(methylcarbamoyl)-1-(2-oxo-3,4-dihydro-1H-quinolin-6-yl)benzimidazol-2-yl]pyridine-3-carboxylate

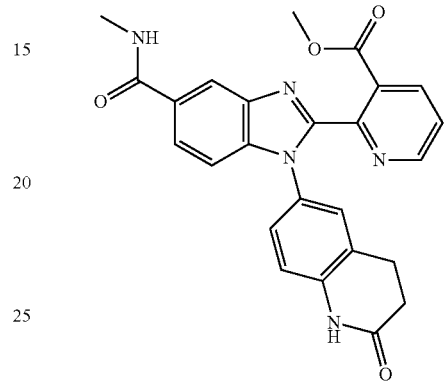

The title compound was obtained in analogy to example 6 using methyl 2-formylpyridine-3-carboxylate (CAS 25230-59-5) in place of 2-phenylacetaldehyde in step c. Yellow solid. MS (ISP): 456.3 ([M+H]+).

Example 41

Methyl 2-[[5-(methylcarbamoyl)-1-(2-oxo-3,4-dihydro-1H-quinolin-6-yl)benzimidazol-2-yl]methyl]benzoate

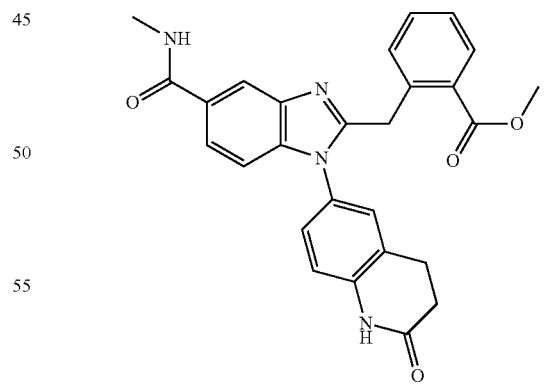

The title compound was obtained in analogy to example 6 using methyl 2-(2-oxoethyl)benzoate (CAS 62723-81-3) in place of 2-phenylacetaldehyde in step c. Yellow solid. MS (ISP): 469.2 ([M+H]+).

Example 42

2-(3-Acetamido-2-pyridyl)-N-methyl-1-(2-oxo-3,4-dihydro-1H-quinolin-6-yl)benzimidazole-5-carboxamide

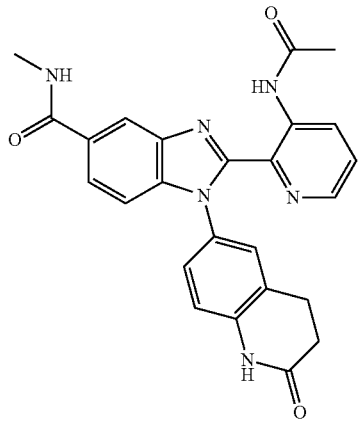 [SMILES: CNC(=O)c1ccc2c(c1)nc(-c1ncccc1NC(C)=O)n2-c1ccc2c(c1)CCC(=O)N2]

The title compound was obtained in analogy to example 6 using N-(2-formyl-3-pyridyl)acetamide (CAS 1207715-24-9) in place of 2-phenylacetaldehyde in step c. Yellow solid. MS (ISP): 455.3 ([M+H]$^+$).

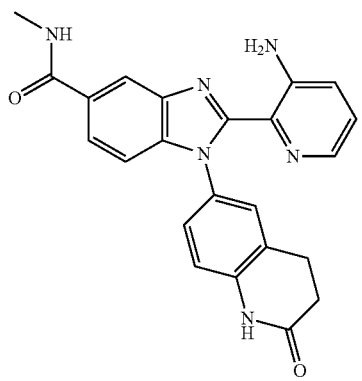 [SMILES: CNC(=O)c1ccc2c(c1)nc(-c1ncccc1N)n2-c1ccc2c(c1)CCC(=O)N2]

The title compound was obtained in analogy to example 6 using 3-aminopyridine-2-carbaldehyde (CAS 55234-58-7) in place of 2-phenylacetaldehyde in step c. Yellow solid. MS (ISP): 413.3 ([M+H]$^+$).

Example 44

2-(5-Fluoro-2-methoxy-4-pyridyl)-N-methyl-1-(2-oxo-3,4-dihydro-1H-quinolin-6-yl)benzimidazole-5-carboxamide

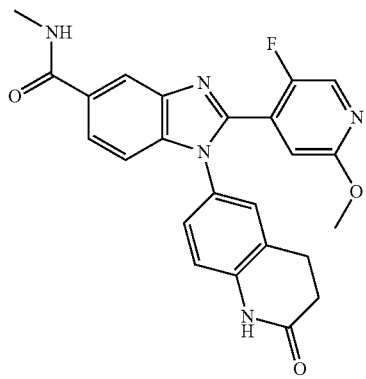 [SMILES: CNC(=O)c1ccc2c(c1)nc(-c1cc(OC)ncc1F)n2-c1ccc2c(c1)CCC(=O)N2]

The title compound was obtained in analogy to example 6 using 5-fluoro-2-methoxy-pyridine-4-carbaldehyde (CAS 884495-12-9) in place of 2-phenylacetaldehyde in step c. White solid. MS (ISP): 446.3 ([M+H]$^+$).

Example 45

N-Methyl-1-(2-oxo-3,4-dihydro-1H-quinolin-6-yl)-2-[3-(trifluoromethyl)-4-pyridyl]benzimidazole-5-carboxamide

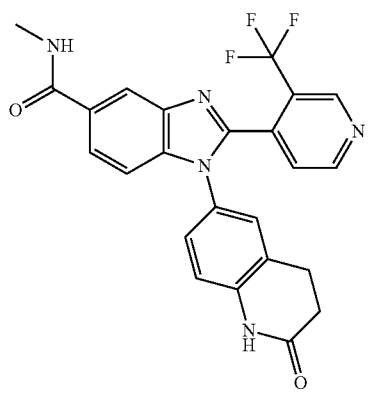 [SMILES: CNC(=O)c1ccc2c(c1)nc(-c1ccncc1C(F)(F)F)n2-c1ccc2c(c1)CCC(=O)N2]

The title compound was obtained in analogy to example 6 using 3-(trifluoromethyl)pyridine-4-carbaldehyde (CAS 1060801-92-4) in place of 2-phenylacetaldehyde in step c. Yellow solid. MS (ISP): 466.2 ([M+H]$^+$).

Example 46

2-[2-(Hydroxymethyl)-4-pyridyl]-N-methyl-1-(2-oxo-3,4-dihydro-1H-quinolin-6-yl)benzimidazole-5-carboxamide

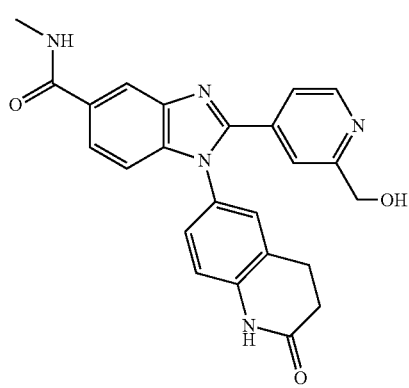 [SMILES: CNC(=O)c1ccc2c(c1)nc(-c1ccnc(CO)c1)n2-c1ccc2c(c1)CCC(=O)N2]

a) (4-Bromo-2-pyridyl)methoxy-triisopropyl-silane

To a solution of (4-bromo-2-pyridyl)methanol (CAS 131747-45-0) (1 g) and triisopropylsilyl chloride (2.05 g) in N,N-dimethylformamide (20 ml) was added imidazole (905 mg). The reaction mixture was stirred at 15° C. for 12 hours and was then quenched by addition of water. Ethyl acetate was then added. The layers were separated and the organic layer was concentrated in vacuo and purified by column chromatography (SiO$_2$, petrol ether/ethyl acetate=50:1) to afford (4-bromo-2-pyridyl)methoxy-triisopropyl-silane (2.6 g, 71%) as a colourless oil.

$^1$H NMR (400 MHZ, CDCl$_3$): δ=8.31 (d, J=5.3 Hz, 1H), 7.77 (d, J=1.0 Hz, 1H), 7.33 (dd, J=1.8, 5.3 Hz, 1H), 4.91 (s, 2H), 1.24-1.16 (m, 3H), 1.06 (s, 18H).

b) 2-(Triisopropylsilyloxymethyl)pyridine-4-carbaldehyde

To a solution of (4-bromo-2-pyridyl)methoxy-triisopropyl-silane (2.4 g) in dry THF (30 ml) was added n-BuLi solution (2.93 ml) at −70° C. under a nitrogen atmosphere. After stirring at −70° C. for 1 hour, dry N,N-dimethylformamide (0.76 ml) was added dropwise to the reaction mixture and stirring was continued at 10° C. for 2 hours. The reaction was quenched by addition of a solution of saturated aq. ammonium chloride and then the layers were separated. The organic layer was concentrated in vacuo and purified by column chromatography (SiO$_2$, petrol ether to petrol ether/ethyl acetate=10:1) to give. 2-triisopropylsilyloxymethyl)pyridine-4-carbaldehyde (460 mg, 32.1%) as a yellow oil.

c) N-Methyl-1-(2-oxo-3,4-dihydro-1H-quinolin-6-yl)-2-[2-(triisopropylsilyloxymethyl)-4-pyridyl]benzimidazole-5-carboxamide The title compound was obtained in analogy to example 6 using 2-(triisopropylsilyloxymethyl)pyridine-4-carbaldehyde in place of 2-phenylacetaldehyde in step c. Yellow oil. MS (ISP): 584.3 ([M+H]$^+$).

d) 2-[2-(Hydroxymethyl)-4-pyridyl]-N-methyl-1-(2-oxo-3,4-dihydro-1H-quinolin-6-yl)benzimidazole-5-carboxamide A solution of N-methyl-1-(2-oxo-3,4-dihydro-1H-quinolin-6-yl)-2-[2-(triisopropylsilyloxymethyl)-4-pyridyl]benzimidazole-5-carboxamide (130.0 mg) in pyridine hydrofluoride (2.0 ml) and THF (8 ml) was stirred at 15° C. for 1 hour. The mixture was adjusted to pH 8 by addition of aq. ammonium hydroxide and the layers were then separated. The organic layer was dried over Na$_2$SO$_4$, filtered, concentrated in vacuo and purified by preparative HPLC to afford 2-[2-(hydroxymethyl)-4-pyridyl]-N-methyl-1-(2-oxo-3,4-dihydro-1H-quinolin-6-yl)benzimidazole-5-carboxamide (17.2 mg, 32.9% yield) as a yellow solid. MS (ISP): 428.3 ([M+H]$^+$).

Example 47

2-[[2-Methoxy-4-(trifluoromethyl)phenyl]methyl]-N-methyl-1-(2-oxo-3,4-dihydro-1H-quinolin-6-yl)benzimidazole-5-carboxamide

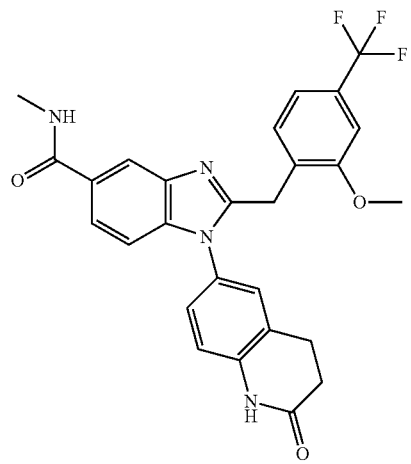

The title compound was obtained in analogy to example 6 using 2-[2-methoxy-4-(trifluoromethyl)phenyl]acetaldehyde (CAS 1823320-58-6) in place of 2-phenylacetaldehyde in step c. White solid. MS (ISP): 509.4 ([M+H]$^+$).

Example 48

2-(2-Acetyl-3-pyridyl)-N-methyl-1-(2-oxo-3,4-dihydro-1H-quinolin-6-yl)benzimidazole-5-carboxamide

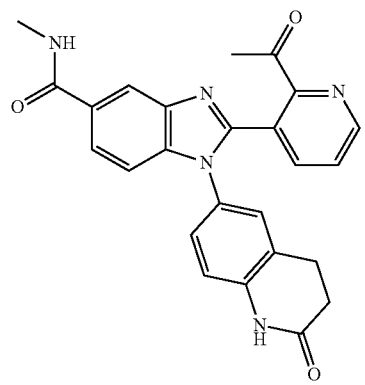 [SMILES: CNC(=O)c1ccc2c(c1)nc(-c1cccnc1C(C)=O)n2-c1ccc2c(c1)CCC(=O)N2]

a) 2-[2-(1-Ethoxyvinyl)-3-pyridyl]-N-methyl-1-(2-oxo-3,4-dihydro-1H-quinolin-6-yl)benzimidazole-5-carboxamide The title compound was obtained in analogy to example 6 using 2-(1-ethoxyvinyl)pyridine-3-carbaldehyde (CAS 2138266-81-4) in place of 2-phenylacetaldehyde in step c. Yellow oil. MS (ISP): 468.2 ([M+H]$^+$).

b) 2-(2-Acetyl-3-pyridyl)-N-methyl-1-(2-oxo-3,4-dihydro-1H-quinolin-6-yl)benzimidazole-5-carboxamide A solution of 2-[2-(1-ethoxyvinyl)-3-pyridyl]-N-methyl-1-(2-oxo-3,4-dihydro-1H-quinolin-6-yl)benzimidazole-5-carboxamide (300 mg) in a 1:2 mixture of 2 M aq. HCl/acetonitrile (12 ml) was stirred at 110° C. for 1 hour. The reaction mixture was neutralized by addition of a saturated aq. solution of NaHCO$_3$ and extracted with ethyl acetate (3×15 ml). The combined organic phases were dried over Na$_2$SO$_4$, filtered, concentrated in vacuo and purified by preparative HPLC to give 2-(2-acetyl-3-pyridyl)-N-methyl-1-(2-oxo-3,4-dihydro-1H-quinolin-6-yl)benzimidazole-5-carboxamide (20.4 mg, 26.3%) as a yellow solid. MS (ISP): 440.3 ([M+H]$^+$).

Example 49

N-Methyl-2-[3-(methylcarbamoyl)-2-pyridyl]-1-(2-oxo-3,4-dihydro-1H-quinolin-6-yl)benzimidazole-5-carboxamide

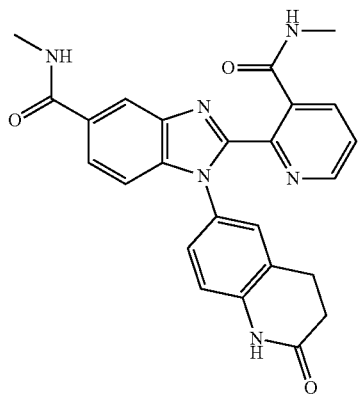 [SMILES: CNC(=O)c1ccc2c(c1)nc(-c1ncccc1C(=O)NC)n2-c1ccc2c(c1)CCC(=O)N2]

a) Methyl 2-[5-(methylcarbamoyl)-1-(2-oxo-3,4-dihydro-1H-quinolin-6-yl)benzimidazol-2-yl]pyridine-3-carboxylate The title compound was obtained in analogy to example 6 using methyl 2-formylpyridine-3-carboxylate in place of 2-phenylacetaldehyde in step c. Yellow oil. MS (ISP): 456.3 ([M+H]$^+$).

b) 2-[5-(Methylcarbamoyl)-1-(2-oxo-3,4-dihydro-1H-quinolin-6-yl)benzimidazol-2-yl]pyridine-3-carboxylic acid The title compound was obtained in analogy to example 2 step d using methyl 2-[5-(methylcarbamoyl)-1-(2-oxo-3,4-dihydro-1H-quinolin-6-yl)benzimidazol-2-yl]pyridine-3-carboxylate in place of methyl 2-[2-(3-methylimidazol-4-yl)-4-quinolyl]-1-(2-oxo-3,4-dihydro-1H-quinolin-6-yl)benzimidazole-5-carboxylate in step d. Yellow oil. MS (ISP): 442.1 ([M+H]$^+$).

c) N-Methyl-2-[3-(methylcarbamoyl)-2-pyridyl]-1-(2-oxo-3,4-dihydro-1H-quinolin-6-yl)benzimidazole-5-carboxamide The title compound was obtained in analogy to example 2 step e using 2-[5-(methylcarbamoyl)-1-(2-oxo-3,4-dihydro-1H-quinolin-6-yl)benzimidazol-2-yl]pyridine-3-carboxylic acid in place of 2-[2-(3-methylimidazol-4-yl)-4-quinolyl]-1-(2-oxo-3,4-dihydro-1H-quinolin-6-yl)benzimidazole-5-carboxylic acid. White solid. MS (ISP): 455.3 ([M+H]$^+$).

Example 50

Methyl 2-isopropyl-1-(6-oxo-7,8-dihydro-5H-1,5-naphthyridin-2-yl)benzimidazole-5-carboxylate

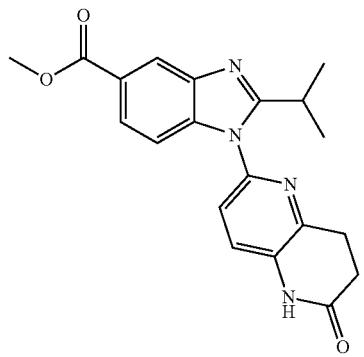 [SMILES: COC(=O)c1ccc2c(c1)nc(C(C)C)n2-c1ccc2c(n1)CCC(=O)N2]

a) Methyl 3-nitro-4-[(6-oxo-7,8-dihydro-5H-1,5-naphthyridin-2-yl)amino]benzoate To a solution of 6-chloro-3,4-dihydro-1H-1,5-naphthyridin-2-one (1.3 g) in 1,4-dioxane (40 ml) were added methyl 4-amino-3-nitro-benzoate (1.536 g), cesium carbonate (4.639 g), 4,5-bis(diphenylphosphino)-9,9-dimethylxanthene (165 mg) and tris(dibenzylideneacetone)dipalladium (0) (130 mg). The reaction mixture was stirred at 120° C. for 12 hours under a nitrogen atmosphere and then water was added. The resulting precipitate was then collected by filtration and dried in vacuo to afford methyl 3-nitro-4-[(6-oxo-7,8-dihydro-5H-1,5-naphthyridin-2-yl)amino]benzoate (800 mg, 31.2%) as a brown solid. MS (ISP): 343.1 ([M+H]$^+$).

b) 2-Isopropyl-1-(6-oxo-7,8-dihydro-5H-1,5-naphthyridin-2-yl)benzimidazole-5-carboxylic acid The title compound was obtained in analogy to example 28 steps b-d using methyl 3-nitro-4-[(6-oxo-7,8-dihydro-5H-1,5-naphthyridin-2-yl)amino]benzoate in place of methyl 3-nitro-4-[(7-oxo-6,8-dihydro-5H-1,8-naphthyridin-3-yl)amino]benzoate in step b. Brown oil. MS (ISP): 313.1 ([M+H]$^+$).

c) Methyl 2-isopropyl-1-(6-oxo-7,8-dihydro-5H-1,5-naphthyridin-2-yl)benzimidazole-5-carboxylate The title compound was obtained in analogy to example 28 using 2-isopropyl-1-(6-oxo-7,8-dihydro-5H-1,5-naphthyridin-2-yl)benzimidazole-5-carboxylic acid in place of 2-isopropyl-1-(7-oxo-6,8-dihydro-5H-1,8-naphthyridin-3-yl)benzimidazole-5-carboxylic acid in step e. White solid. MS (ISP): 365.4 ([M+H]$^+$).

Example 51

2-Isopropyl-N-methyl-1-(6-oxo-7,8-dihydro-5H-1,5-naphthyridin-2-yl)benzimidazole-5-carboxamide

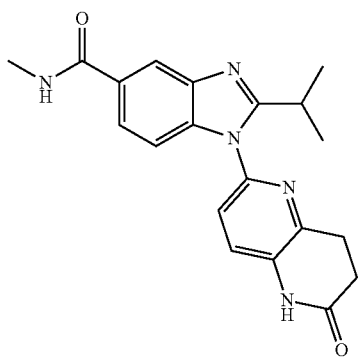 [SMILES: CNC(=O)c1ccc2c(c1)nc(C(C)C)n2-c1ccc2c(n1)CCC(=O)N2]

a) 2-Isopropyl-1-(6-oxo-7,8-dihydro-5H-1,5-naphthyridin-2-yl)benzimidazole-5-carboxylic acid The title compound was obtained in analogy to example 28 step d using methyl 2-isopropyl-1-(6-oxo-7,8-dihydro-5H-1,5-naphthyridin-2-yl)benzimidazole-5-carboxylate in place of methyl 2-isopropyl-1-(7-oxo-6,8-dihydro-5H-1,8-naphthyridin-3-yl)benzimidazole-5-carboxylate. Yellow solid. MS (ISP): 351.1 ([M+H]$^+$).

b) 2-Isopropyl-N-methyl-1-(6-oxo-7,8-dihydro-5H-1,5-naphthyridin-2-yl)benzimidazole-5-carboxamide To a solution of 2-isopropyl-1-(6-oxo-7,8-dihydro-5H-1,5-naphthyridin-2-yl)benzimidazole-5-carboxylic acid (100 mg) in DMF (5 ml) were added 1-propanephosphonic anhydride (264 mg, 0.42 mmol, triethylamine (0.12 ml) and methylamine (17.2 mg). The mixture was stirred at 20° C. for 12 hours then the reaction mixture was concentrated in vacuo and purified by preparative HPLC to give 2-isopropyl-N-methyl-1-(6-oxo-7,8-dihydro-5H-1,5-naphthyridin-2-yl)benzimidazole-5-carboxamide (22 mg, 21.9%) as a white solid. MS (ISP): 364.4 ([M+H]$^+$).

Example 52

2-Isopropyl-N,N-dimethyl-1-(6-oxo-7,8-dihydro-5H-1,5-naphthyridin-2-yl)benzimidazole-5-carboxamide

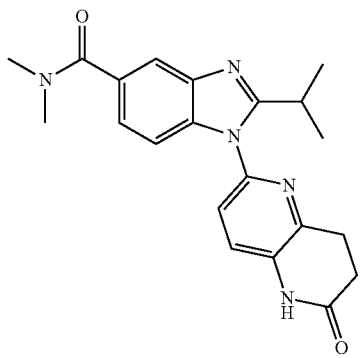 [SMILES: CC(C)c1nc2cc(C(=O)N(C)C)ccc2n1-c1ccc2c(n1)CCC(=O)N2]

The title compound was obtained in analogy to example 51 step b using dimethylamine (CAS 124-40-3) in place of methylamine. Yellow solid. MS (ISP): 378.4 ([M+H]$^+$).

Example 53

7-(1H-Imidazol-1-yl)-3,4-dihydroquinolin-2(1H)-one

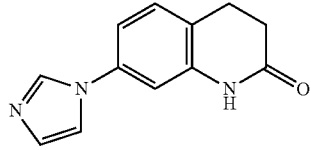 [SMILES: O=C1CCc2ccc(-n3ccnc3)cc2N1]

To a solution of 7-amino-3,4-dihydroquinolin-2(1H)-one (CAS 22246-07-7) (200 mg) in methanol (2 ml) were added ammonium acetate (190 mg), oxalaldehyde (40% solution in water, 283 µl) and formaldehyde (36% in water, 472 µl). The yellow solution was stirred at 95° C. for 4 hours. The reaction mixture was then cooled to room temperature and stirred overnight. The reaction mixture was diluted with ethyl acetate and a saturated aq. solution of sodium hydrogen carbonate and then the layers were separated. The organic layer was dried over sodium sulfate, filtered and concentrated in vacuo. The residue was purified by chromatography (silica gel, eluent: 0 to 10% of methanol in dichloromethane) to afford 7-(1H-imidazol-1-yl)-3,4-dihydroquinolin-2(1H)-one (118 mg, 44.9%) as a light yellow solid. MS (ISP): 214.2 ([M+H]$^+$).

Example 54

6-(Indoline-1-carbonyl)-3,4-dihydro-1H-quinolin-2-one

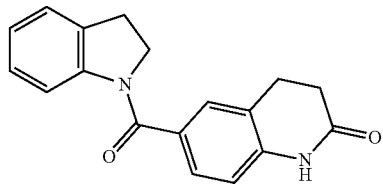 [SMILES: O=C1CCc2cc(C(=O)N3CCc4ccccc43)ccc2N1]

To a stirred solution of 1-(3-dimethylaminopropyl)-3-ethylcarbodiimide hydrochloride (902 mg) and 1-hydroxybenzotriazole (636 mg) in N,N-dimethylformamide (3 ml) were added 2-oxo-3,4-dihydro-1H-quinoline-6-carboxylic acid (CAS 88371-24-8) (300 mg) and indoline (0.23 ml) and then the reaction mixture was stirred at 25° C. for 16 hours. The reaction was diluted into water (10 ml) and extracted with ethyl acetate (2×5 ml). The combined organic phases were concentrated in vacuo and the residue was purified by preparative HPLC to give 6-(indoline-1-carbonyl)-3,4-dihydro-1H-quinolin-2-one (14.4 mg, 3%) as a yellow solid. MS (ISP): 307.2 ([M+H]$^+$).

Example 55

6-(2,3-Dihydropyrrolo[2,3-b]pyridine-1-carbonyl)-3,4-dihydro-1H-quinolin-2-one

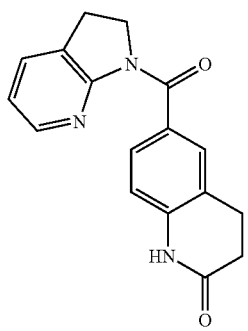 [SMILES: O=C1CCc2cc(C(=O)N3CCc4cccnc43)ccc2N1]

The title compound was obtained in analogy to example 54 using 2,3-dihydro-1H-pyrrolo[2,3-b]pyridine (CAS 1221503-20-3) in place of indoline. White solid. MS (ISP): 294.1 ([M+H]+).

Example 56

6-(3,4-Dihydro-2H-quinoline-1-carbonyl)-3,4-dihydro-1H-quinolin-2-one

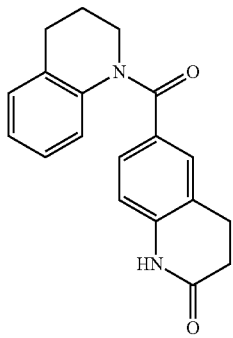 [SMILES: O=C1CCc2cc(C(=O)N3CCCc4ccccc43)ccc2N1]

To a stirred solution of 2-oxo-3,4-dihydro-1H-quinoline-6-carboxylic acid (300 mg) and 1,2,3,4-tetrahydroquinoline (CAS 635-46-1) (0.3 ml) in acetonitrile (5 ml) at 0° C. were added sequentially 3-methylpyridine (731 mg) and methanesulfonyl chloride (360 mg). The reaction mixture was warmed to 25° C. and stirred at 25° C. for 16 hours. The solution was diluted with water (5 ml) and was extracted with ethyl acetate (3×5 ml). The combined organic phases were dried over anhydrous Na$_2$SO$_4$, filtered, and concentrated in vacuo. The crude product was purified by preparative HPLC to afford 6-(3,4-dihydro-2H-quinoline-1-carbonyl)-3,4-dihydro-1H-quinolin-2-one as a yellow solid. MS (ISP): 293.1 ([M+H]+)

Example 57

N-(1-Acetyl-4-piperidyl)-2-oxo-3,4-dihydro-1H-quinoline-6-carboxamide

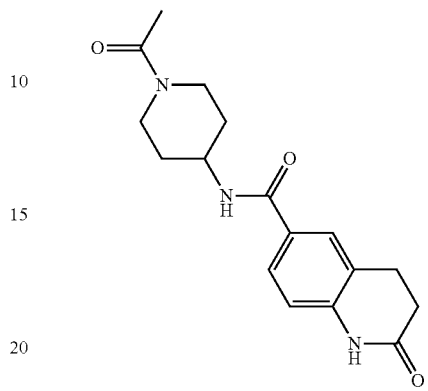

The title compound was obtained in analogy to example 54 using 1-acetyl-4-amino-piperidine (CAS 160357-94-8) in place of indoline. White solid. MS (ISP): 316.2 ([M+H]+).

Example 58

6-(Indoline-1-carbonyl)-3,4-dihydro-1H-1,8-naphthyridin-2-one

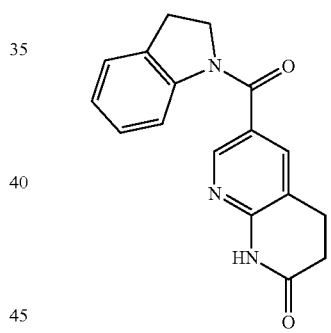

a) 7-Oxo-6,8-dihydro-5H-1,8-naphthyridine-3-carboxylic acid

Methyl 7-oxo-6,8-dihydro-5H-1,8-naphthyridine-3-carboxylate (CAS 1822623-53-9) (800 mg) and lithium hydroxide (185 mg) were dissolved in a 1:1 mixture of THF/water (16.0 ml). After stirring at 15° C. for 3 hours, the reaction mixture was extracted twice with ethyl acetate. The aqueous layer was adjusted to pH 2 by addition of 1 N aq. HCl and then extracted with ethyl acetate. The organic layer was separated, dried over Na$_2$SO$_4$, and concentrated in vacuo to afford 7-oxo-6,8-dihydro-5H-1,8-naphthyridine-3-carboxylic acid (200 mg, 24.8%) as a yellow oil. MS (ISP): 193.1 ([M+H]+).

b) 6-(Indoline-1-carbonyl)-3,4-dihydro-1H-1,8-naphthyridin-2-one

The title compound was obtained in analogy to example 54 using 7-oxo-6,8-dihydro-5H-1,8-naphthyridine-3-carboxylic acid in place of added 2-oxo-3,4-dihydro-1H-quinoline-6-carboxylic acid. Yellow solid. MS (ISP): 294.2 ([M+H]⁺).

Example 59

6-(2,3-Dihydropyrrolo[2,3-b]pyridine-1-carbonyl)-3,4-dihydro-1H-1,8-naphthyridin-2-one

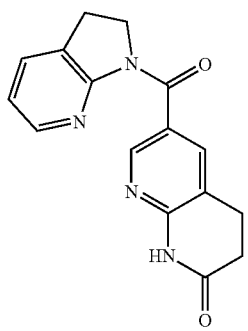

The title compound was obtained in analogy to example 54 using 2,3-dihydro-1H-pyrrolo[2,3-b]pyridine in place of indoline and 7-oxo-6,8-dihydro-5H-1,8-naphthyridine-3-carboxylic acid in place of 2-oxo-3,4-dihydro-1H-quinoline-6-carboxylic acid. White solid. MS (ISP): 295.2 ([M+H]⁺).

Example 60

6-(3,4-Dihydro-2H-quinoline-1-carbonyl)-3,4-dihydro-1H-1,8-naphthyridin-2-one

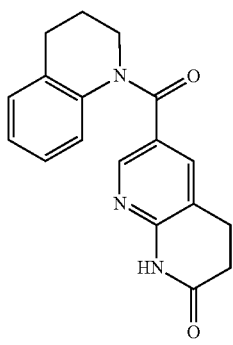

The title compound was obtained in analogy to example 56 using 7-oxo-6,8-dihydro-5H-1,8-naphthyridine-3-carboxylic acid in place of 2-oxo-3,4-dihydro-1H-quinoline-6-carboxylic acid. Yellow solid. MS (ISP): 308.2 ([M+H]⁺).

Example 61

6-(2-Isopropyl-1H-benzo[d]imidazol-1-yl)-3,4-dihydroquinazolin-2(1H)-one

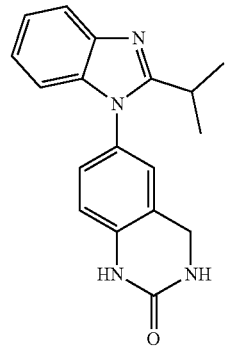 [SMILES: CC(C)c1nc2ccccc2n1-c1ccc2c(c1)CNC(=O)N2]

The title compound was obtained in analogy to example 6 using 1-fluoro-2-nitrobenzene in place of 4-fluoro-N-methyl-3-nitrobenzamide and 6-amino-3,4-dihydroquinazolin-2(1H)-one (CAS 1260835-29-7) in place of 6-amino-3,4-dihydroquinolin-2(1H)-one in step a, and isobutyraldehyde in place of 2-phenylacetaldehyde in step c. White solid. MS (ISP): 307.2 ([M+H]⁺).

Example 62

2-Isopropyl-N-methyl-1-(2-oxo-1,2,3,4-tetrahydroquinazolin-6-yl)-1H-benzo[d]imidazole-5-carboxamide

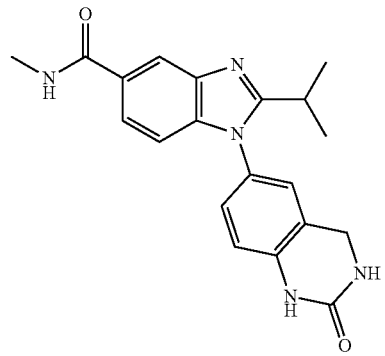 [SMILES: CNC(=O)c1ccc2c(c1)nc(C(C)C)n2-c1ccc2c(c1)CNC(=O)N2]

The title compound was obtained in analogy to example 6 using 6-amino-3,4-dihydroquinazolin-2(1H)-one in place of 6-amino-3,4-dihydroquinolin-2(1H)-one in step a, and isobutyraldehyde in place of 2-phenylacetaldehyde in step c. Light yellow solid. MS (ISP): 364.2 ([M+H]⁺).

Example A

N-(10-(2-(((6S)-4-(4-Chlorophenyl)-2,3,9-trimethyl-6H-thieno[3,2-f][1,2,4]triazolo[4,3-a][1,4]diazepin-6-yl)acetamido)decyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide

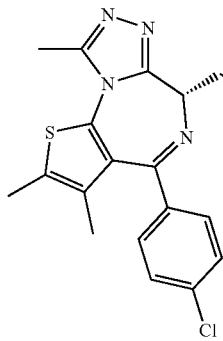
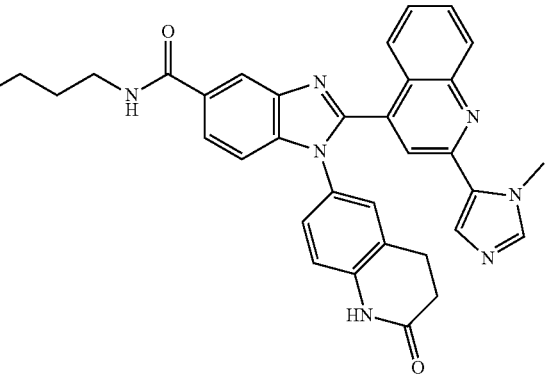

a) tert-Butyl (10-(2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamido)decyl)carbamate To 2-(2-(1-methyl-1H-imidazol-5-yl)quinolin-4-yl)-1-(2-oxo-1,2,3,4-tetrahydroquinolin-6-yl)-1H-benzo[d]imidazole-5-carboxylic acid (70 mg) were added sequentially HATU (556 µl, 0.27 M solution in DMF), tert-butyl (5-aminopentyl)carbamate (CAS 51644-96-3) (35.8 mg) and N,N-diisopropylethylamine (95 µl). The brown solution was stirred at room temperature for 19 h. The reaction mixture was purified by reversed phase HPLC. The fractions were collected and lyophilised to afford tert-butyl (10-(2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamido)decyl)carbamate as a white foam (27 mg, 28%). MS (ISP): 769.9 ([M+H]$^+$).

b) N-(10-Aminodecyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide hydrochloride To a stirred solution of tert-butyl (10-(2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamido)decyl)carbamate (40 mg, 52 µmol, Eq: 1) in EtOAc (500 µl) was added a solution of 4 M HCl in dioxane (780 µl). The reaction mixture was stirred at room temperature for 3 hours. LC/MS analysis indicated that the reaction was finished. The solvent was evaporated to afford N-(10-aminodecyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide hydrochloride as a light yellow foam (34.8 mg, 95%) which was used in the next step without further purification. MS (ISP): 670 ([M+H]$^+$).

c) N-(10-(2-((6S)-4-(4-Chlorophenyl)-2,3,9-trimethyl-6H-thieno[3,2-f][1,2,4]triazolo[4,3-a][1,4]diazepin-6-yl)acetamido)decyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide To a mixture of N-(10-aminodecyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide hydrochloride (34.8 mg) and (S)-2-(4-(4-chlorophenyl)-2,3,9-trimethyl-6H-thieno[3,2-f][1,2,4]triazolo[4,3-a][1,4]diazepin-6-yl)acetic acid (23.7 mg) were added HATU (202 µl, 0.27 M solution in DMF) and N,N-diisopropylethylamine (34.5 µl). The reaction mixture was shaken at room temperature for 2 hours. LC/MS analysis indicated that the reaction was finished. The reaction mixture was purified by reversed phase HPLC. The fractions were collected and lyophilised. The resulting foam was stirred in diethyl ether, and the ensuing crystals were collected by filtration and dried in vacuo to afford N-(10-(2-((6S)-4-(4-chlorophenyl)-2,3,9-trimethyl-6H-thieno[3,2-f][1,2,4]triazolo[4,3-a][1,4]diazepin-6-yl)acetamido)decyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide as a white solid (17 mg, 31%). MS (ISP): 1051.4 ([M+H]$^+$).

Example B

N-(5-(2-(((6S)-4-(4-Chlorophenyl)-2,3,9-trimethyl-6H-thieno[3,2-f][1,2,4]triazolo[4,3-a][1,4]diazepin-6-yl)acetamido)pentyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide

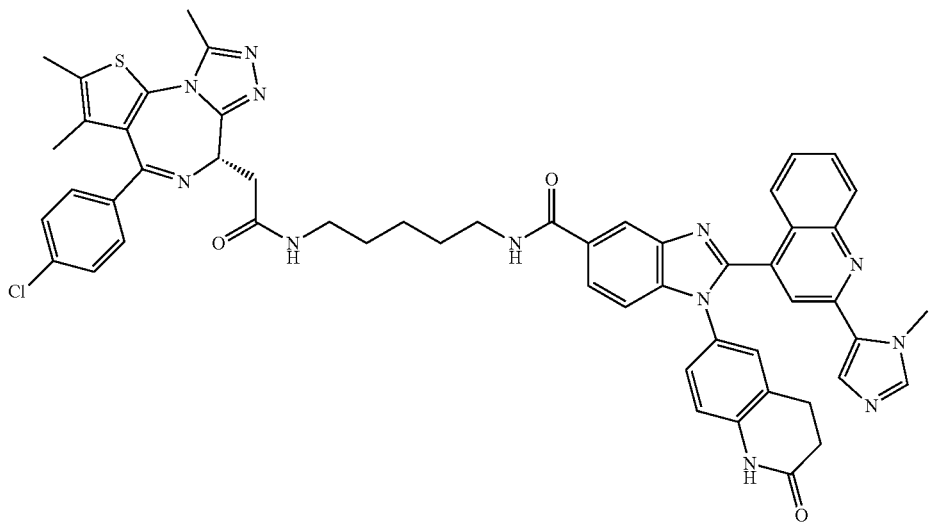 [SMILES: Cc1sc2c(c1C)C(c1ccc(Cl)cc1)=N[C@@H](CC(=O)NCCCCCNC(=O)c1ccc3c(c1)nc(-c1cc(-c4cncn4C)nc4ccccc14)n3-c1ccc3c(c1)CCC(=O)N3)c1nnc(C)n1-2]

a) tert-Butyl (5-(2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamido)pentyl) carbamate The title compound was obtained in analogy to example A using tert-butyl (10-aminodecyl)carbamate (CAS 216961-61-4) in place of tert-butyl (5-aminopentyl)carbamate in step a. Off-white foam. MS (ISP): 699.5 ([M+H]$^+$).

b) N-(5-Aminopentyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide hydrochloride The title compound was obtained in analogy to example A using tert-butyl (5-(2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamido)pentyl)carbamate in place of tert-butyl (10-(2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamido)decyl)carbamate in step b. Off-white foam. MS (ISP): 599.4 ([M+H]$^+$).

c) N-(5-(2-(((6S)-4-(4-Chlorophenyl)-2,3,9-trimethyl-6H-thieno[3,2-f][1,2,4]triazolo[4,3-a][1.4]diazepin-6-yl)acetamido)pentyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide To a mixture of N-(5-aminopentyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide hydrochloride (34 mg) and 2-((6S)-4-(4-chlorophenyl)-2,3,9-trimethyl-6H-thieno[3,2-f][1,2,4]triazolo[4,3-a][1,4]diazepin-6-yl)acetic acid (27.3 mg) were added HATU (202 µl, 0.27 M solution in DMF) and N,N-diisopropylethylamine (34.5 µl). The reaction mixture was shaken at room temperature for 2 hours. LC/MS analysis indicated that the reaction was finished. The reaction mixture was then transferred to a separating funnel. Ethyl acetate/TBME (1:1) and water were added to give a sticky solid. After removal of the aqueous and organic layers, the sticky solid was recovered by dissolving in CH$_2$Cl$_2$. The organic phase was dried over MgSO$_4$, filtered, and concentrated in vacuo. The crude material was purified by flash chromatography (silica gel, 10 g, eluent: 0 to 10% of methanol in dichloromethane) to afford N-(5-(2-(((6S)-4-(4-chlorophenyl)-2,3,9-trimethyl-6H-thieno[3,2-f][1,2,4]triazolo[4,3-a][1,4]diazepin-6-yl)acetamido)pentyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide as an off-white solid (27 mg, 51%). MS (ISP): 981.4 ([M+H]$^+$).

Example C

N-(2-(2-(2-(2-((6S)-4-(4-Chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide

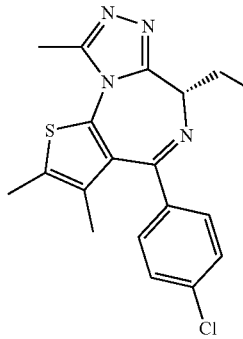

a) (2S,4R)-1-((S)-2-Acetamido-3,3-dimethylbutanoyl)-4-hydroxy-N—((S)-2-hydroxy-2-phenylethyl)pyrrolidine-2-carboxamide The title compound was obtained in analogy to example A using tert-butyl (2-(2-(2-aminoethoxy)ethoxy)ethyl)carbamate (CAS 153086-78-3) in place of tert-butyl (5-aminopentyl)carbamate in step a. White foam. MS (ISP): 745.45 ([M+H]$^+$).

b) N-(2-(2-(2-Aminoethoxy)ethoxy)ethyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide hydrochloride The title compound was obtained in analogy to example A using tert-butyl (2-(2-(2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamido)ethoxy)ethoxy)ethyl)carbamate in place of tert-butyl (10-(2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamido)decyl)carbamate in step b. Off-white foam. MS (ISP): 645.48 ([M+H]$^+$).

c) N-(2-(2-(2-(2-((6S)-4-(4-Chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide To a mixture of N-(2-(2-(2-aminoethoxy)ethoxy)ethyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide hydrochloride (44 mg) and 2-((6S)-4-(4-chlorophenyl)-2,3,9-trimethyl-6H-thieno[3,2-f][1,2,4]triazolo[4,3-a][1,4]diazepin-6-yl)acetic acid (32 mg) were added HATU (264 μl, 0.27 M solution in DMF) and N,N-diisopropylethylamine (44.1 μl). The reaction mixture was shaken at room temperature for 2 hours. LC/MS analysis indicated that the reaction was finished. The reaction mixture was partioned between dichloromethane and water. The organic phase was separated, dried over MgSO$_4$, filtered, and concentrated in vacuo. The crude material was purified by flash chromatography (silica gel, 10 g, eluent: 0 to 10% of methanol in dichloromethane) to afford N-(2-(2-(2-(2-((6S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)-2-(2-(1-methyl-1H-imidazol-5-yl)quinolin-4-yl)-1-(2-oxo-1,2,3,4-tetrahydroquinolin-6-yl)-1H-benzo[d]imidazole-5-carboxamide as an off-white solid (11.7 mg, 18%). MS (ISP): 1027.4 ([M+H]$^+$).

Although the foregoing invention has been described in some detail by way of illustration and example for purposes of clarity and understanding, it will be readily apparent to one of ordinary skill in the art in light of the teachings of this invention that certain changes and modifications may be made thereto without departing from the spirit or scope of the invention as defined in the appended claims.

We claim:

1. A method for the treatment of cancer comprising administering an effective amount of a compound of formula:

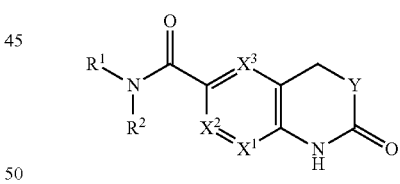

or a pharmaceutically acceptable salt thereof to a patient in need thereof;
wherein
$X^1$ is CH or N;
$X^2$ is CH or N;
$X^3$ is CH or N,
wherein one of $X^1$, $X^2$ or $X^3$ is N and the other two are CH;
$R^1$ is selected from the group consisting of
  i) —C(=O)—$R^6$;
  ii) heterocyclyl;
  iii) heterocyclyl, substituted by 1 or 2 substituents individually selected from $R^{10}$;
  iv) aryl; and
  v) aryl, substituted by 1 or 2 substituents individually selected from $R^9$;

$R^2$ is H, or $R^1$ and $R^2$ together with the nitrogen they are attached to form a heteroaryl, which is optionally substituted by 1 or 2 substituents individually selected from $R^3$;

$R^3$ is selected from the group consisting of:
i) —$(CH_2)_{0-1}$-aryl substituted by 1 or 2 substituents selected from $R^4$;
ii) —$(CH_2)_{0-2}$—$N(R^{3c})C(=O)$—$C_{3-7}$cycloalkyl;
iii) amino-$C_{1-6}$alkyl;
iv) —$C(=O)N(R^{3a},R^{3b})$;
v) $C(=O)O$—$C_{1-6}$alkyl;
vi) $C_{1-6}$alkyl; and
vii) —$C_{3-7}$cycloalkyl;

$R^{3a}$ is selected from the group consisting of hydrogen and $C_{1-6}$alkyl;

$R^{3b}$ is selected from the group consisting of hydrogen and $C_{1-6}$alkyl; or $R^{3a}$ and $R^{3b}$ form together with the nitrogen to which they are attached form a heterocycloalkyl;

$R^{3c}$ is hydrogen;

$R^4$ is selected from the group consisting of amino, —$C(=O)N(R^{3a},R^{3b})$, $C_{1-6}$alkoxy, $C_{1-6}$alkyl, halo-$C_{1-6}$alkyl, and hydroxy-$C_{1-6}$alkyl;

$R^6$ is selected from the group consisting of
i) unsubstituted aryl;
ii) unsubstituted heteroaryl; and
iii) heteroaryl substituted by 1 or 2 substituents selected from $R^7$;

$R^7$ is selected from the group consisting of
i) unsubstituted heteroaryl; and
ii) heteroaryl substituted by 1 or 2 substituents selected from $R^8$;

$R^8$ is $C_{1-6}$alkyl;

Y is $CH_2$ or NH;

$R^9$ is selected from the group consisting of
i) $C_{1-6}$alkyl; and
ii) —$C(=O)O$—$C_{1-6}$alkyl;

$R^{10}$ is selected from the group consisting of
i) $C_{1-6}$alkyl; and
ii) —$C(=O)O$—$C_{1-6}$alkyl.

2. The method of claim 1, wherein $X^1$ is N.

3. The method of claim 1, wherein $X^2$ is N.

4. The method of claim 1, wherein $X^3$ is N.

5. The method of claim 1, wherein $R^3$ is aryl substituted by 1 or 2 substituents selected from $R^4$, wherein $R^4$ is selected from the group consisting of —$C(=O)N(R^{3a},R^{3b})$, $C_{1-6}$alkyl, and $C_{1-6}$alkoxy.

6. The method of claim 1, wherein $R^3$ is-$C(=O)N(R^{3a},R^{3b})$.

7. The method of claim 6, wherein $R^{3a}$ is hydrogen and $R^{3b}$ is $C_{1-6}$alkyl.

8. The method of claim 7, wherein $R^{3b}$ is methyl.

9. The method of claim 1, wherein $R^1$ is-$C(=O)$—$R^6$.

10. The method of claim 1, wherein $R^1$ is heterocyclyl.

11. The method of claim 1, wherein $R^1$ is heterocyclyl, substituted by 1 or 2 substituents individually selected from $R^{10}$.

12. The method of claim 1, wherein $R^1$ is aryl.

13. The method of claim 1, wherein $R^1$ is aryl, substituted by 1 or 2 substituents individually selected from $R^9$.

* * * * *